US008716484B1

(12) United States Patent
Kwong et al.

(10) Patent No.: US 8,716,484 B1
(45) Date of Patent: May 6, 2014

(54) HOLE TRANSPORTING MATERIALS WITH TWISTED ARYL GROUPS

(71) Applicants: Raymond Kwong, Shatin (HK); Sze Kui Lam, Shatin (HK); Kit Yee Tsang, Shatin (HK)

(72) Inventors: Raymond Kwong, Shatin (HK); Sze Kui Lam, Shatin (HK); Kit Yee Tsang, Shatin (HK)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 13/705,468

(22) Filed: Dec. 5, 2012

(51) Int. Cl.
C07D 401/00 (2006.01)

(52) U.S. Cl.
USPC ..................................... 546/268.1

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,550,290 A * | 8/1996 | Mizuta et al. | 564/309 |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,921,915 B2 | 7/2005 | Takiguchi et al. | |
| 7,090,928 B2 | 8/2006 | Thompson et al. | |
| 7,154,114 B2 | 12/2006 | Brooks et al. | |
| 7,230,107 B1 | 6/2007 | Herron et al. | |
| 7,232,618 B2 | 6/2007 | Yamada et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 7,655,323 B2 | 2/2010 | Walters et al. | |
| 7,968,146 B2 | 6/2011 | Wagner et al. | |
| 2001/0015432 A1 | 8/2001 | Igarashi | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0115476 A1 | 6/2004 | Oshiyama et al. | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0123751 A1 | 6/2005 | Tsutsui et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2006/0008670 A1 | 1/2006 | Lin et al. | |
| 2006/0121308 A1 | 6/2006 | Katoh et al. | |
| 2006/0127696 A1 | 6/2006 | Stossel et al. | |
| 2006/0182992 A1 | 8/2006 | Nii et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0087321 A1 | 4/2007 | Pribenszky et al. | |
| 2007/0103060 A1 | 5/2007 | Itoh et al. | |
| 2007/0111026 A1 | 5/2007 | Deaton et al. | |
| 2007/0190359 A1 | 8/2007 | Knowles et al. | |

(Continued)

FOREIGN PATENT DOCUMENTS

| | | |
|---|---|---|
| EP | 650955 | 5/1995 |
| EP | 1725079 | 11/2006 |

(Continued)

OTHER PUBLICATIONS

Adachi et al., "High-efficiency red electrophosphorescence devices", Applied Physics Letters, vol. 78, No. 11, Mar. 12, 2001.

(Continued)

*Primary Examiner* — Heidi Reese

(74) *Attorney, Agent, or Firm* — Morris & Kamlay LLP

(57) ABSTRACT

Novel compounds, and in particular, novel molecules having twisted aryl groups are provided. In particular, the compounds include an aryl group at the ortho position relative to an amine nitrogen, thereby causing a twist within the compound from the plane of the aryl group due to the steric effect. As a result, this decreases the tendency of the molecules to pack closely and results in a higher solid state triplet energy due to reduced solid state π-stacking. Additionally, organic light emitting devices (OLEDs) comprising a layer including these novel compounds are provided.

11 Claims, 3 Drawing Sheets

(56) References Cited

U.S. PATENT DOCUMENTS

| | | |
|---|---|---|
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1 | 10/2008 | Kwong et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0302743 A1 | 12/2009 | Kato et al. |
| 2009/0309488 A1 | 12/2009 | Kato et al. |
| 2010/0012931 A1 | 1/2010 | Kato et al. |
| 2010/0084966 A1 | 4/2010 | Otsu et al. |
| 2010/0090591 A1 | 4/2010 | Alleyne et al. |
| 2010/0148663 A1 | 6/2010 | Tsai et al. |
| 2010/0187984 A1 | 7/2010 | Lin et al. |
| 2010/0244004 A1 | 9/2010 | Xia et al. |
| 2010/0295032 A1 | 11/2010 | Kwong et al. |
| 2011/0057559 A1 | 3/2011 | Xia et al. |
| 2011/0163302 A1 | 7/2011 | Lin et al. |
| 2011/0204333 A1 | 8/2011 | Xia et al. |

FOREIGN PATENT DOCUMENTS

| | | |
|---|---|---|
| EP | 1841834 | 10/2007 |
| EP | 2034538 | 3/2009 |
| EP | 2350216 | 8/2011 |
| JP | 2001316338 | 11/2001 |
| JP | 2007123392 | 5/2007 |
| JP | 2007254297 | 10/2007 |
| JP | 2008074939 | 4/2008 |
| JP | 2008159779 | 7/2008 |
| JP | 2011173973 | 9/2011 |
| WO | 2004/093207 | 10/2004 |
| WO | 2004/107822 | 12/2004 |
| WO | 2005/014551 | 2/2005 |
| WO | 2005/019373 | 3/2005 |
| WO | 2005/030900 | 4/2005 |
| WO | 2005/089025 | 9/2005 |
| WO | 2005/123873 | 12/2005 |
| WO | 2006/009024 | 1/2006 |
| WO | 2006/056418 | 6/2006 |
| WO | 2006/072002 | 7/2006 |
| WO | 2006/082742 | 8/2006 |
| WO | 2006/098120 | 9/2006 |
| WO | 2006/100298 | 9/2006 |
| WO | 2006/103874 | 10/2006 |
| WO | 2006/114966 | 11/2006 |
| WO | 2006/132173 | 12/2006 |
| WO | 2007/002683 | 1/2007 |
| WO | 2007/004380 | 1/2007 |
| WO | 2007/063754 | 6/2007 |
| WO | 2007/063796 | 6/2007 |
| WO | 2008/056746 | 5/2008 |
| WO | 2008/057394 | 5/2008 |
| WO | 2008/101842 | 8/2008 |
| WO | 2008/132085 | 11/2008 |
| WO | 2009/000673 | 12/2008 |
| WO | 2009/003898 | 1/2009 |
| WO | 2009/008311 | 1/2009 |
| WO | 2009/018009 | 2/2009 |
| WO | 2009/021126 | 2/2009 |
| WO | 2009/050290 | 4/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 2009/100991 | 8/2009 |
| WO | 2010011390 | 1/2010 |
| WO | 2010/028151 | 3/2010 |
| WO | 2010/056066 | 5/2010 |
| WO | 2010/079051 | 7/2010 |
| WO | 2010/086089 | 8/2010 |
| WO | 2010/107244 | 9/2010 |
| WO | 2011/044988 | 4/2011 |
| WO | 2011/051404 | 5/2011 |
| WO | 2011/075644 | 6/2011 |
| WO | 2011/086863 | 7/2011 |

OTHER PUBLICATIONS

Adachi et al., "Nearly 100% internal phosphorescence efficiency in an organic light emitting device", Journal of Applied Physics, vol. 90, No. 10, Nov. 15, 2001.

Adachi et al., "Organic electroluminescent device having a hole conductor as an emitting layer", Applied Physics Letters, vol. 55, Oct. 9, 1989.

Aonuma et al., "Material design of hole transport materials capable of thick-filim formation in organic light emitting diodes", Applied Physics Letters, vol. 90, 2007.

Baldo et al., "Highly efficient phosphorescent emission from organic electroluminescent devices", Nature, vol. 395, pp. 151-154, 1998.

Baldo et al., "Very high-efficiency green organic light-emitting devices based on electrophosphorescence", Applied Physics Letter, vol. 75, No. 1, pp. 4-6, 1999.

Chang et al., "Highly Efficient Blue-Emitting Iridium(III) Carbene Complexes and Phosphorescent OLEDs", Angew. Chem. Int. Ed. 47, pp. 4542-4545, 2008.

Gao et al., "Bright-blue electroluminescence from a silyl-substituted ter-(phenylene-vi nylene) derivative", Applied Physics Letters, vol. 74, No. 6, Feb. 8, 1999.

Guo et al., "Highly efficient electrophosphorescent polymer light-emitting devices", Organic Electronics 1, pp. 15-20, 2000.

Hamada et al., "High Luminance in Organic Electroluminescent Devices with Bis(10-hydroxybenzo[h]quinolinato)beryllium as an Emitter", Chemistry Letters, pp. 905-906, 1993.

Holmes et al., "Blue organic electrophosphorescence using exothermic host-guest energy transfer", Applied Physics Letters, vol. 82, No. 15, Apr. 14, 2003.

Hu et al., "Novel high Tg hole-transport molecules based on indolo[3,2-b ]carbazoles for organic light-emitting devices", Synthetic Metals 111-112, pp. 421-424, 2000.

Huang et al., "Highly Efficient Red-Emission Polymer Phosphorescent Light-Emitting Diodes Based on Two Novel Tris(I-phenylisoquinolinato-C2,N)iridium(III) Derivatives", Advanced Materials, No. 19, 2007.

Huang et al., "Highly Phosphorescent Bis-Cyclometalated Iridium Complexes Containing Benzoimidazole-Based Ligands", Chemistry of Materials, vol. 16, 2004.

Hung et al., "Anode modification in organic light-emitting diodes by low-frequency plasma polymerization of CHF3", Applied Physics Letters, vol. 78, No. 5, Jan. 29, 2001.

Ikeda et al., "P-185: Low-Drive-Voltage OLEDs with a Buffer Layer Having Molybdenum Oxide", Society for Information Display Digest, pp. 923-926, 2006.

Kanno et al., "Highly efficient and stable red phosphorescent organic light-emitting device using bis[2-(2-benzothiazoyl)phenolato]zinc(II) as host material", Applied Physics Letters, vol. 90, 2007.

Kido et al., "1,2,4-Triazole Derivative as an Electron Transport Layer in Organic Electroluminescent Devices", Japanese Journal of Applied Physics, vol. 32, pp. L 917-L 920 Part 2, No. 7A, Jul. 1, 1993.

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-

(56) References Cited

OTHER PUBLICATIONS methylphenylphenylamino) triphenylamine (m-MTDATA), as Hole-Transport Materials", Advanced Materials, 6, No. 9, 1994.
Kwong et al., "High operational stability of electrophosphorescent devices", Applied Physics Letters, vol. 81, No. 1, Jul. 1, 2002.
Lamansky et al., "Synthesis and Characterization of Phosphorescent Cyclometalated Iridium Complexes", Inorganic Chemistry, vol. 40, No. 7, 2001.
Lee et al., "Polymer phosphorescent light-emitting devices doped with tris(2- phenylpyridine) iridium as a triplet emitter", Applied Physics Letters, vol. 77, No. 15, Oct. 9, 2000.
Lkai et al., "Highly efficient phosphorescence from organic light-emitting devices with an exciton-block layer", Applied Physics Letters, vol. 79, No. 2, Jul. 9, 2001.
Lnada et al., "1,3,5-Tris[4-(diphenylamino)phenyl]benzene and its Methyl substituted Derivatives as a Novel Class of Amorphous Molecular Materials", Journal of Materials Chemistry, vol. 3, 1993.
Lo et al., "Blue Phosphorescence from Iridium(III) Complexes at Room Temperature", Chemistry of Materials, vol. 18, 2006.
Ma et al., "Triplet luminescent dinuclear-gold complex-based light-emitting diodes with low turn-on voltage", Applied Physics Letters, vol. 74, No. 10, Mar. 8, 1999.
Mi et al., "Thermally Stable Hole-Transporting Material for Organic Light-Emitting Diode: an Isoindole Derivative", Chemistry of Materials, vol. 15, 2003.
Nishida et al., "Preparation, Characterization, and Electroluminescence Characteristics of a-Diimine-type Platinum(II) Complexes with Perfluorinated Phenyl Groups as Ligands", Chemistry Letters, vol. 34, No. 4, 2005.
Niu et al., "Highly Efficient Electrophosphorescent Devices with Saturated Red Emission from a Neutral Osmium Complex", Chemistry of Materials, vol. 17, 2005.
Noda et al., "5,5'-Bis(dimesitylboryl)-2,2'-bithiophene and 5,5''-Bis(dimesitylboryl)- 2,2':5',2''-terthiophene as a Novel Family of Electron-Transporting Amorphous Molecular Materials", Journal of the American Chemical Society, vol. 120, No. 37, 1998.
Okumoto et al., "Green fluorescent organic light-emitting device with external quantum efficiency of nearly 10%", Applied Physics Letters, vol. 89, 2006.
Ostergard et al., "Langmuir-Blodgett light-emitting diodes of poly(3-hexylthiophene): electro-optical characteristics related to structure", Synthetic Metals 88, pp. 171-177, 1997.
Palilis et al., "High efficiency molecular organic light-emitting diodes based on silole derivatives and their exciplexes", Organic Electronics 4, pp. 113-121, 2003.
Ranjan et al., "Realizing Green Phosphorescent Light-Emitting Materials from Rhenium(I) Pyrazolato Diimine Complexes", Inorganic Chemistry, vol. 42, No. 4, 2003.
Sakamoto et al., "Synthesis, Characterization, and Electron-Transport Property of Perfluorinated Phenylene Dendrimers", Journal of the American Chemical Society, vol. 122, No. 8, 2000.
Salbeck et al., "Low molecular organic glasses for blue electroluminescence", Synthetic Metals 91, pp. 209-215, 1997.
Shirota et al., "Starburst molecules based on pi-electron systems as materials for organic electroluminescent devices", Journal of Luminescence 72-74, pp. 985-991, 1997.
Sotoyama et al., "Efficient organic light-emitting diodes with phosphorescent platinum complexes containing $N^\wedge C^\wedge N$-coordinating tridentate ligand", Applied Physics Letters, vol. 86, 2005.
Sun et al., "High-efficiency white organic light emitting devices with three separate phosphorescent emission layers", Applied Physics Letters, vol. 91, 2007.
Takizawa et al., "Phosphorescent Iridium Complexes Based on 2-Phenylimidazo[1 ,2- a]pyridine Ligands: Tuning of Emission Color toward the Blue Region and Application to Polymer Light-Emitting Devices", Inorganic Chemistry, vol. 46, No. 10, 2007.
Tang et al., "Organic electroluminescent diodes", Applied Physics Letters, No. 51, Sep. 21, 1987.
Tung et al., "Highly Efficient Red Phosphorescent Osmium(II) Complexes for OLED Applications", Organometallics, 23, pp. 3745-3748, 2004.
Tung et al., "Organic Light-Emitting Diodes based on Charge-Neutral Ru Phosphorescent Emitters", Advanced Materials, 17, No. 8, Apr. 18, 2005.
Van Slyke et al., "Organic electroluminescent devices with improved stability", Applied Physics Letters, 69 (15), Oct. 7, 1996.
Wang et al., "Highly efficient electroluminescent materials based on fluorinated organometallic iridium compounds", Applied Physics Letters, vol. 79, No. 4, Jul. 23, 2001.
Wong et al., "A novel class of phosphorescent gold(III) alkynyl-based organic light-emitting devices with tunable colour", Chemical Communications, Royal Society of Chemistry, p. 2906-2908, 2005.
Wong et al., "Multifunctional Iridium Complexes Based on Carbazole Modules as Highly Efficient Electrophosphors", Angewandte Chemie, Int. Ed., No. 45, 2006.

* cited by examiner

Formula I

HOLE TRANSPORTING MATERIALS WITH TWISTED ARYL GROUPS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs) and materials for use therein. More specifically, it relates to devices and materials that include novel molecules having twisted aryl groups, and the use of such materials as hole transporting materials in a hole transport layer.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)3, which has the following structure:

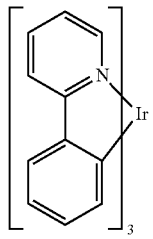

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In an aspect, a compound having the following general structure is provided:

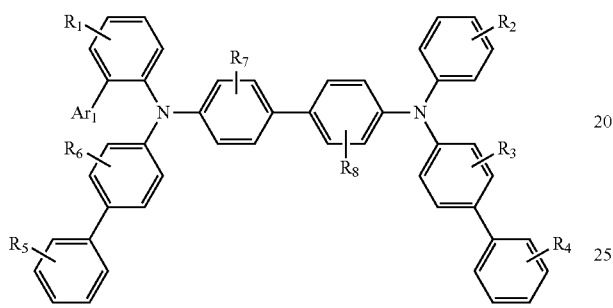

Formula I wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein each of $R_1$, $R_2$, $R_3$, $R_4$, $R_5$, $R_6$, $R_7$ and $R_8$ does not form cyclic rings, and wherein $Ar_1$ is selected from the group consisting of aryl and heteroaryl.

In an aspect, the compound has the following general structure:

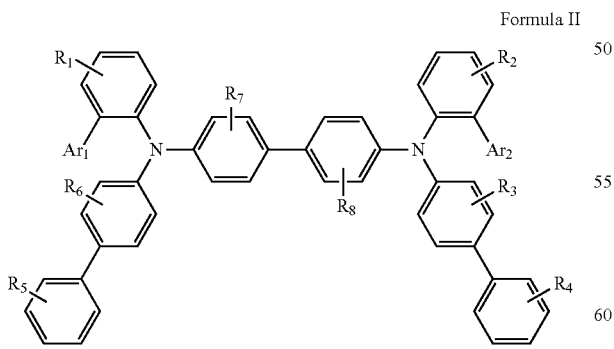

Formula II wherein $Ar_1$ and $Ar_2$ are independently selected from the group consisting of aryl and heteroaryl.

In an aspect, the compound has the following general structure:

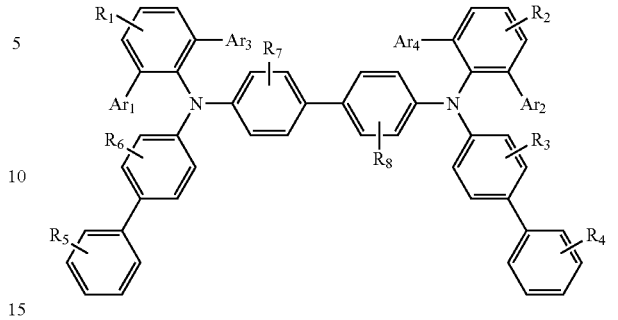

Formula III wherein $Ar_1$, $Ar_2$, $Ar_3$ and $Ar_4$ are independently selected from the group consisting of aryl and heteroaryl.

In an aspect, the compound is selected from the group including:

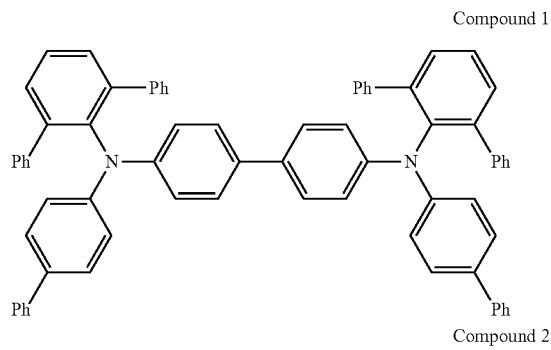

Compound 1

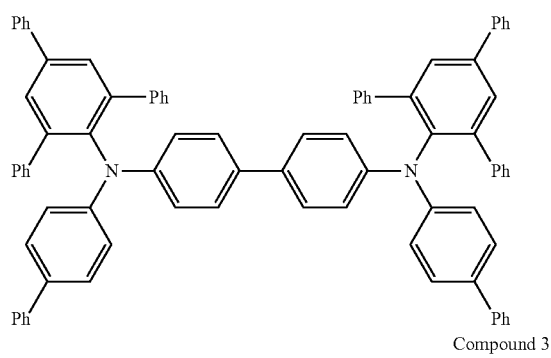

Compound 2

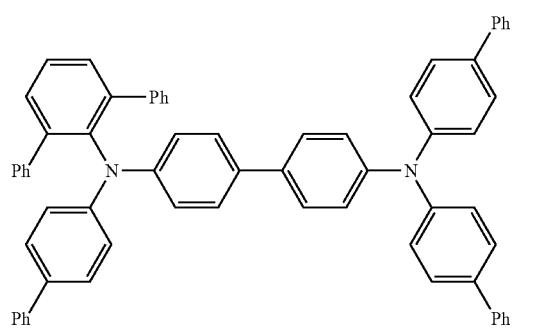

Compound 3

Compound 4
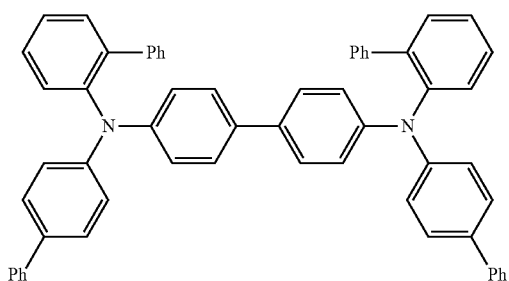
Compound 5
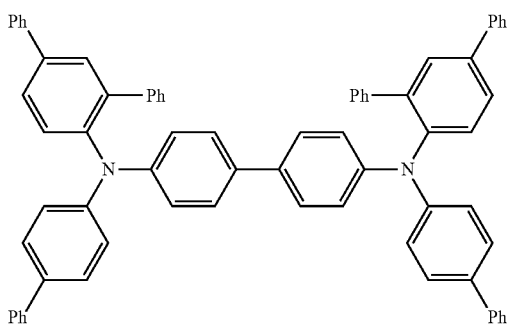
Compound 6
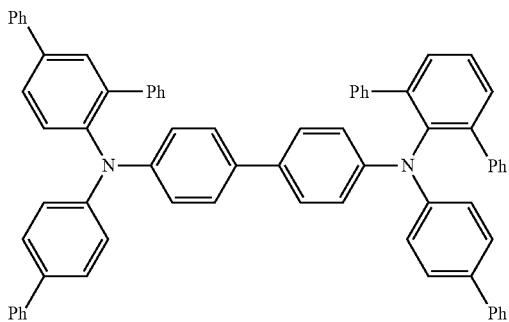
Compound 7
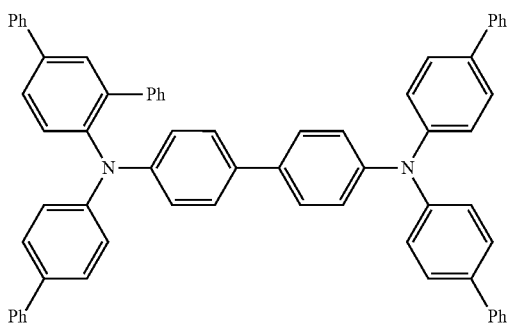
Compound 8
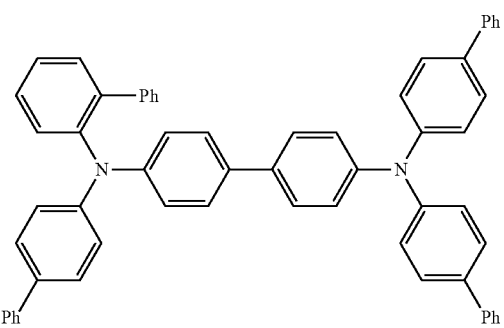
Compound 9
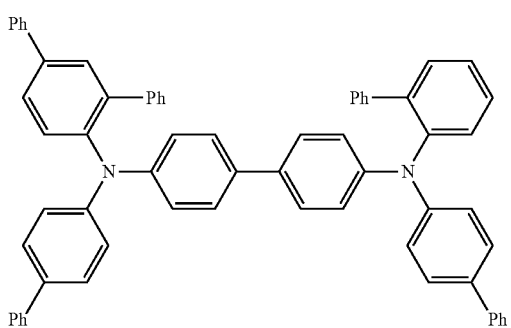
Compound 10
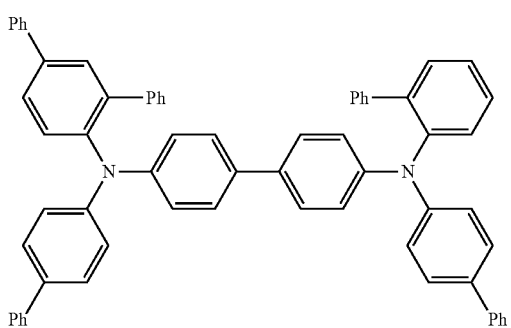
Compound 11
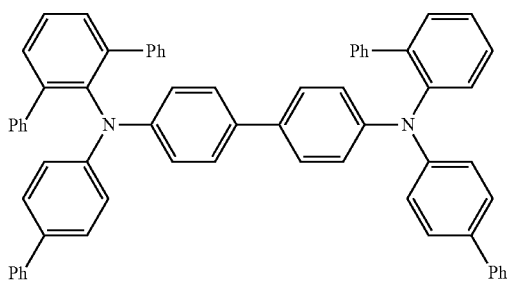

Compound 12
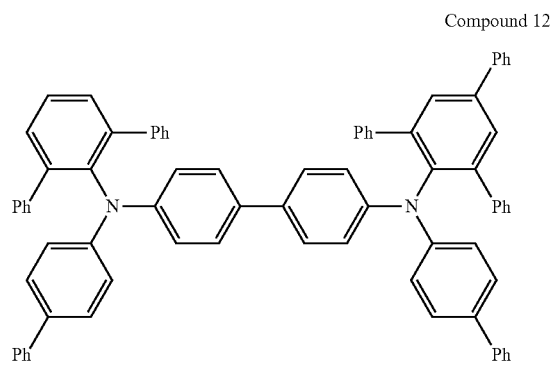
Compound 13
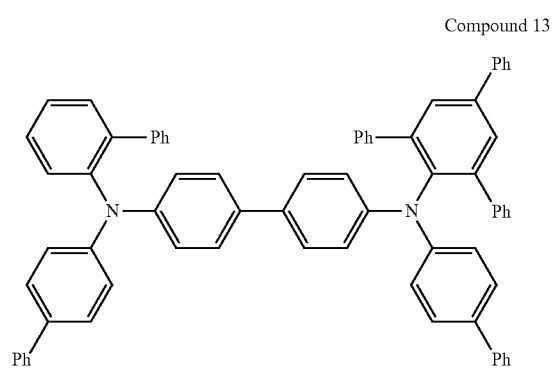
Compound 14
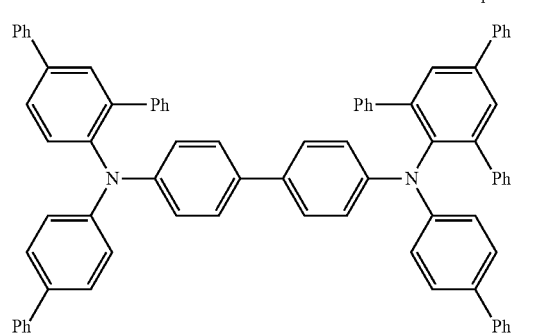
Compound 15
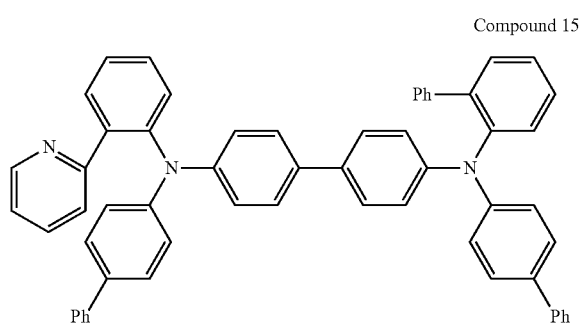
Compound 16
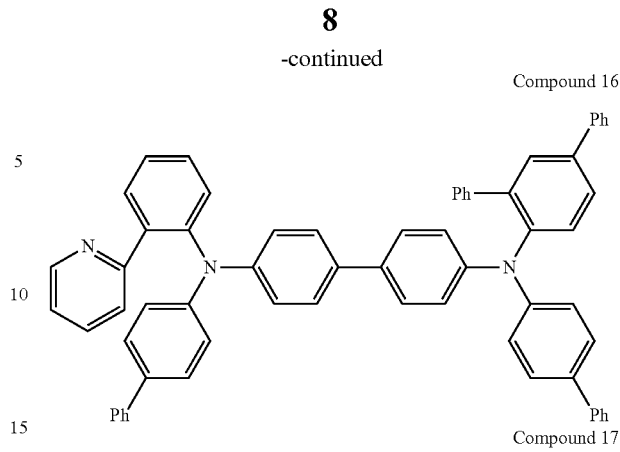
Compound 17
Compound 18
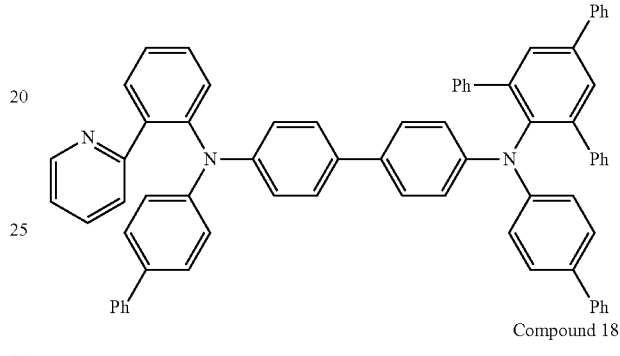
Compound 19
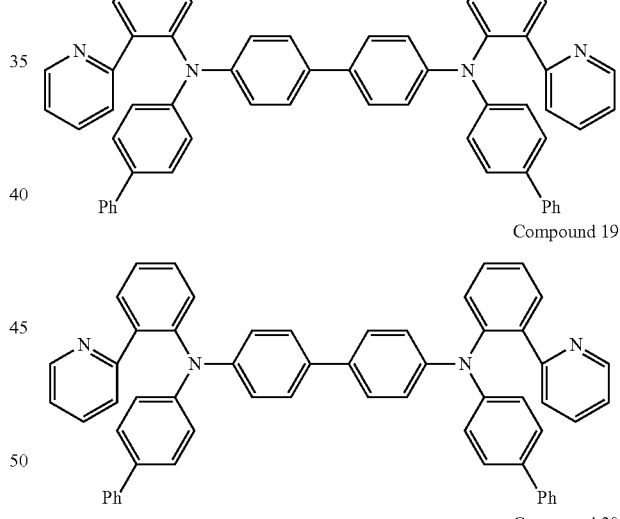
Compound 20
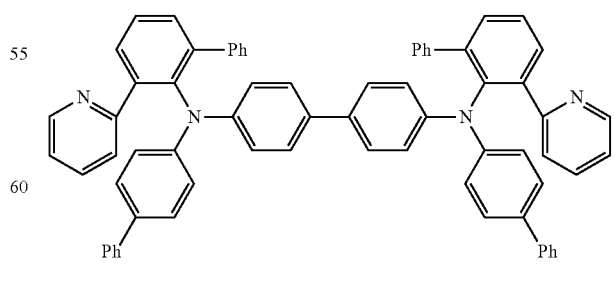
In an aspect, a device is provided which includes an organic light emitting device. The device comprises: an anode; a cathode; and an organic layer disposed between the anode and the cathode; wherein the organic layer comprises a compound having the following general structure:

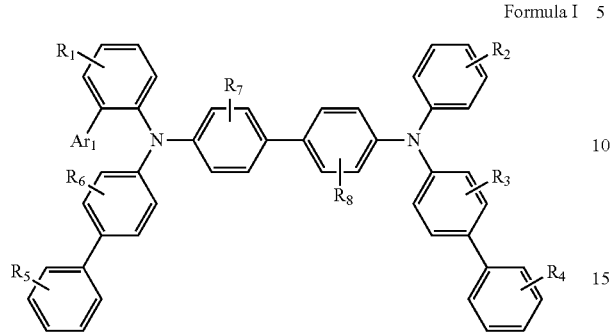

Formula I wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein $R_1$, $R_2$, $R_3$, $R_4$, $R_5$, $R_6$, $R_7$ and $R_8$ do not form cyclic rings, and wherein $Ar_1$ is selected from the group consisting of aryl and heteroaryl.

In an aspect, the device further comprises an emissive layer, and wherein the organic layer is disposed between the anode and the emissive layer. In an aspect, the organic layer is a hole transporting layer.

In an aspect, the device is a consumer product. In an aspect, the device is an organic light-emitting device. In an aspect, the device comprises a lighting panel.

In an aspect, the organic layer comprises a compound selected from the group including:

Compound 1

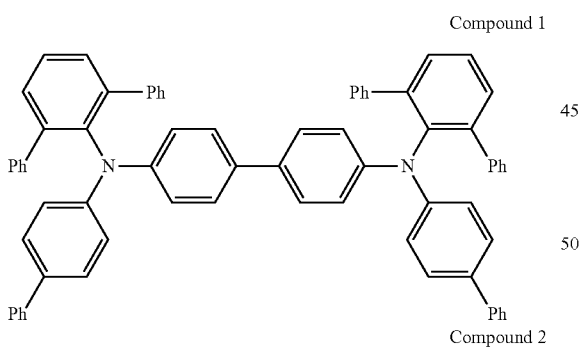

Compound 2

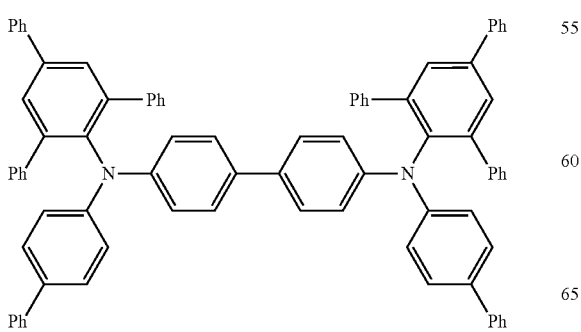

Compound 3

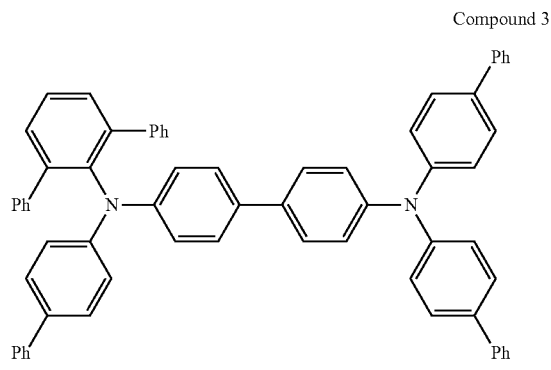

Compound 4

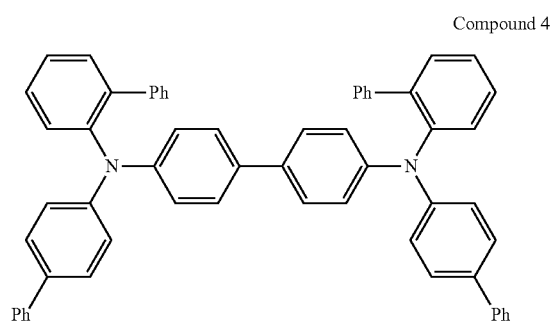

Compound 5

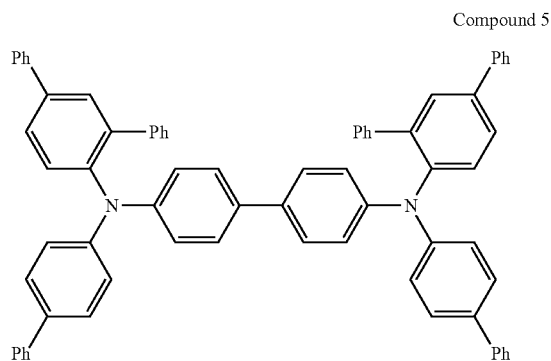

Compound 6

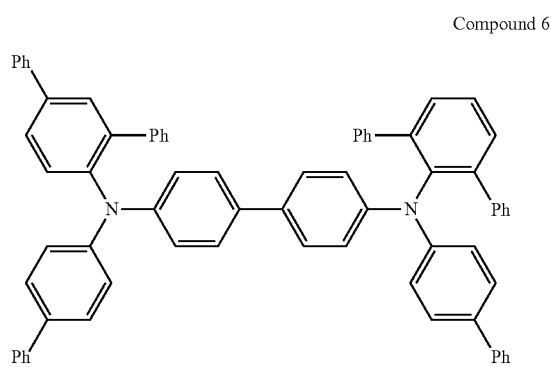

Compound 7
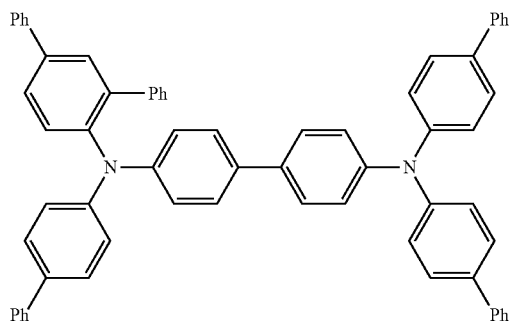
Compound 8
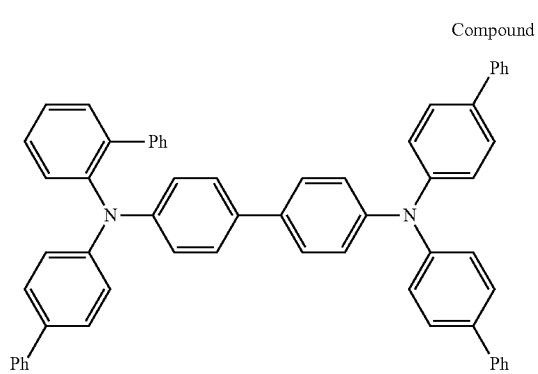
Compound 9
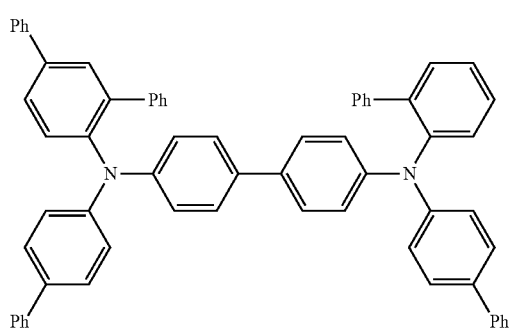
Compound 10
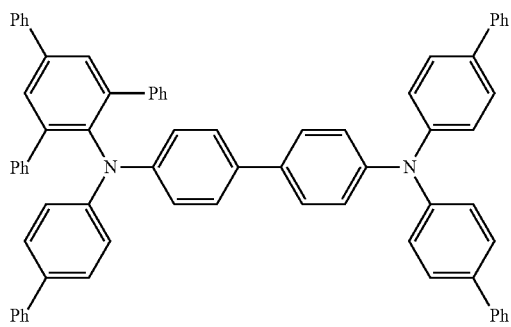
Compound 11
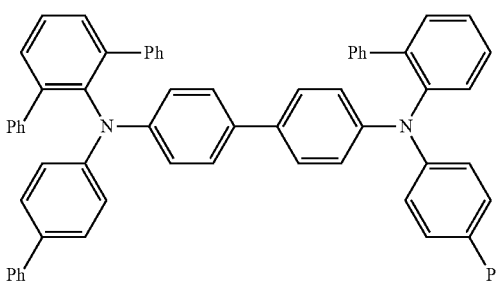
Compound 12
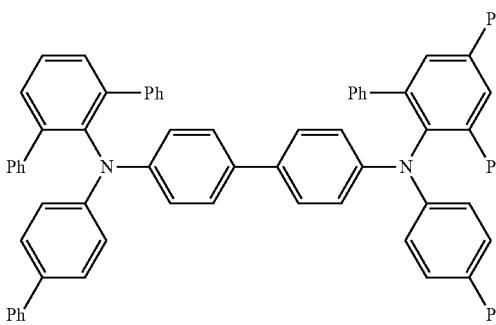
Compound 13
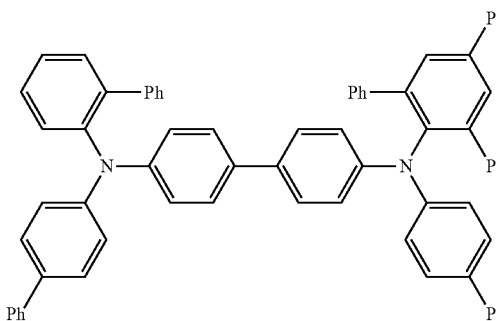
Compound 14
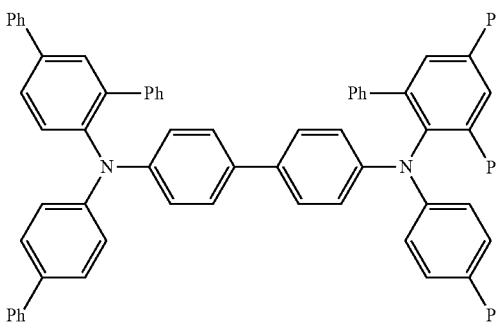
Compound 15
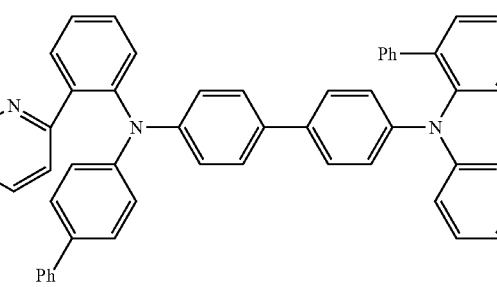

-continued

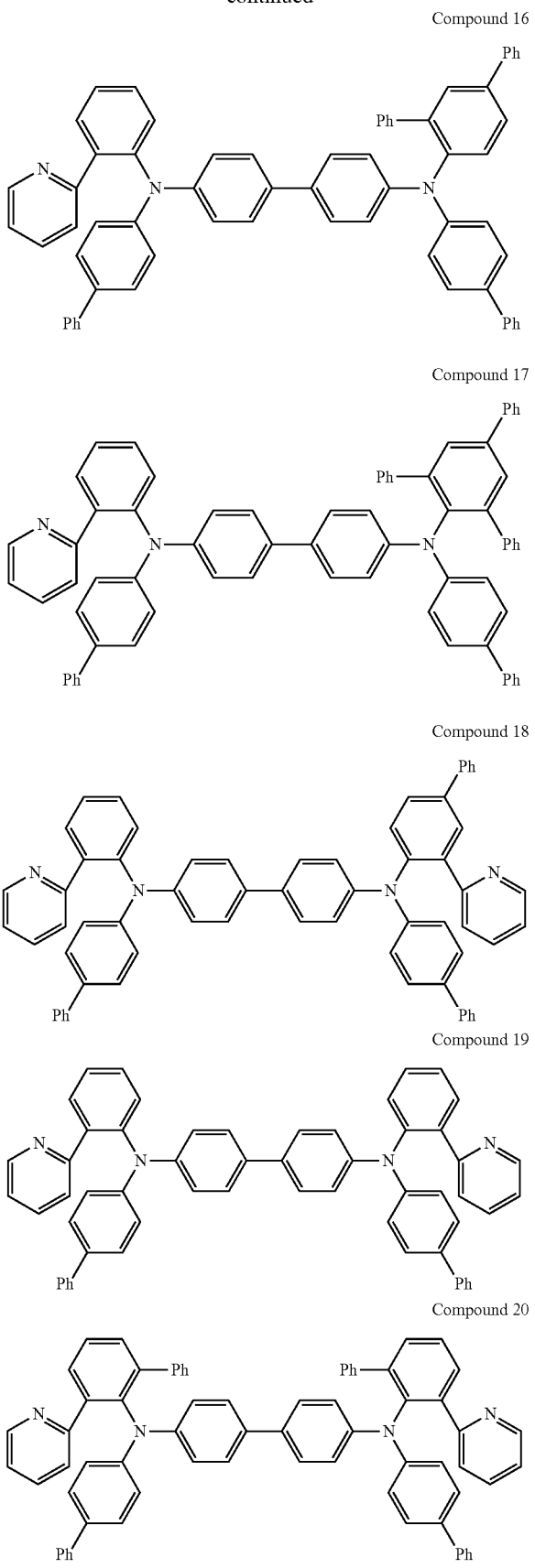

Compound 16

Compound 17

Compound 18

Compound 19

Compound 20

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
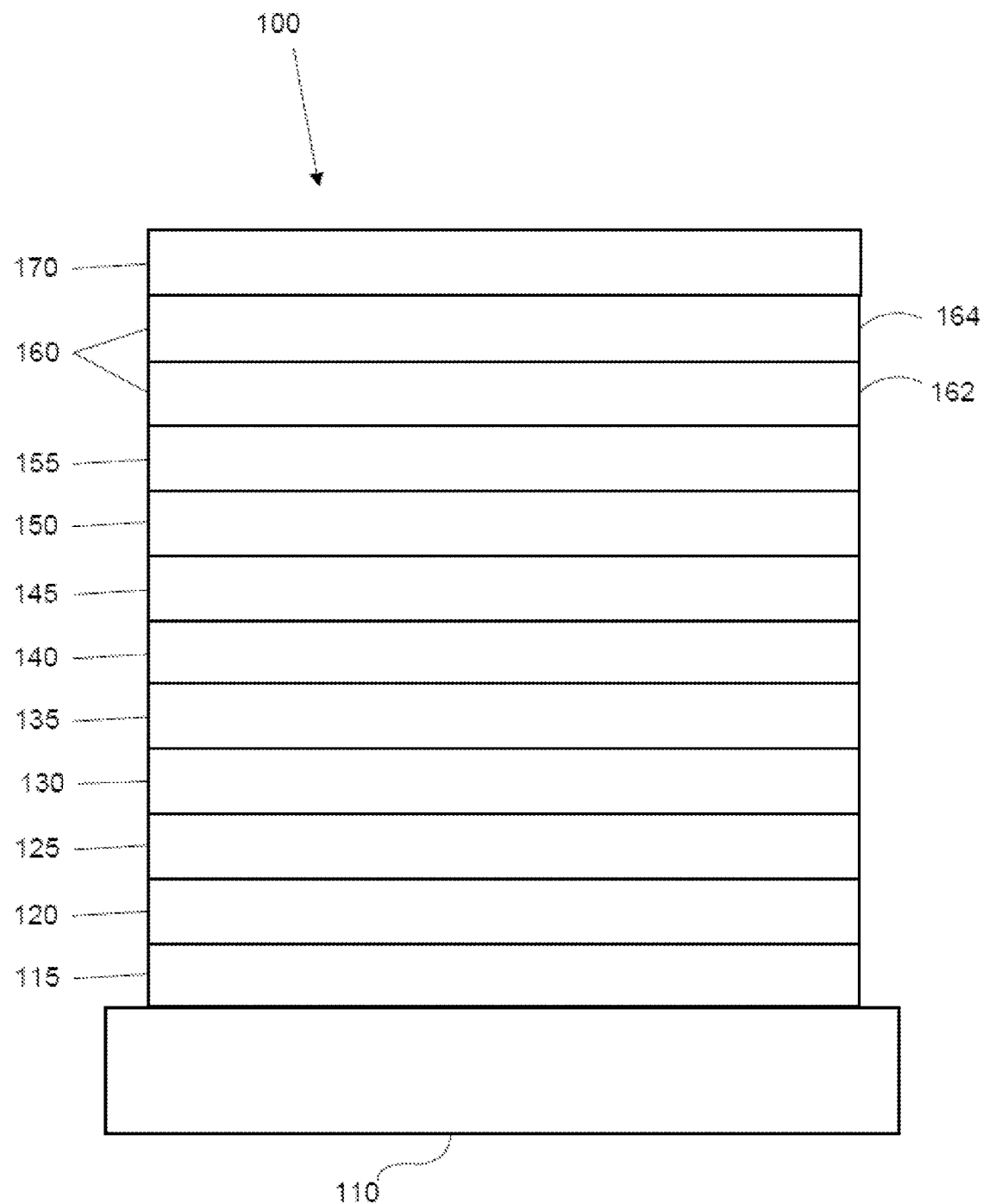
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
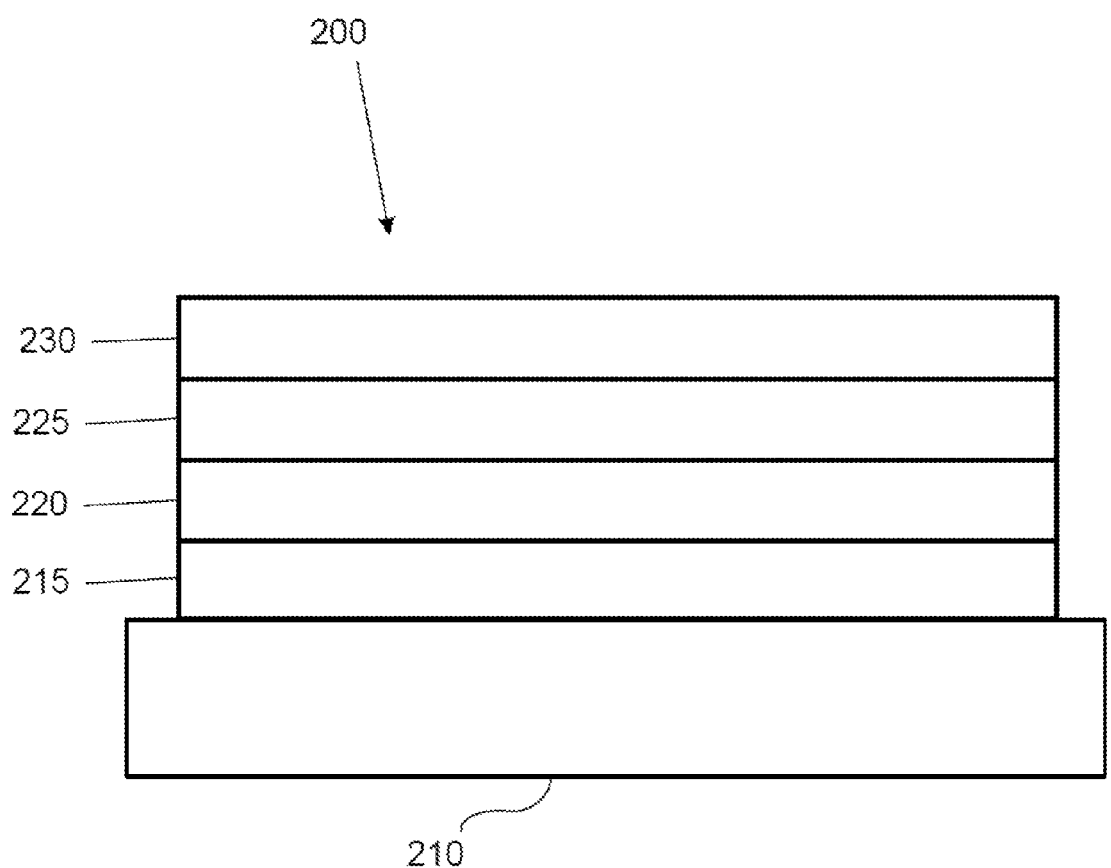
FIG. 2 shows an inverted organic light emitting device that does not have a separate electron transport layer.
Figure 3:
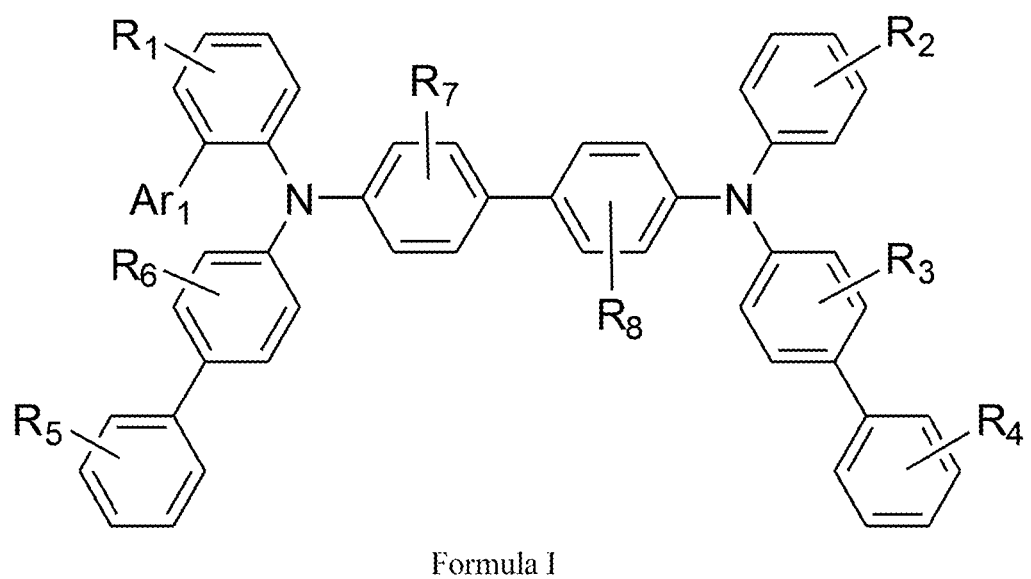
FIG. 3 shows a compound having a twisted aryl group.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In general, OLEDs with triarylamine hole transporter materials containing biphenyl groups are known to provide certain device properties. On the other hand, an important aspect is to keep the triplet energy high in order to achieve good device efficiency for blue and green phosphorescent OLEDs. In an aspect of the present invention, novel molecules having twisted aryl groups are provided, wherein 2-arylphenyl linkages (e.g., biphenyl-2-yl) are incorporated at the amino site. The ortho aryl group provides a twist from the plane of the aryl connected to the amine nitrogen due to the steric effect. As a result, this decreases the tendency of the molecules to pack closely and results in a higher solid state triplet energy due to reduced solid state π-stacking.

The present invention provides phosphorescent OLEDs with enhanced efficiency and/or lifetime as compared to devices having hole transporting materials without twisted aryl groups. In particular, sterically encumbered hole transporting materials as the HTL in phosphorescent OLEDs provide higher efficiency and/or lifetime compared to devices with unmodified hole transporting layer. Furthermore, lower evaporation temperatures are achieved by using materials with twisted aryl groups, as provided herein.

In an embodiment of the invention a compound is provided having the following general structure:

Formula I

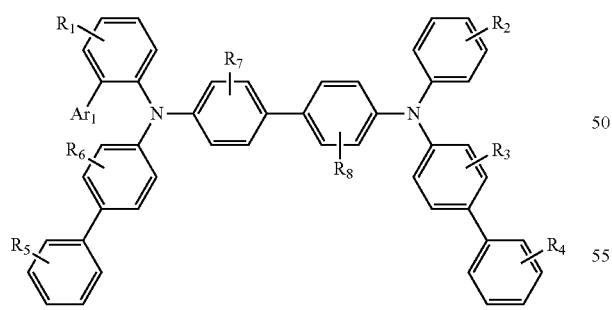

wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein each of $R_1$, $R_2$, $R_3$, $R_4$, $R_5$, $R_6$, $R_7$ and $R_8$ does not form cyclic rings, and wherein $Ar_1$ is selected from the group consisting of aryl and heteroaryl.

In an embodiment, the compound has the following general structure:

Formula II

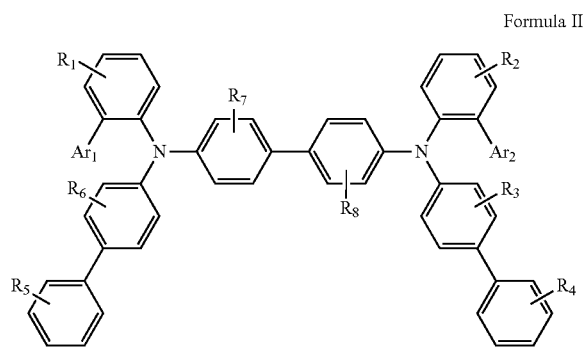

wherein $Ar_1$ and $Ar_2$ are independently selected from the group consisting of aryl and heteroaryl.

In some embodiments, the compound has the following general structure:

Formula III

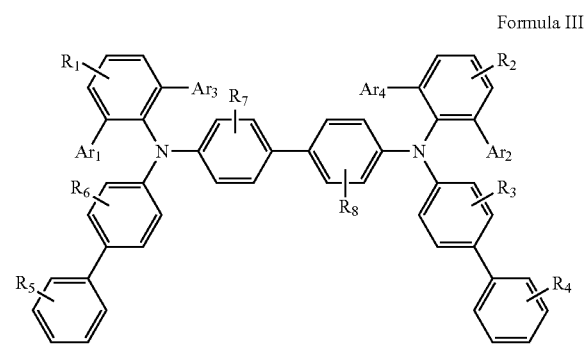

wherein $Ar_1$, $Ar_2$, $Ar_3$ and $Ar_4$ are independently selected from the group consisting of aryl and heteroaryl.

In an embodiment, examples of the compounds described herein may include but are not limited to the following as shown below:

Example Compounds

Compound 1

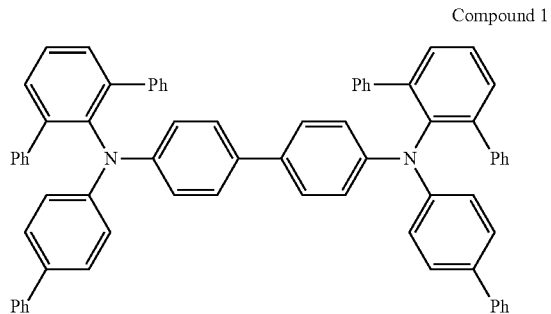

-continued
Compound 2
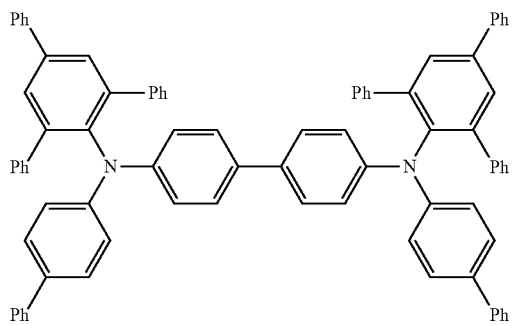
Compound 3
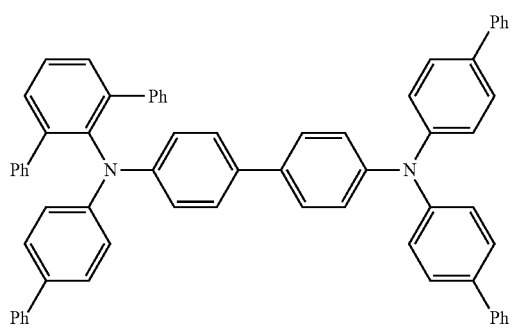
Compound 4
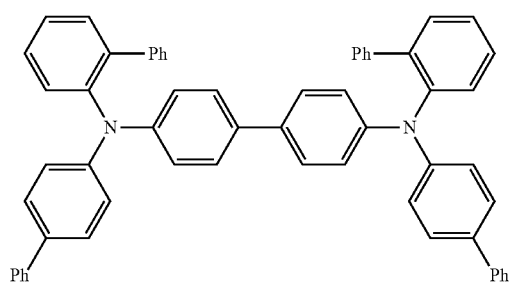
Compound 5
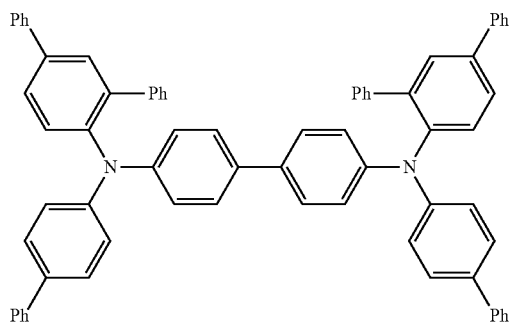
-continued
Compound 6
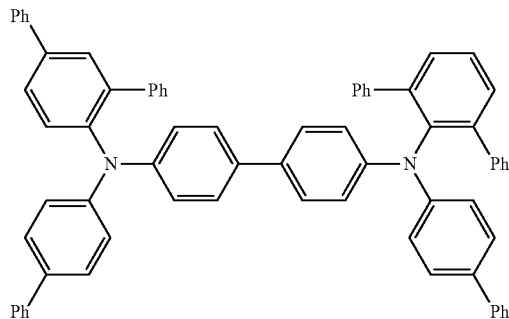
Compound 7
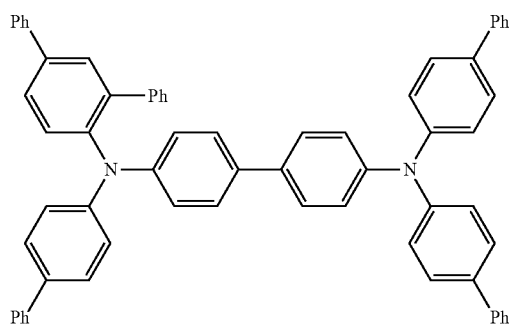
Compound 8
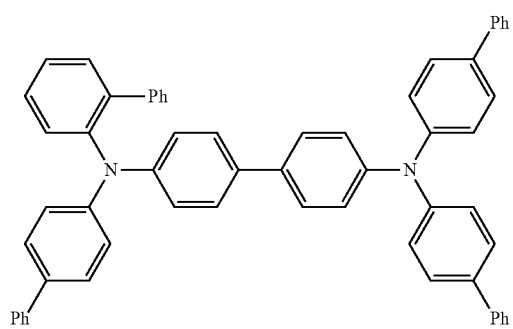
Compound 9
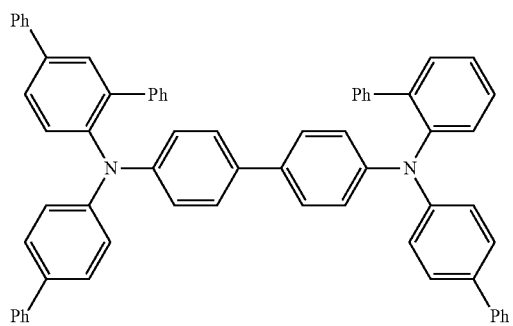

Compound 10
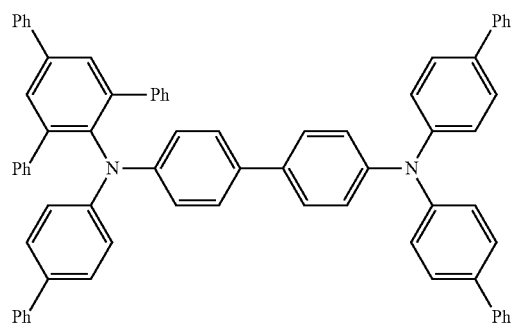
Compound 11
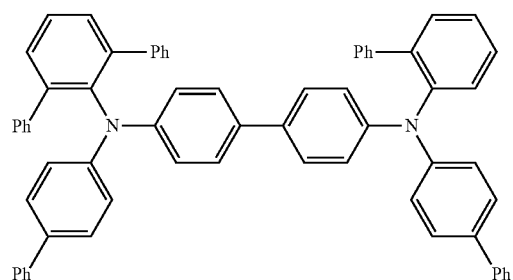
Compound 12
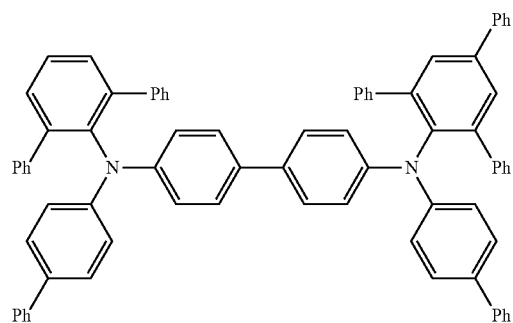
Compound 13
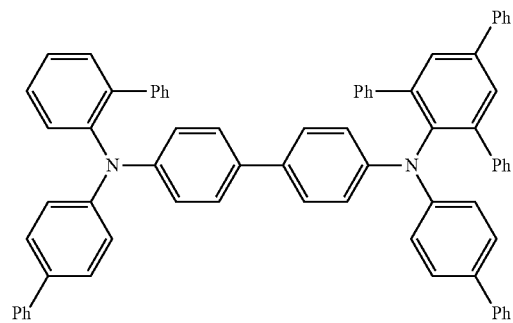
Compound 14
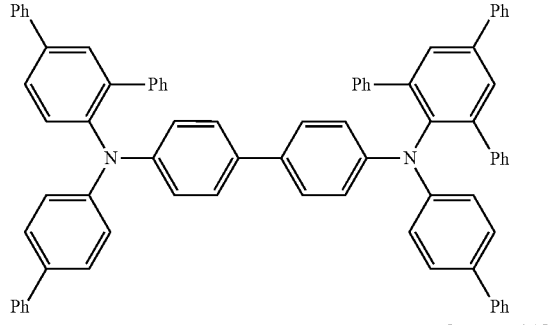
Compound 15
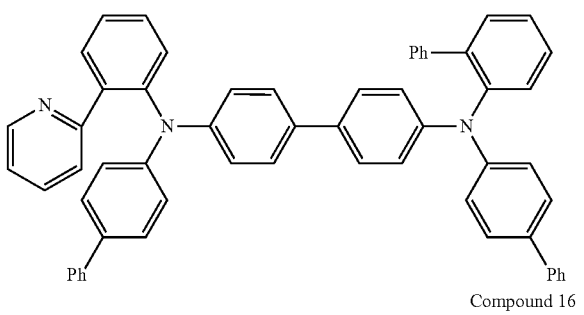
Compound 16
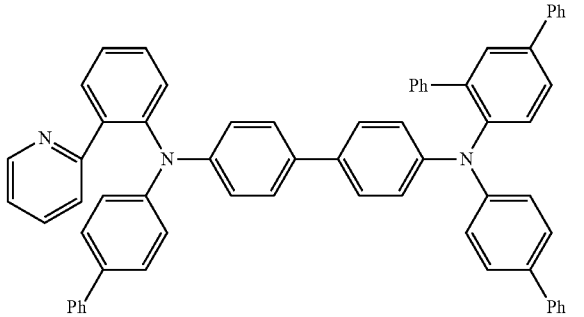
Compound 17
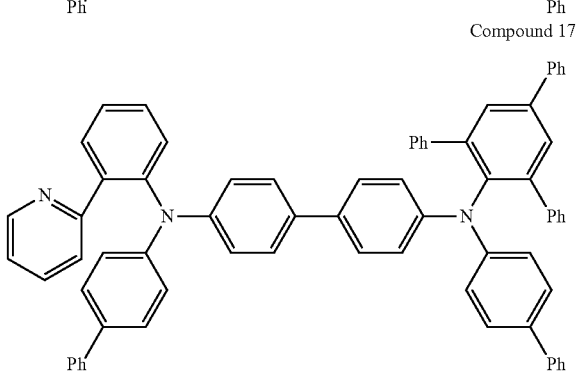
Compound 18
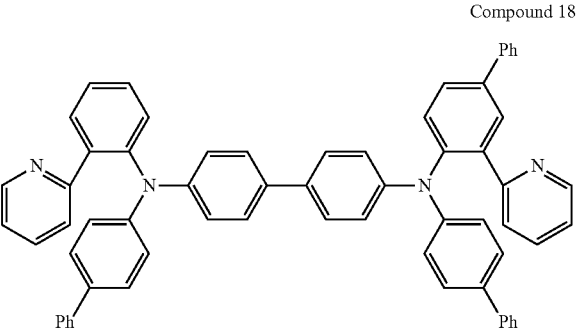

23
-continued

Compound 19

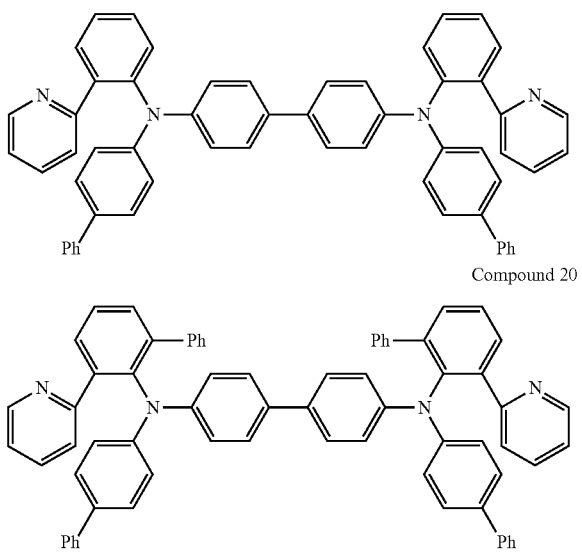

Compound 20

An organic light emitting device is also provided. The device comprises: an anode; a cathode; and an organic layer disposed between the anode and the cathode; wherein the organic layer comprises a compound having the following general structure:

Formula I

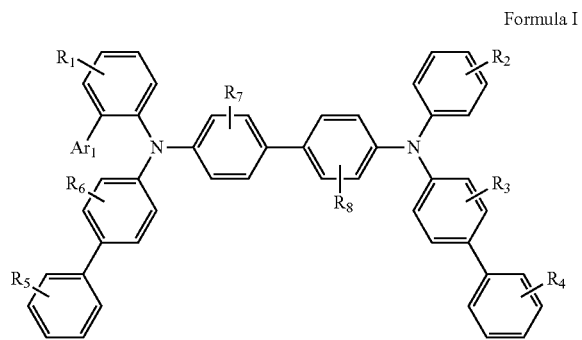

wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein $R_1$, $R_2$, $R_3$, $R_4$, $R_5$, $R_6$, $R_7$ and $R_8$ do not form cyclic rings, and wherein $Ar_1$ is selected from the group consisting of aryl and heteroaryl.

In an embodiment, the device may further comprise an emissive layer, wherein the organic layer is disposed between the anode and the emissive layer. In an embodiment, the organic layer may be a hole transporting layer. In particular, the organic layer may also include a compound as described in Table 1 above.

A consumer product including a compound as described above is also provided.

Further, the device may include an organic light-emitting device and/or a lighting panel.

24

An organic light emitting device is also provided. The device may include an anode, a cathode, and an organic emissive layer disposed between the anode and the cathode. The organic emissive layer may include a host and a phosphorescent dopant. The device may also include a compound as described above.

Furthermore, the molecules provided herein may be used in phosphorescent devices and fluorescent devices, and in both single color or multiple color devices. Further, the materials may be vapor-evaporated or solution processed.

In addition to the devices described above, the device may further include a touch sensitive surface. For example, the device may include a device type selected from the group consisting of: a full-color display, a flexible display in a consumer device, a mobile phone, a pad computer, a smartphone, a portable computer, a monitor, a television, and a consumer device including a flexible display.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

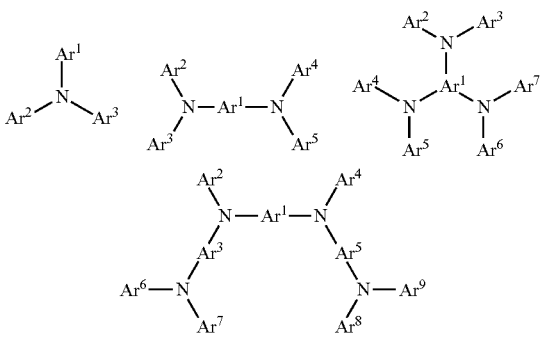

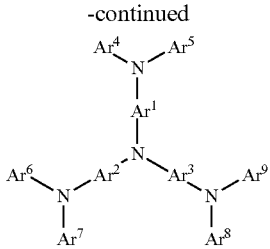

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

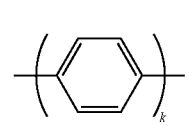
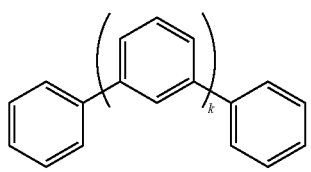
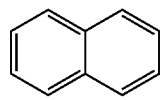
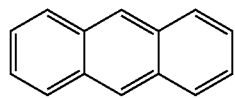
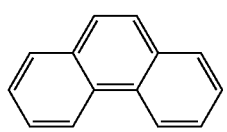
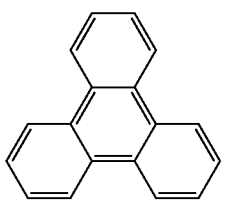

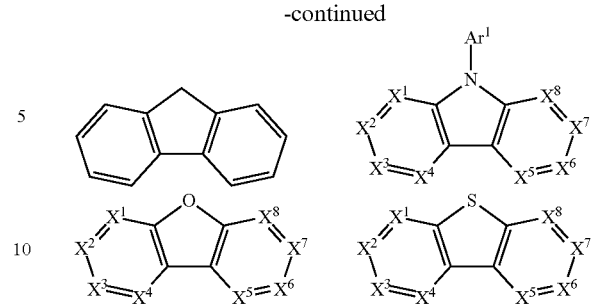

k is an integer from 1 to 20; $X^1$ to $X^8$ is C (including CH) or N; $Ar^1$ has the same group defined above.

Examples of metal complexes used in HIL or HTL include, but not limit to the following general formula:

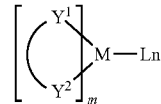

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While Table 2 below categorizes host materials as preferred for devices that emit various colors, any host material may be used with any dopant so long as the triplet criteria is satisfied.

Examples of metal complexes used as host are preferred to have the following general formula:

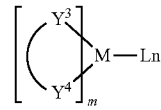

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

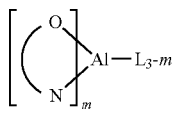 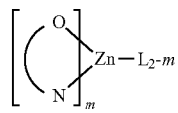

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

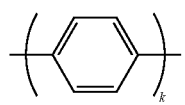 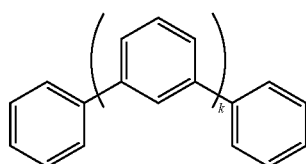

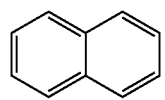 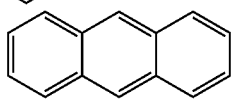

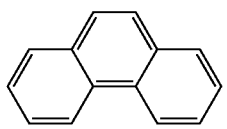 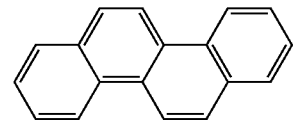

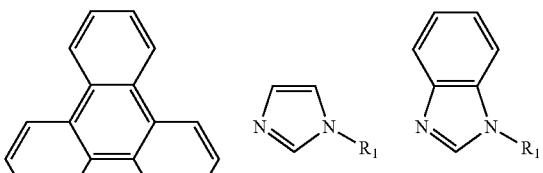

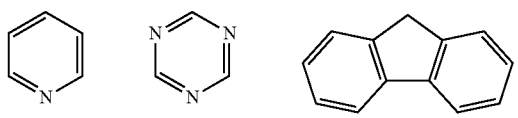

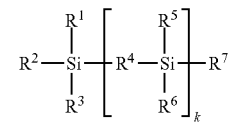

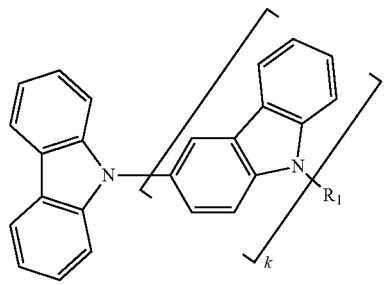

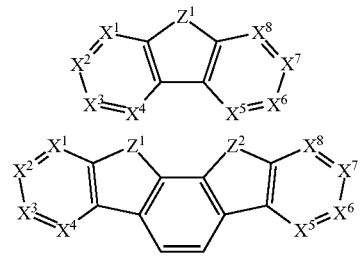

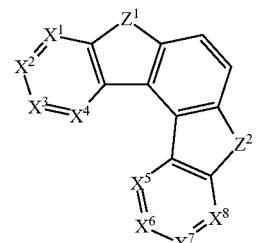

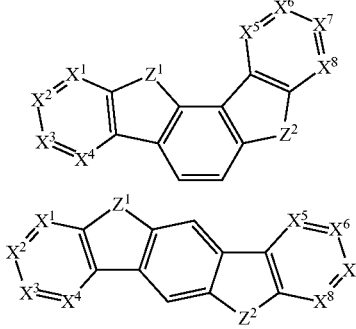

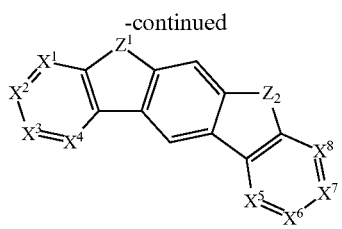

R[1] to R[7] is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

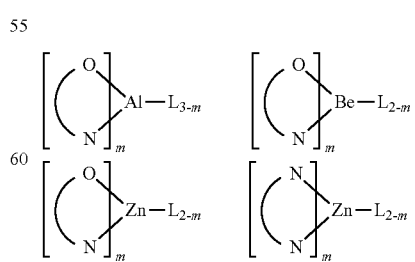

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

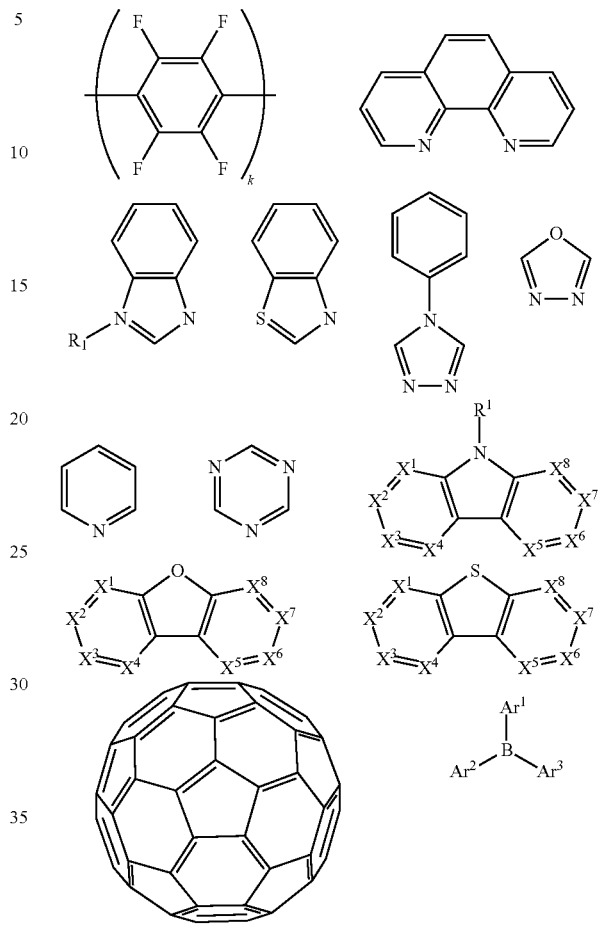

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| Hole injection materials | | |
| Phthalocyanine and porphryin compounds | 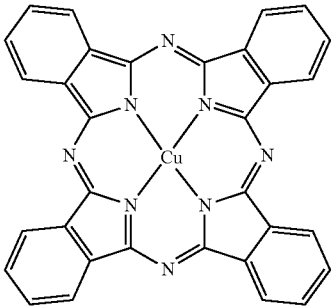 | Appl. Phys. Lett. 69, 2160 (1996) |
| Starburst triarylamines | 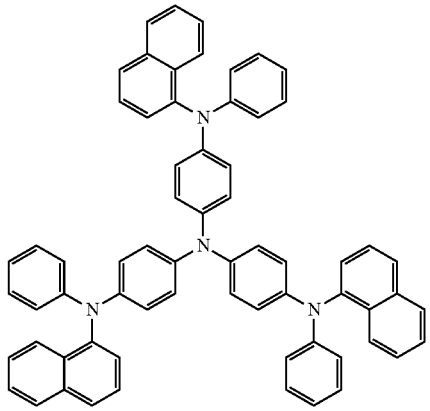 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| CF$_x$ Fluorohydrocarbon polymer | $-\!\!\left[CH_xF_y\right]_n\!\!-$ | Appl. Phys. Lett. 78, 673 (2001) |
| Conducting polymers (e.g., PEDOT:PSS, polyaniline, polypthiophene) | 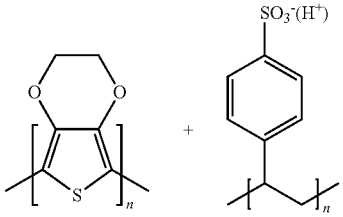 | Synth. Met. 87, 171 (1997) WO2007002683 |
| Phosphonic acid and sliane SAMs | 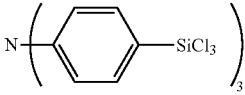 | US20030162053 |

TABLE 2-continued
| MATERIAL | EXAMPLES OF MATERIAL | PUBLICATIONS |
| --- | --- | --- |
| Triarylamine or polythiophene polymers with conductivity dopants | 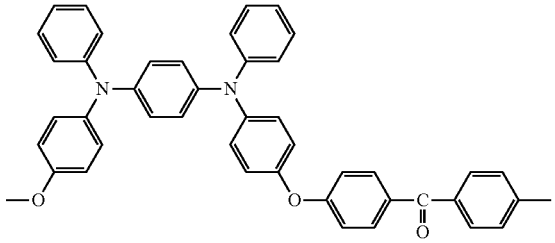 | EP1725079A1 |
| Organic compounds with conductive inorganic compounds, such as molybdenum and tungsten oxides | 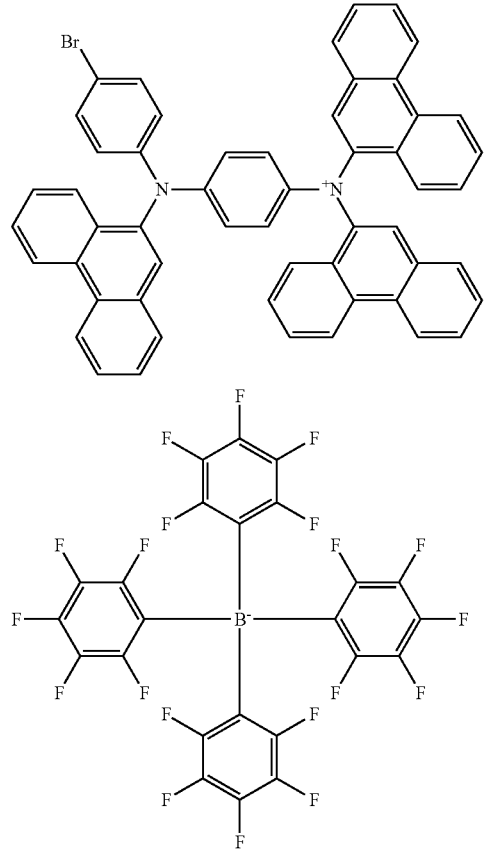 + MoO$_x$ | US20050123751<br>SID Symposium Digest, 37, 923 (2006)<br>WO2009018009 |

TABLE 2-continued
| MATERIAL | EXAMPLES OF MATERIAL | PUBLICATIONS |
|---|---|---|
| n-type semiconducting organic complexes | 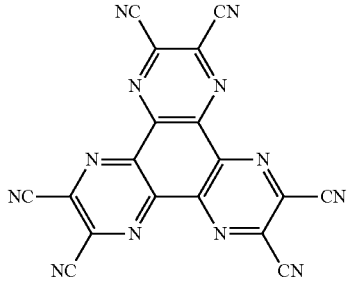 [SMILES: N#Cc1nc2c3nc(C#N)c(C#N)nc3c3nc(C#N)c(C#N)nc3c2nc1C#N] | US20020158242 |
| Metal organometallic complexes | 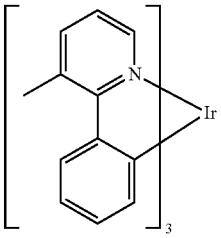 | US20060240279 |
| Cross-linkable compounds | 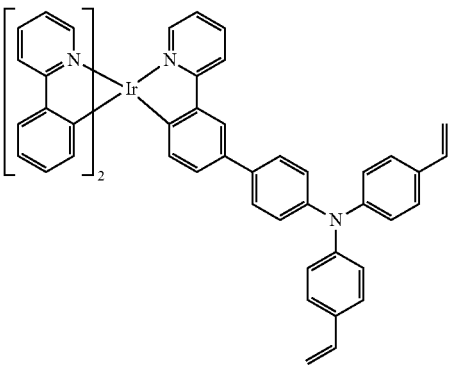 | US20080220265 |
| Polythiophene based polymers and copolymers | 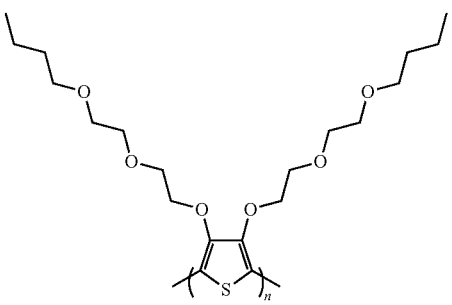 | WO 2011075644<br>EP2350216 |
| Hole transporting materials | | |
| Triarylamines (e.g., TPD, _-NPD) | 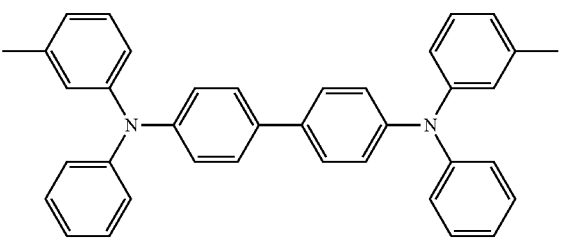 | Appl. Phys. Lett. 51, 913 (1987) |

TABLE 2-continued

| MATERIAL | EXAMPLES OF MATERIAL | PUBLICATIONS |
|---|---|---|
| | | U.S. Pat. No. 5,061,569 |
| | | EP650955 |
| | | J. Mater. Chem. 3, 319 (1993) |
| | | Appl. Phys. Lett. 90, 183503 (2007) |

TABLE 2-continued

| MATERIAL | EXAMPLES OF MATERIAL | PUBLICATIONS |
|---|---|---|
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |

TABLE 2-continued
| MATERIAL | EXAMPLES OF MATERIAL | PUBLICATIONS |
|---|---|---|
| Indolocarbazoles | 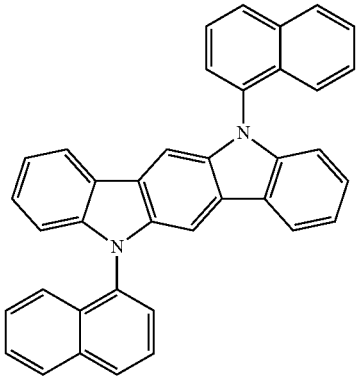 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 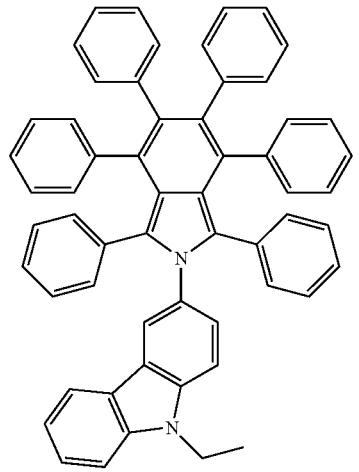 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 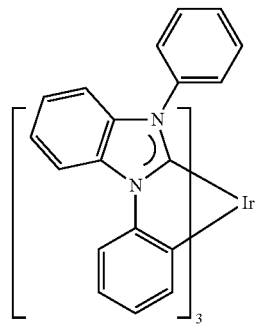 | US20080018221 |
Phosphorescent OLED host materials
Red hosts
| Arylcarbazoles | 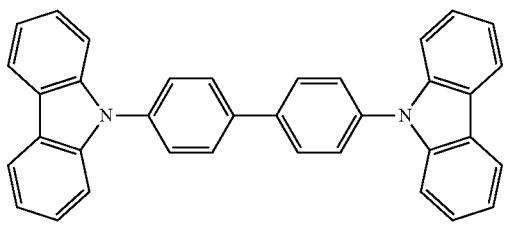 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 2-continued

| MATERIAL | EXAMPLES OF MATERIAL | PUBLICATIONS |
|---|---|---|
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833 US20090045731, US20090045730, WO2009008311, US20090008605, US20090009065 |

TABLE 2-continued

| MATERIAL | EXAMPLES OF MATERIAL | PUBLICATIONS |
| --- | --- | --- |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 2-continued
| MATERIAL | EXAMPLES OF MATERIAL | PUBLICATIONS |
|---|---|---|
| | 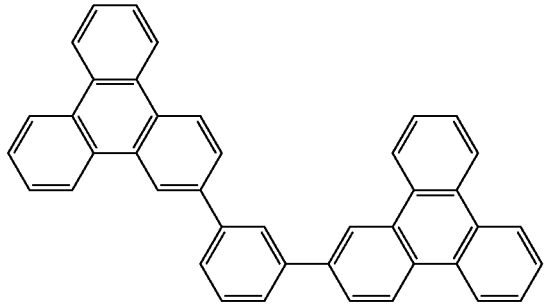 [SMILES: c1cc(-c2ccc3c4ccccc4c4ccccc4c3c2)cc(-c2ccc3c4ccccc4c4ccccc4c3c2)c1] | US20060280965 |
| | 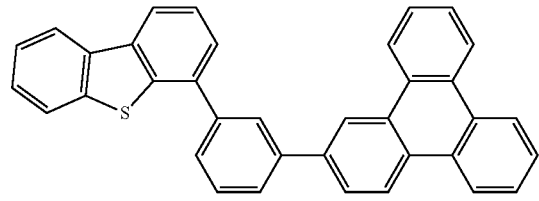 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 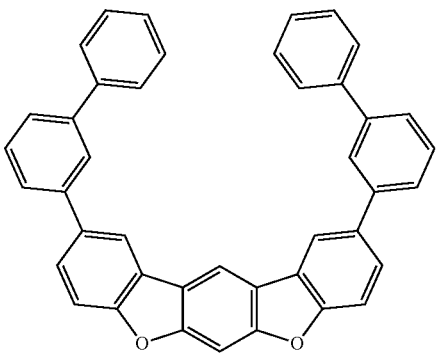 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 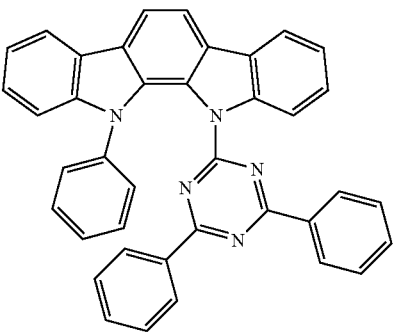 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 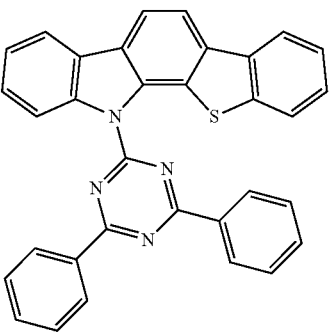 [SMILES: c1ccc(-c2nc(-c3ccccc3)nc(-n3c4ccccc4c4ccc5c6ccccc6sc5c43)n2)cc1] | WO2010107244 |

TABLE 2-continued

| MATERIAL | EXAMPLES OF MATERIAL | PUBLICATIONS |
| --- | --- | --- |
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 2-continued
| MATERIAL | EXAMPLES OF MATERIAL | PUBLICATIONS |
|---|---|---|
| | 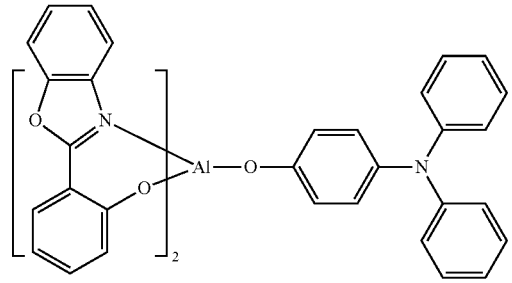 | WO2006132173 |
| | 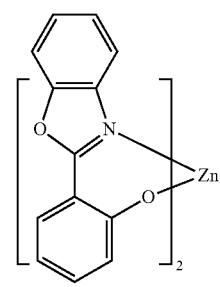 | JP200511610 |
| Spirofluorene-carbazole compounds | 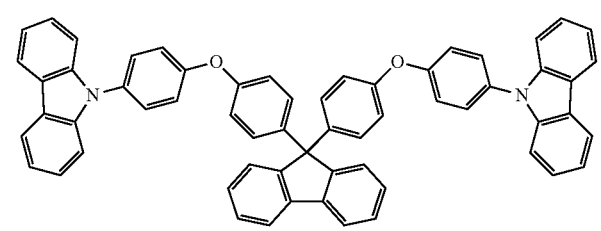 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 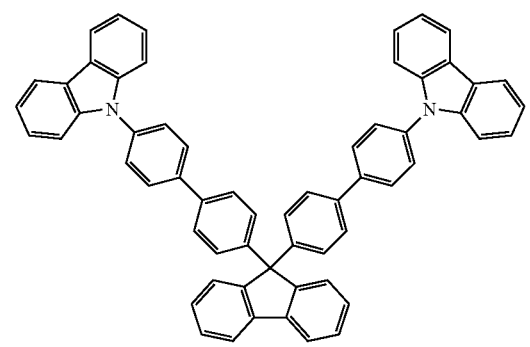 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 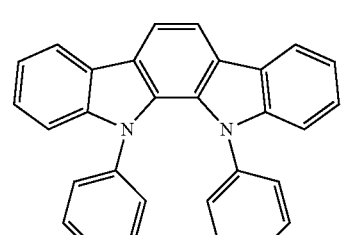 | WO2007063796 |

TABLE 2-continued
| MATERIAL | EXAMPLES OF MATERIAL | PUBLICATIONS |
|---|---|---|
| | 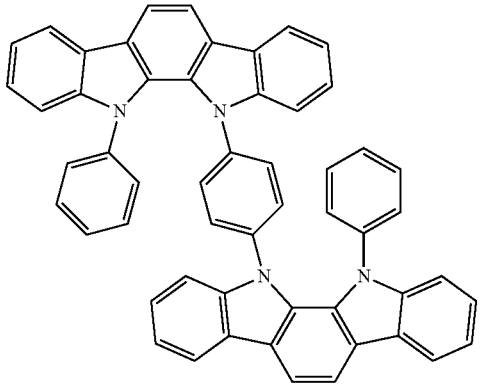 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 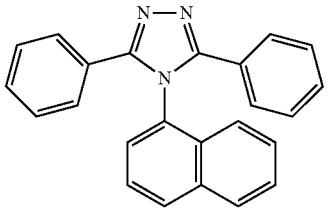 [SMILES: c1ccc(-c2nnc(-c3ccccc3)n2-c2cccc3ccccc23)cc1] | J. Appl. Phys. 90, 5048 (2001) |
| | 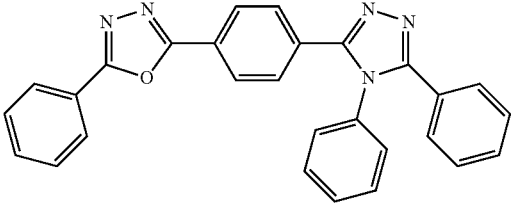 [SMILES: c1ccc(-c2nnc(-c3ccc(-c4nnc(-c5ccccc5)n4-c4ccccc4)cc3)o2)cc1] | WO2004107822 |
| Tetraphenylene complexes | 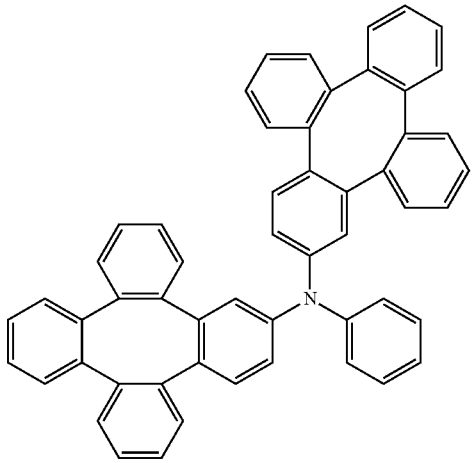 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 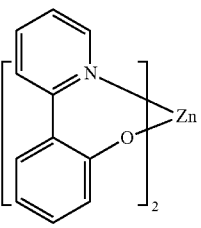 | WO2005030900 |

TABLE 2-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

| MATERIAL | EXAMPLES OF MATERIAL | PUBLICATIONS |
|---|---|---|
| | 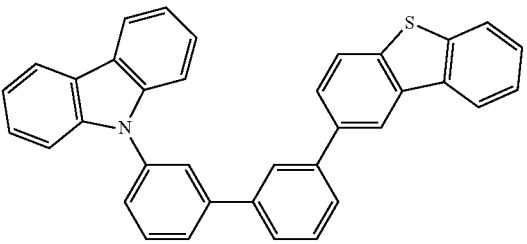 [SMILES: c1cc(-c2cccc(-n3c4ccccc4c4ccccc43)c2)cc(-c2ccc3sc4ccccc4c3c2)c1] | US20090030202, US20090017330 |
| | 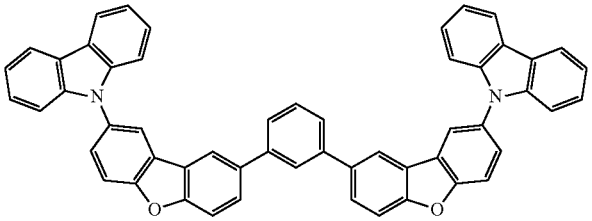 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 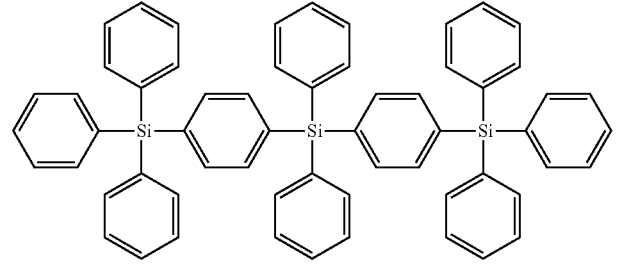 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 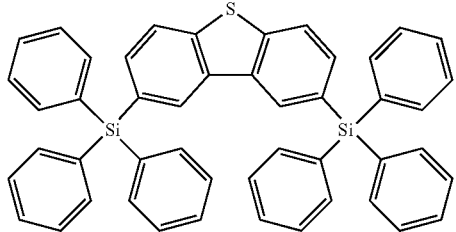 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 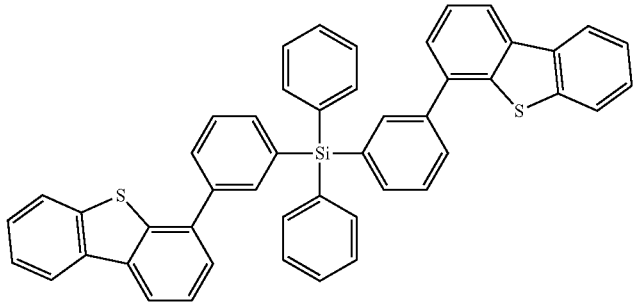 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 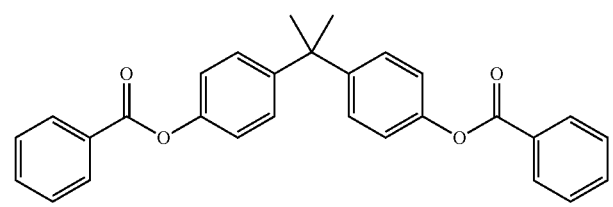 [SMILES: CC(C)(c1ccc(OC(=O)c2ccccc2)cc1)c1ccc(OC(=O)c2ccccc2)cc1] | WO2006100298 |

TABLE 2-continued
| MATERIAL | EXAMPLES OF MATERIAL | PUBLICATIONS |
|---|---|---|
| Carbazole linked by non-conjugated groups | 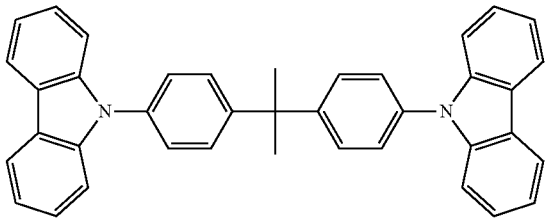 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 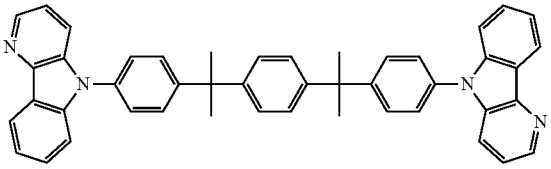 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 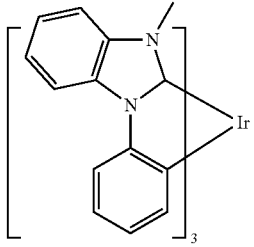 | U.S. Pat. No. 7,154,114 |
Phosphorescent dopants
Red dopants
| | | |
|---|---|---|
| Heavy metal porphyrins (e.g., PtOEP) | 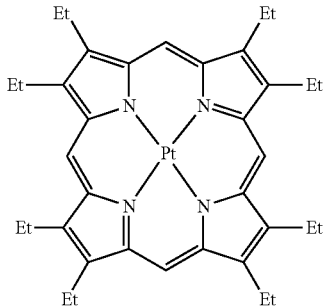 | Nature 395, 151 (1998) |
| Iridium(III) organometallic complexes | 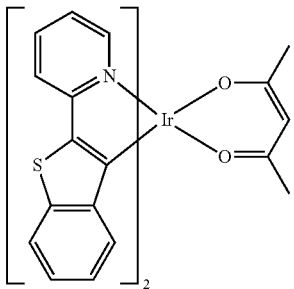 | Appl. Phys. Lett. 78, 1622 (2001) |
| | 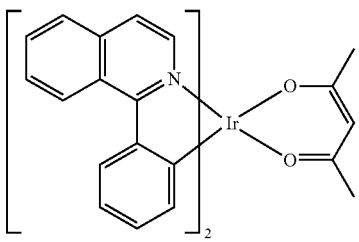 | US2006835469 |

TABLE 2-continued
| MATERIAL | EXAMPLES OF MATERIAL | PUBLICATIONS |
|---|---|---|
| | 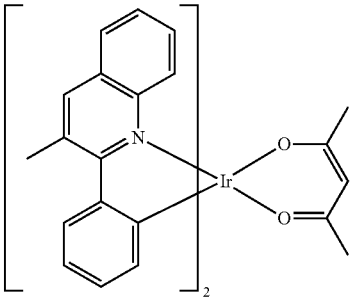 | US2006835469 |
| | 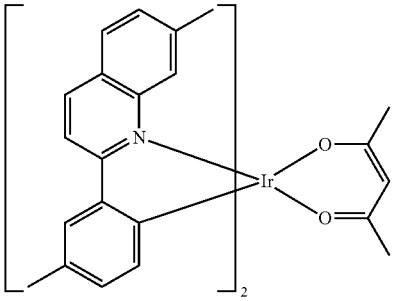 | US20060202194 |
| | 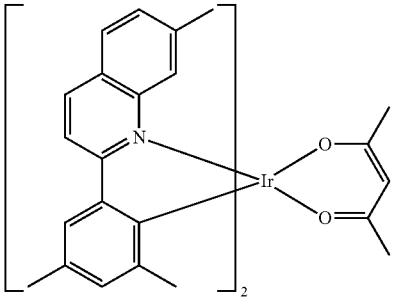 | US20060202194 |
| | 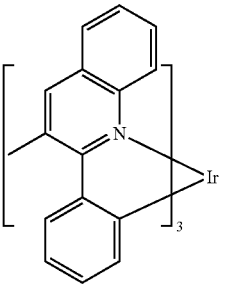 | US20070087321 |
| | 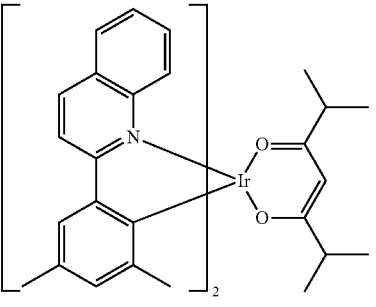 | US20080261076<br>US20100090591 |

TABLE 2-continued

| MATERIAL | EXAMPLES OF MATERIAL | PUBLICATIONS |
|---|---|---|
| | *[Ir complex with isoquinoline-phenyl ligand, tris]* | US20070087321 |
| | *[Ir complex with benzoisoquinoline-phenyl-octyl ligand, tris]* | Adv. Mater. 19, 739 (2007) |
| | *[Ir(acac) complex with methyl-pyrazino-phenanthrene diphenyl ligand, bis]* | WO2009100991 |
| | *[Ir complex with benzotriazole-naphthyl ligand and acac, bis]* | WO2008101842 |
| | *[Ir complex with biphenyl, two PPH₃ and Cl]* | U.S. Pat. No. 7,232,618 |

TABLE 2-continued

| MATERIAL | EXAMPLES OF MATERIAL | PUBLICATIONS |
| --- | --- | --- |
| Platinum(II) organometallic complexes | | WO2003040257 |
| | | US20070103060 |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

TABLE 2-continued
| MATERIAL | EXAMPLES OF MATERIAL | PUBLICATIONS |
| --- | --- | --- |
| | Green dopants | |
| Iridium(III) organometallic complexes | 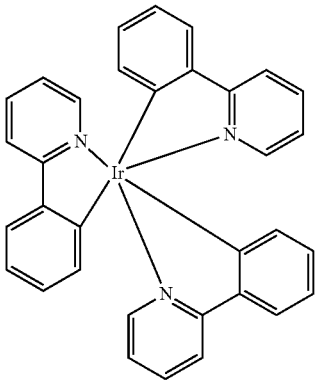 and its derivatives | Inorg. Chem. 40, 1704 (2001) |
| | 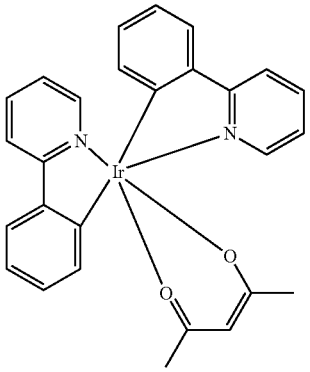 | US20020034656 |
| | 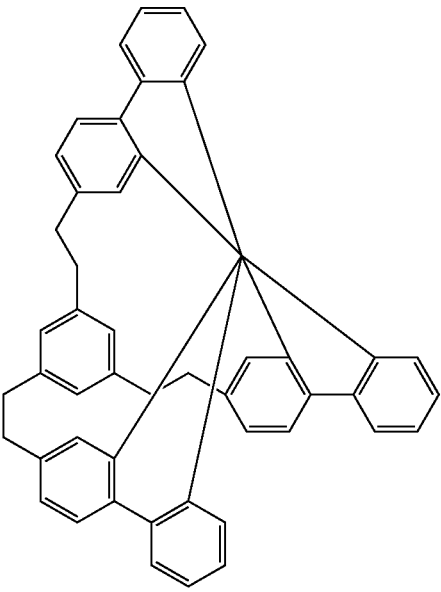 | U.S. Pat. No. 7,332,232 |

TABLE 2-continued

| MATERIAL | EXAMPLES OF MATERIAL | PUBLICATIONS |
|---|---|---|
|  |  | US20090108737 |
|  |  | WO2010028151 |
|  |  | EP1841834B |
|  |  | US20060127696 |
|  |  | US20090039776 |

TABLE 2-continued
| MATERIAL | EXAMPLES OF MATERIAL | PUBLICATIONS |
|---|---|---|
| | 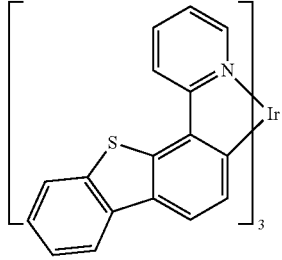 | U.S. Pat. No. 6,921,915 |
| | 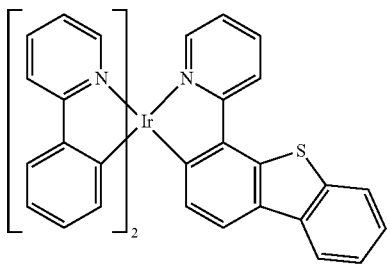 | US20100244004 |
| | 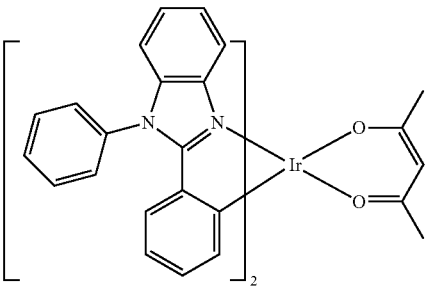 | U.S. Pat. No. 6,687,266 |
| | 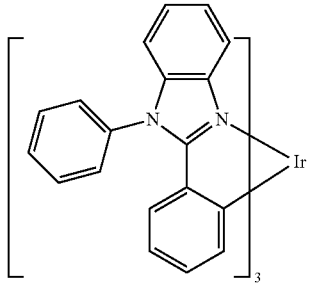 | Chem. Mater. 16, 2480 (2004) |
| | 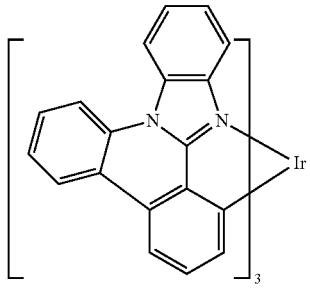 | US20070190359 |

TABLE 2-continued

| MATERIAL | EXAMPLES OF MATERIAL | PUBLICATIONS |
|---|---|---|
| | | US 20060008670
JP2007123392 |
| | | WO2010086089,
WO2011044988 |
| | | Adv. Mater. 16, 2003
(2004) |
| | | Angew. Chem. Int. Ed.
2006, 45, 7800 |
| | | WO2009050290 |
| | | US20090165846 |

TABLE 2-continued
| MATERIAL | EXAMPLES OF MATERIAL | PUBLICATIONS |
|---|---|---|
| | 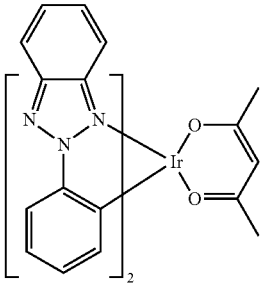 | US20080015355 |
| | 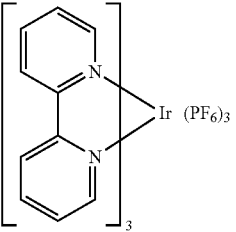 | US20010015432 |
| | 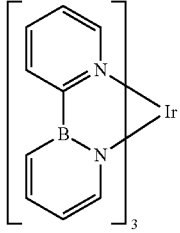 | US20100295032 |
| Monomer for polymeric metal organometallic compounds | 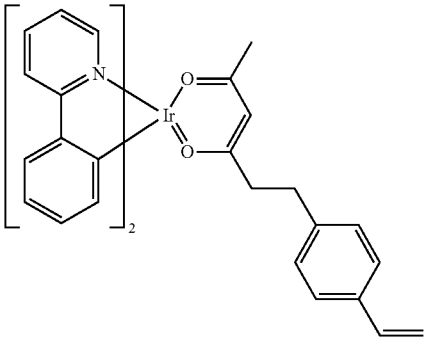 | U.S. Pat. No. 7,250,226, U.S. Pat. No. 7,396,598 |
| Pt(II) organometallic complexes, including polydentated ligands | 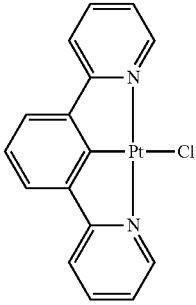 | Appl. Phys. Lett. 86, 153505 (2005) |

TABLE 2-continued
| MATERIAL | EXAMPLES OF MATERIAL | PUBLICATIONS |
|---|---|---|
| | 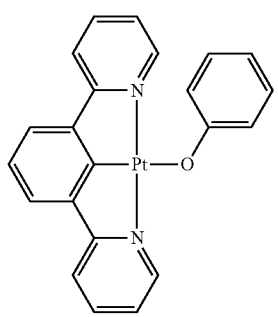 | Appl. Phys. Lett. 86, 153505 (2005) |
| | 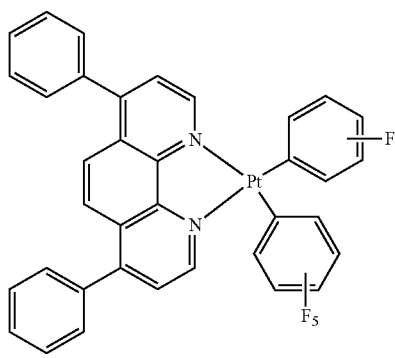 | Chem. Lett. 34, 592 (2005) |
| | 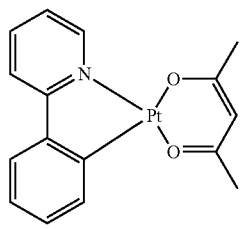 | WO2002015645 |
| | 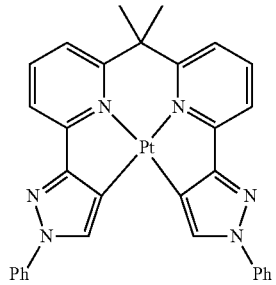 | US20060263635 |
| | 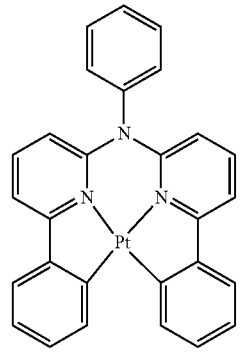 | US20060182992<br>US20070103060 |

TABLE 2-continued
| MATERIAL | EXAMPLES OF MATERIAL | PUBLICATIONS |
|---|---|---|
| Cu complexes | 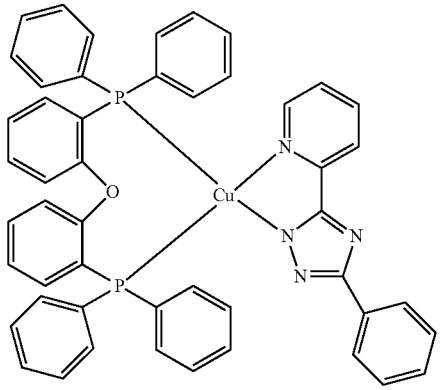 | WO2009000673 |
| | 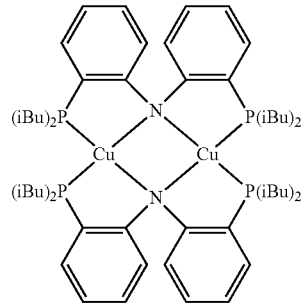 | US20070111026 |
| Gold complexes | 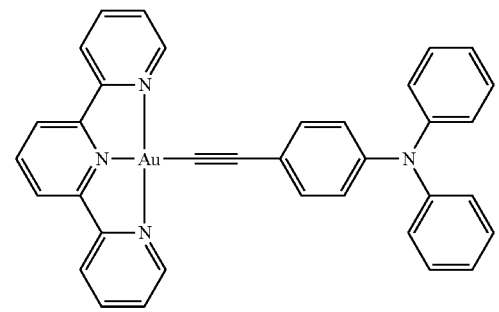 | Chem. Commun. 2906 (2005) |
| Rhenium(III) complexes | 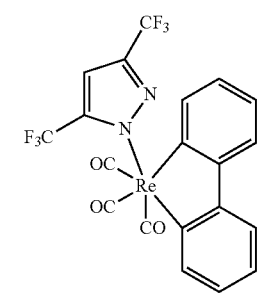 | Inorg. Chem. 42, 1248 (2003) |

TABLE 2-continued

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 2-continued
| MATERIAL | EXAMPLES OF MATERIAL | PUBLICATIONS |
|---|---|---|
| Blue dopants | | |
| Iridium(III) organometallic complexes | 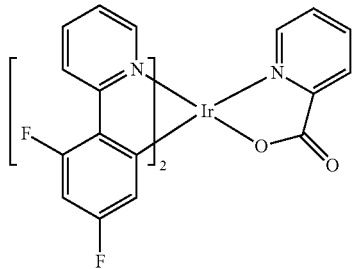 | WO2002002714 |
| | 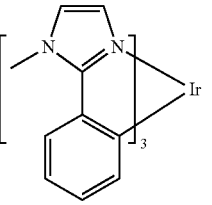 | WO2006009024 |
| | 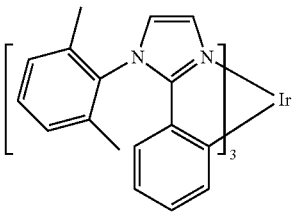 | US20060251923<br>US20110057559<br>US20110204333 |
| | 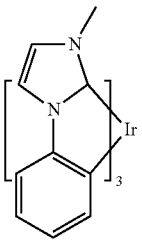 | U.S. Pat.<br>No. 7,393,599,<br>WO2006056418,<br>US20050260441,<br>WO2005019373 |
| | 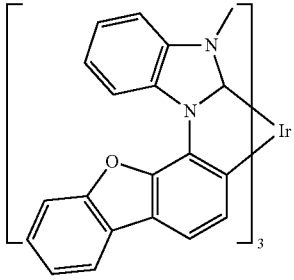 | U.S. Pat.<br>No. 7,534,505 |
| | 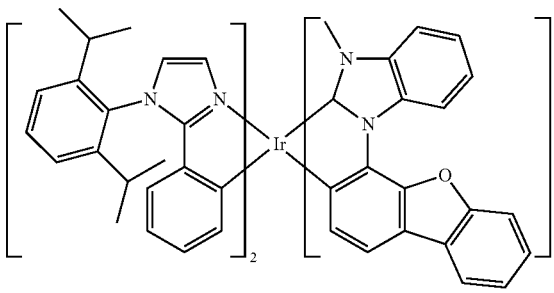 | WO2011051404 |

TABLE 2-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

TABLE 2-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 2-continued
| MATERIAL | EXAMPLES OF MATERIAL | PUBLICATIONS |
|---|---|---|
| | 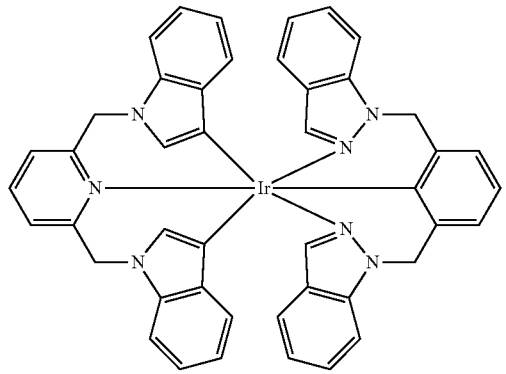 | WO2006082742 |
| Osmium(II) complexes | 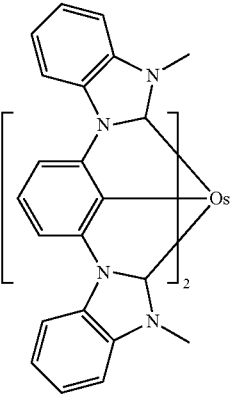 | U.S. Pat. No. 7,279,704 |
| | 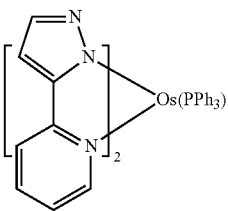 | Organometallics 23, 3745 (2004) |
| Gold complexes | 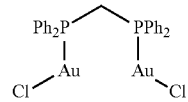 | Appl. Phys. Lett. 74, 1361 (1999) |
| Platinum(II) complexes | 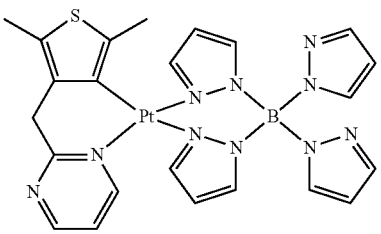 | WO2006098120, WO2006103874 |

TABLE 2-continued

| MATERIAL | EXAMPLES OF MATERIAL | PUBLICATIONS |
|---|---|---|
| Pt tetradentate complexes with at least one metal-carbene bond | 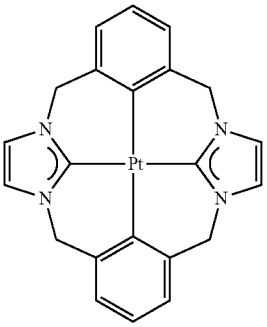 | U.S. Pat. No. 7,655,323 |

Exciton/hole blocking layer materials

| MATERIAL | EXAMPLES OF MATERIAL | PUBLICATIONS |
|---|---|---|
| Bathocuprine compounds (e.g., BCP, BPhen) | 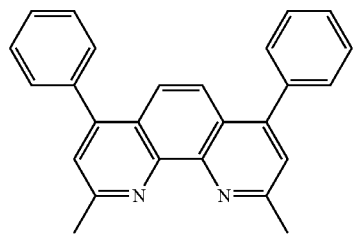 [SMILES: Cc1cc(-c2ccccc2)c2ccc3c(-c4ccccc4)cc(C)nc3c2n1] | Appl. Phys. Lett. 75, 4 (1999) |
| | | Appl. Phys. Lett. 79, 449 (2001) |
| Metal 8-hydroxyquinolates (e.g., BAlq) | 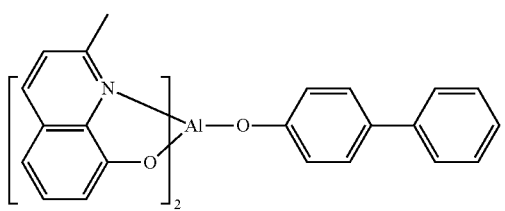 | Appl. Phys. Lett. 81, 162 (2002) |
| 5-member ring electron deficient heterocycles such as triazole, oxadiazole, imidazole, benzoimidazole | 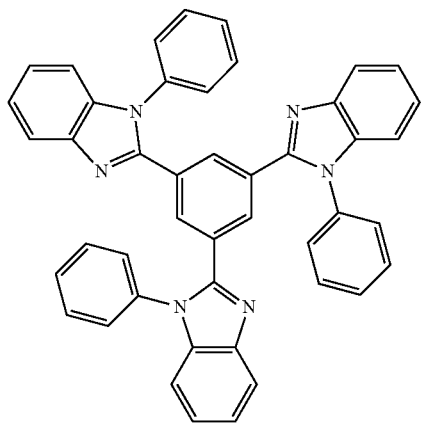 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 2-continued

| MATERIAL | EXAMPLES OF MATERIAL | PUBLICATIONS |
| --- | --- | --- |
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

TABLE 2-continued

| MATERIAL | EXAMPLES OF MATERIAL | PUBLICATIONS |
|---|---|---|
| | Electron transporting materials | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |

TABLE 2-continued

| MATERIAL | EXAMPLES OF MATERIAL | PUBLICATIONS |
|---|---|---|
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 2-continued
| MATERIAL | EXAMPLES OF MATERIAL | PUBLICATIONS |
| --- | --- | --- |
| Silole compounds | 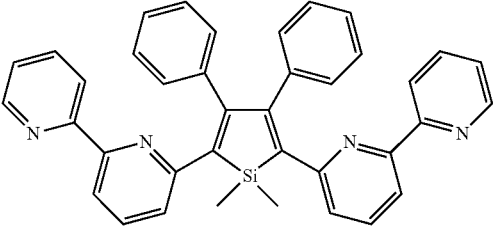 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 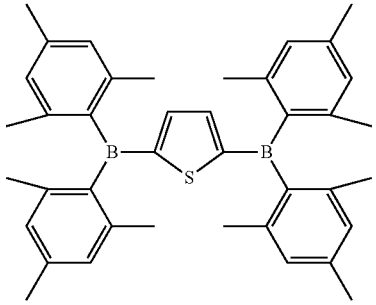 | J. Am. Chem. Soc. 120, 9714 (1998) |
| Fluorinated aromatic compounds | 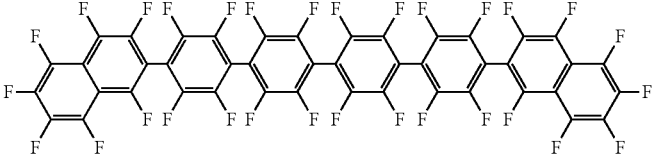 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 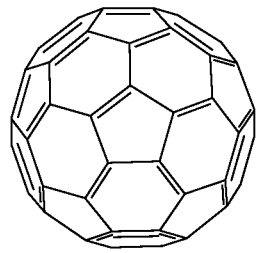 | US20090101870 |
| Triazine complexes | 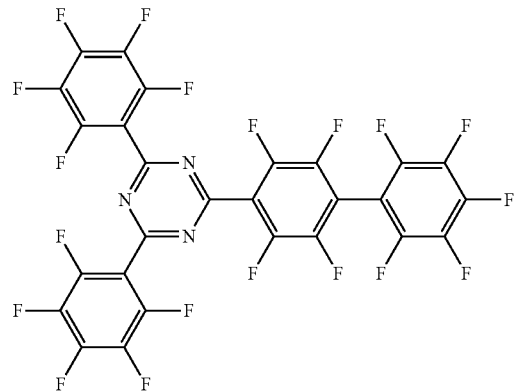 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 2-continued

| MATERIAL | EXAMPLES OF MATERIAL | PUBLICATIONS |
|---|---|---|
| Zn (N^N) complexes | 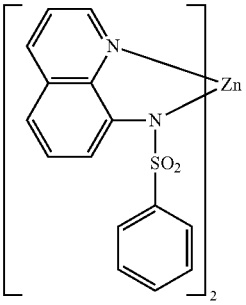 | U.S. Pat. No. 6,528,187 |

EXPERIMENTAL

Example compounds based on the present invention were synthesized according to the following:

Synthesis Examples

Synthesis of N-([1,1'-biphenyl]-4-yl)-[1,1':3',1''-terphenyl]-4'-amine

Xylene (250 mL) was bubbled with nitrogen for 15 min, followed by addition of 2-dicyclohexylphosphino-2',6'-dimethoxybiphenyl (1.8 g, 4.4 mmol) and $Pd_2(dba)_3$ (1.0 g, 1.1 mmol). The mixture was bubbled with nitrogen for 15 min, then [1,1':3',1''-terphenyl]-4'-amine (9.8 g, 40.0 mmol), 4-iodobiphenyl (10.3 g, 36.7 mmol), sodium tert-butoxide (7.0 g, 73.4 mmol) were added. The mixture was bubbled with nitrogen for 15 min and refluxed for 13 h. After cooling, the reaction mixture was filtered through a silica pad and washed with toluene. The solvent was removed in vacuo and the residue was purified by flash chromatography using 40-60% toluene/hexane to afford N-([1,1'-biphenyl]-4-yl)-[1,1':3',1''-terphenyl]-4'-amine (14.7 g, 92% yield) as a white solid.

Synthesis of Compound 5

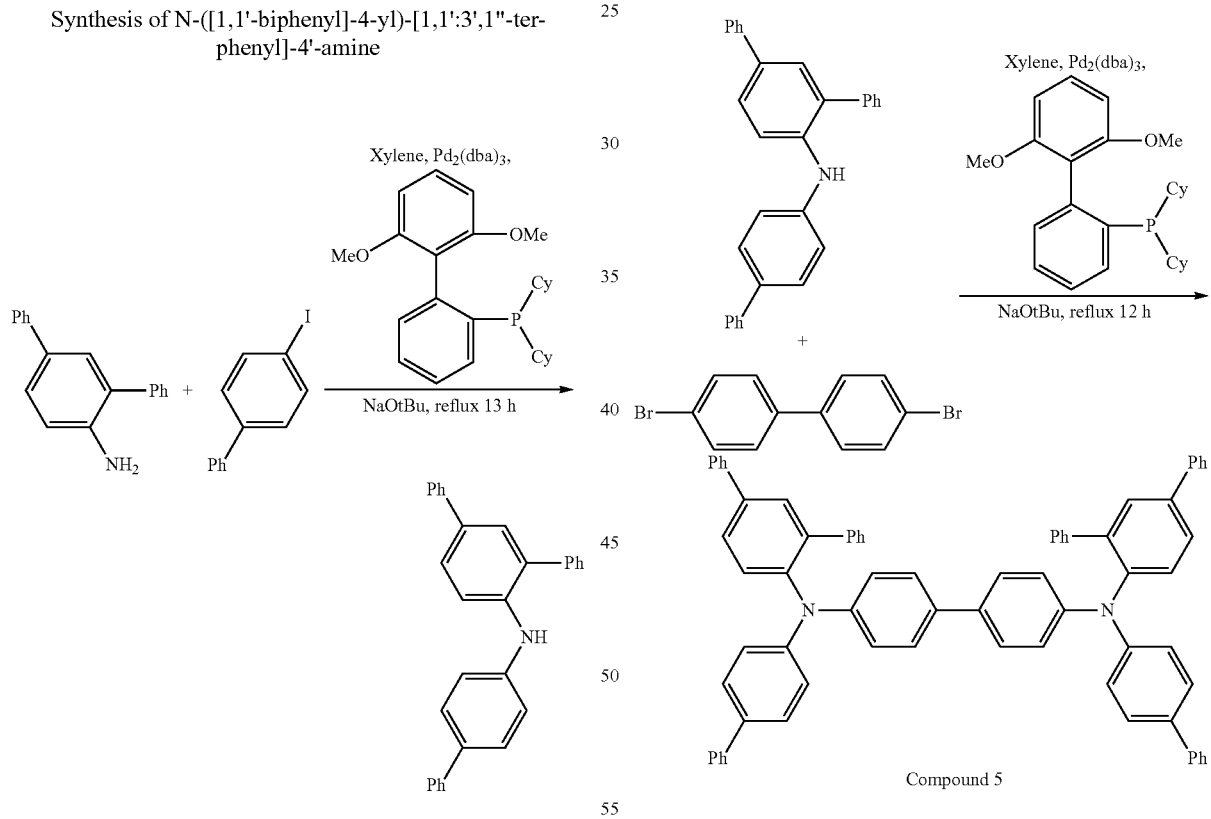

Compound 5

Xylene (125 mL) was bubbled with nitrogen for 15 min, followed by addition of 2-dicyclohexylphosphino-2',6'-dimethoxybiphenyl (0.30 g, 0.72 mmol) and $Pd_2(dba)_3$ (0.16 g, 0.18 mmol). The mixture was bubbled with nitrogen for 15 min, then N-([1,1'-biphenyl]-4-yl)-[1,1':3',1''-terphenyl]-4'-amine (4.0 g, 10.0 mmol), 4,4'-dibromobiphenyl (1.4 g, 4.5 mmol), sodium tert-butoxide (1.7 g, 18.0 mmol) were added. The mixture was bubbled with nitrogen for 15 min and refluxed for 12 h. After cooling, the reaction mixture was filtered through a silica pad and washed with toluene. The solvent was removed in vacuo and the residue was purified by flash chromatography using 40-60% toluene/hexane to afford Compound 5 (4.1 g, 97% yield) as a white solid.

Synthesis of N-([1,1'-biphenyl]-4-yl)-[1,1':3',1''-terphenyl]-2'-amine

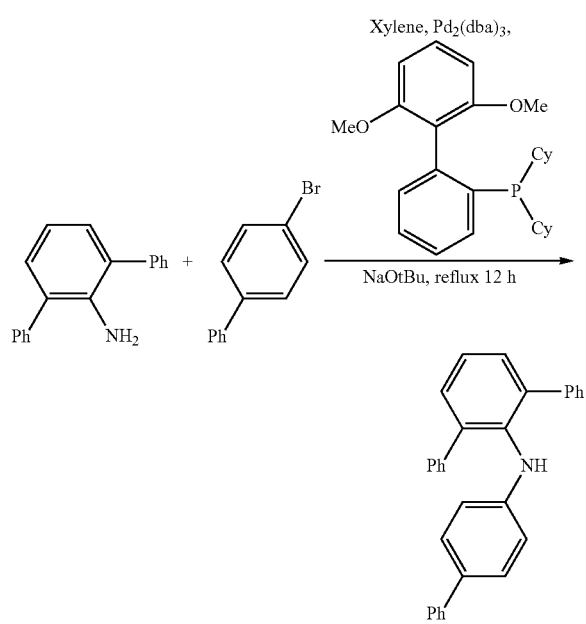

Xylene (250 mL) was bubbled with nitrogen for 15 min, followed by addition of 2-dicyclohexylphosphino-2',6'-dimethoxybiphenyl (4.6 g, 11.2 mmol) and Pd$_2$(dba)$_3$ (2.6 g, 2.8 mmol). The mixture was bubbled with nitrogen for 15 min, then [1,1':3',1''-terphenyl]-2'-amine (13.7 g, 56.0 mmol), 4-bromobiphenyl (13.0 g, 56.0 mmol), sodium tert-butoxide (10.8 g, 112.0 mmol) were added. The mixture was bubbled with nitrogen for 15 min and refluxed for 12 h. After cooling, the reaction mixture was filtered through a silica pad and washed with toluene. The solvent was removed in vacuo and the residue was purified by flash chromatography using 30-40% toluene/hexane to afford N-([1,1'-biphenyl]-4-yl)-[1,1':3',1''-terphenyl]-2'-amine (21.0 g, 93% yield) as a white solid.

Synthesis of N-([1,1'-biphenyl]-4-yl)-N-(4-methoxyphenyl)-[1,1':3',1''-terphenyl]-2'-amine

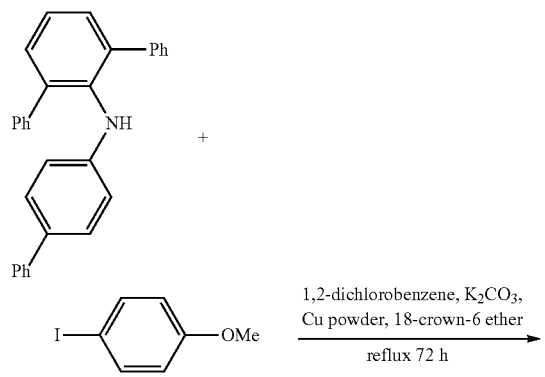

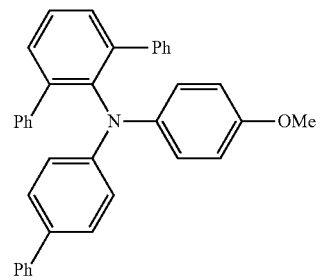

N-([1,1'-biphenyl]-4-yl)[1,1':3',1''-terphenyl]-2'-amine (15.9 g, 40.0 mmol), 4-iodoanisole (37.4 g, 160.0 mmol), potassium carbonate (22.1 g, 160.0 mmol), copper powder (5.1 g, 80.0 mmol), 18-crown-6 ether (21.1 g, 80.0 mmol) and 1,2-dichlorobenzene (200 mL) were bubbled with nitrogen for 30 min. The mixture was refluxed for 72 h. After cooling, the reaction mixture was filtered through a silica pad and washed with toluene (containing 0.5% triethylamine). The solvent was removed in vacuo and the residue was purified by flash chromatography using 40-50% toluene/hexane (containing 0.5% triethylamine) to afford N-([1,1'-biphenyl]-4-yl)-N-(4-methoxyphenyl)-[1,1':3',1''-terphenyl]-2'-amine (10.3 g, 51% yield) as a white solid.

Synthesis of 4-([1,1'-biphenyl]-4-yl([1,1':3',1''-terphenyl]-2'-yl)amino)phenyl Trifluoromethanesulfonate

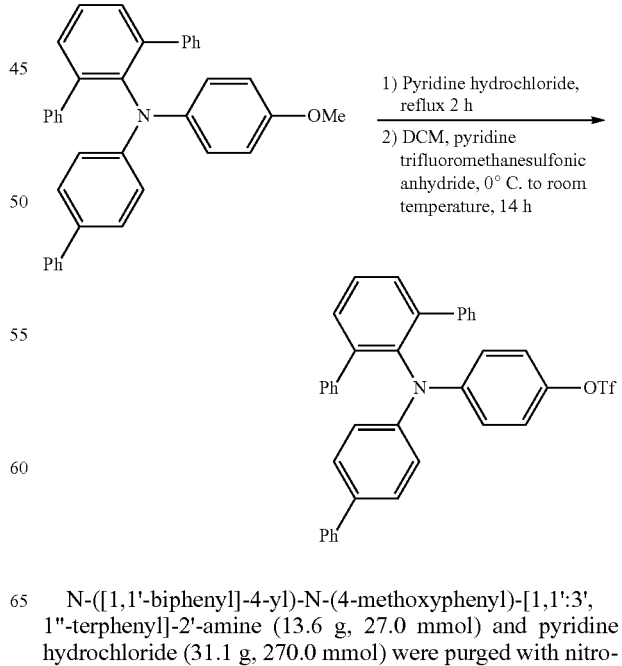

N-([1,1'-biphenyl]-4-yl)-N-(4-methoxyphenyl)-[1,1':3', 1''-terphenyl]-2'-amine (13.6 g, 27.0 mmol) and pyridine hydrochloride (31.1 g, 270.0 mmol) were purged with nitrogen for overnight. The mixture was refluxed for 2 h. After cooling, the precipitate was filtered and washed by excess water. The solid dissolved in DCM was filtered through a silica pad and washed with DCM. The solvent was removed in vacuo. The residue was dissolved in DCM (100 mL) and cooled down to 0° C. After that, pyridine (8.7 mL, 108.0 mmol) and trifluoromethanesulfonic anhydride (9.1 mL, 54.0 mmol) were added at 0 0° C. The mixture was stirred for 14 h from 0° C. to room temperature. The reaction mixture was quenched by the addition of saturated $K_2CO_3$ solution and extracted with DCM. The extracts were dried over $MgSO_4$ and the solvent was removed in vacuo. The residue was purified by re-crystallization in 20% toluene/heptane to afford 4-([1,1'-biphenyl]-4-yl([1,1':3',1"-terphenyl]-2'-yl)amino) phenyl trifluoromethanesulfonate (12.0 g, 72% yield over 2 steps) as a white solid.

Synthesis of N-([1,1'-biphenyl]-4-yl)-N-(4-(4,4,5,5-tetramethyl-1,3,2-dioxaborolan-2-yl)phenyl)-[1,1':3', 1"-terphenyl]-2'-amine 5,5-tetramethyl-1,3,2-dioxaborolan-2-yl)phenyl)-[1,1':3',1"-terphenyl]-2'-amine (1.2 g, 67% yield) as a white solid.

Synthesis of Compound 1

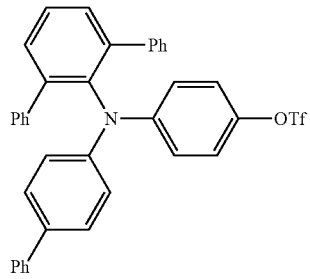

+

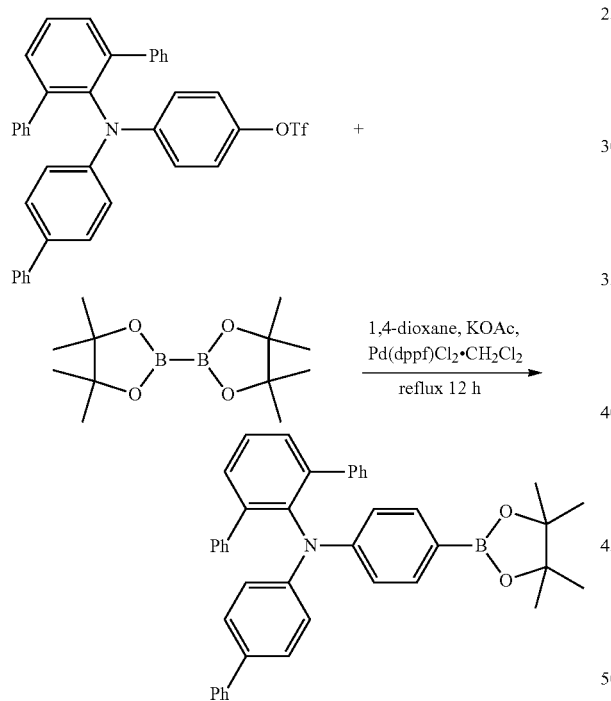

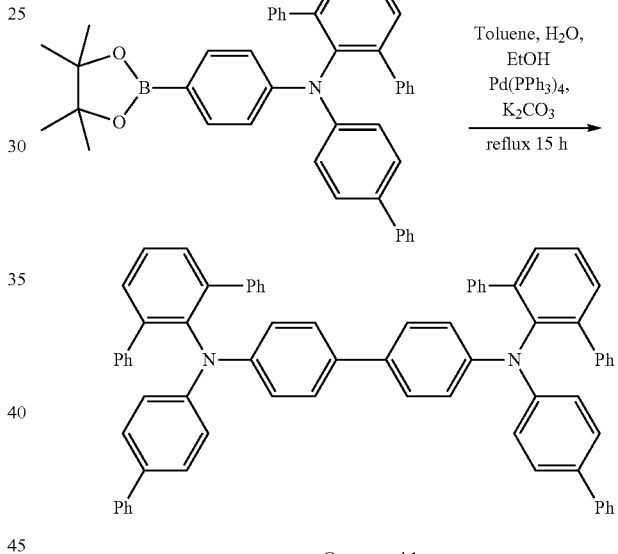

Compound 1

To a solution of 4-([1,1'-biphenyl]-4-yl([1,1':3',1"-terphenyl]-2'-yl)amino)phenyl trifluoromethanesulfonate (1.9 g, 3.0 mmol) in 1,4-dioxane (125 mL) was added bis(pinacolato)diboron (1.5 g, 6.0 mmol), KOAc (0.6 g, 6.0 mmol), and the solution was bubbled with nitrogen for 15 min. Pd(dppf)$Cl_2.CH_2Cl_2$ (0.07 g, 0.09 mmol) was then added to the solution, and the reaction mixture was bubbled with nitrogen for 15 min. The resultant mixture was refluxed for 12 h. After cooling, $H_2O$ (1 mL) was added and stirred for 15 min. The reaction mixture was filtered through a silica pad and washed with toluene (containing 0.5% triethylamine). The solvent was removed in vacuo and the residue was purified by flash chromatography using 75% toluene/hexane (containing 0.5% triethylamine) to afford N-([1,1'-biphenyl]-4-yl)-N-(4-(4,4, To a solution of 4-([1,1'-biphenyl]-4-yl([1,1':3',1"-terphenyl]-2'-yl)amino)phenyl trifluoromethanesulfonate (1.9 g, 3.0 mmol), N-([1,1'-biphenyl]-4-yl)-N-(4-(4,4,5,5-tetramethyl-1,3,2-dioxaborolan-2-yl)phenyl)-[1,1':3',1"-terphenyl]-2'-amine (1.9 g, 3.2 mmol), $Na_2CO_3$ (3.2 g, 30.0 mmol) in toluene (30 mL), water (10 mL) and EtOH (10 mL) was bubbled with nitrogen for 30 min. Pd(PPh$_3$)$_4$ (0.14 g, 0.12 mmol) was added. The mixture was bubbled with nitrogen for 15 min. The resultant mixture was refluxed for 15 h. After cooling, the reaction mixture was extracted by toluene (containing 0.5% triethylamine). The extracts were filtered through a silica pad and washed with toluene (containing 0.5% triethylamine). The solvent was removed in vacuo and the residue was purified by re-crystallization in toluene to afford Compound 1 (1.6 g, 56% yield) as a white solid.

Synthesis of Compound 3

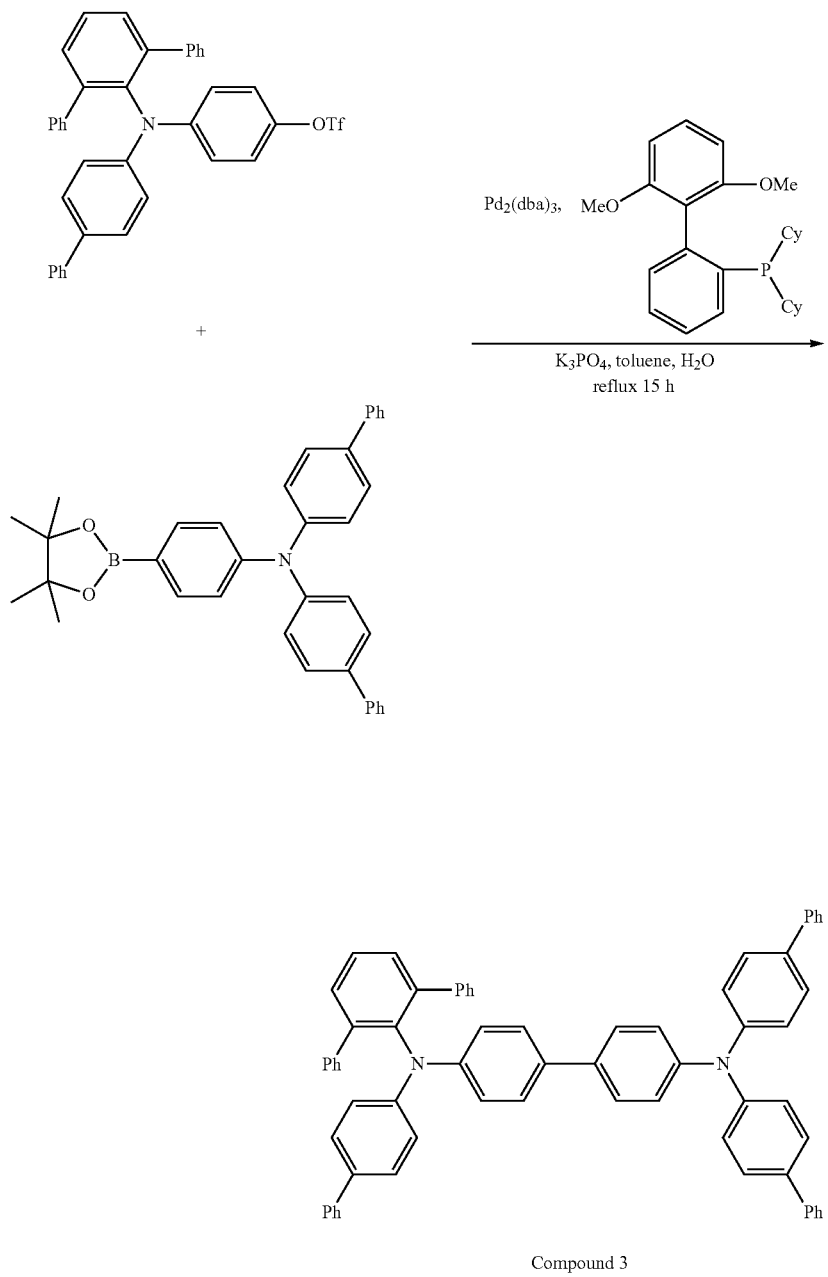

Compound 3

To a solution of 4-([1,1'-biphenyl]-4-yl([1,1':3',1''-terphenyl]-2'-yl)amino)phenyl trifluoromethanesulfonate (3.1 g, 5.0 mmol), N-([1,1'-biphenyl]-4-yl)-N-(4-(4,4,5,5-tetramethyl-1,3,2-dioxaborolan-2-yl)phenyl)-[1,1'-biphenyl]-4-amine (3.4 g, 6.5 mmol), 2-dicyclohexylphosphino-2',6'-dimethoxybiphenyl (0.3 g, 0.6 mmol), $K_3PO_4$ (6.4 g, 30.0 mmol) in toluene (60 mL) and water (6 mL) was bubbled with nitrogen for 30 min. $Pd_2(dba)_3$ (0.14 g, 0.15 mmol) was added. The mixture was bubbled with nitrogen for 15 min. The resultant mixture was refluxed for 15 h. After cooling, the reaction mixture was extracted by toluene (containing 0.5% triethylamine). The extracts were filtered through a silica pad and washed with toluene (containing 0.5% triethylamine). The solvent was removed in vacuo and the residue was purified by flash chromatography using 20-60% toluene/hexane (containing 0.5% triethylamine) to afford Compound 3 (2.6 g, 61% yield) as a white solid.

Synthesis of N-([1,1'-biphenyl]-4-yl)-[1,1'-biphenyl]-2-amine

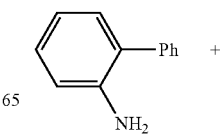

-continued

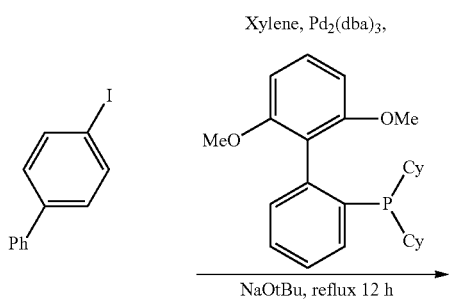

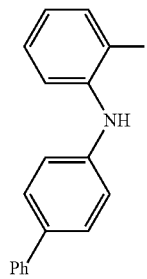

Xylene (250 mL) was bubbled with nitrogen for 15 min, followed by addition of 2-dicyclohexylphosphino-2',6'-dimethoxybiphenyl (3.0 g, 7.2 mmol) and Pd₂(dba)₃ (1.6 g, 1.8 mmol). The mixture was bubbled with nitrogen for 15 min, then [1,1'-biphenyl]-2-amine (10.1 g, 60.0 mmol), 4-iodobiphenyl (16.8 g, 60.0 mmol), sodium tert-butoxide (11.5 g, 120.0 mmol) were added. The mixture was bubbled with nitrogen for 15 min and refluxed for 12 h. After cooling, the reaction mixture was filtered through a silica pad and washed with toluene. The solvent was removed in vacuo and the residue was purified by flash chromatography using 30% toluene/hexane to afford N-([1,1'-biphenyl]-4-yl)-[1,1'-biphenyl]-2-amine (18.3 g, 95% yield) as a white solid.

Synthesis of N-([1,1'-biphenyl]-4-yl)-N-(4-bromophenyl)-[1,1'-biphenyl]-2-amine

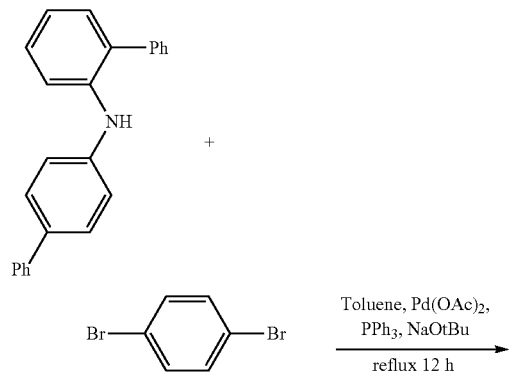

-continued

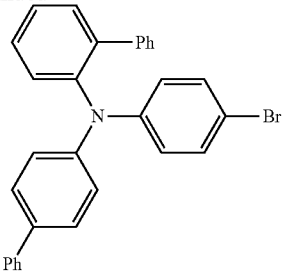

Toluene (500 mL) was bubbled with nitrogen for 15 min, followed by addition of triphenylphosphine (0.4 g, 1.7 mmol) and Pd(OAc)₂ (0.10 g, 0.42 mmol). The mixture was bubbled with nitrogen for 15 min, then N-([1,1'-biphenyl]-4-yl)-[1,1'-biphenyl]-2-amine (6.7 g, 21.0 mmol), 1,4-dibromobenzene (14.9 g, 63.0 mmol), sodium tert-butoxide (4.0 g, 42.0 mmol) were added. The mixture was bubbled with nitrogen for 15 min and refluxed for 12 h. After cooling, the reaction mixture was filtered through a silica pad and washed with toluene (containing 0.5% triethylamine). The solvent was removed in vacuo and the residue was purified by flash chromatography using 10-20% toluene/hexane (containing 0.5% triethylamine) to afford N-([1,1'-biphenyl]-4-yl)-N-(4-bromophenyl)-[1,1'-biphenyl]-2-amine (8.7 g, 87% yield) as a white solid.

Synthesis of N-([1,1'-biphenyl]-4-yl)-N-(4-(4,4,5,5-tetramethyl-1,3,2-dioxaborolan-2-yl)phenyl)-[1,1'-biphenyl]-2-amine

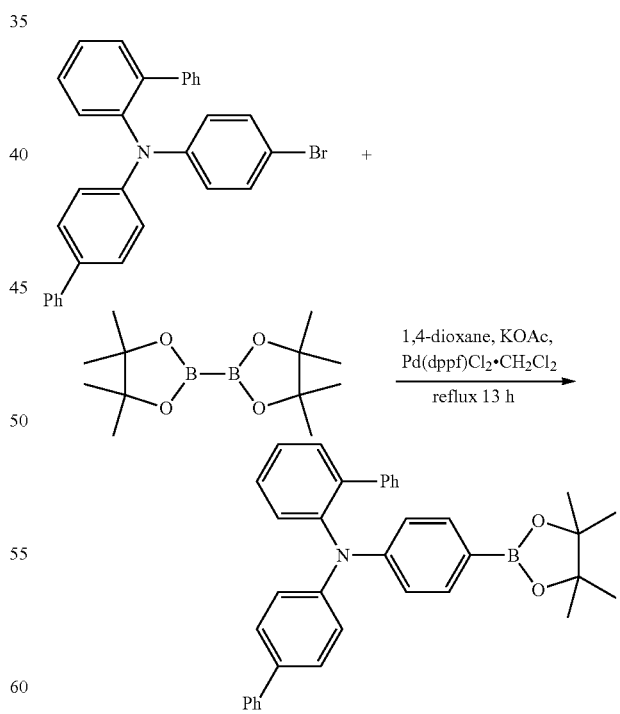

To a solution of N-([1,1'-biphenyl]-4-yl)-N-(4-bromophenyl)-[1,1'-biphenyl]-2-amine (7.1 g, 15.0 mmol) in 1,4-dioxane (125 mL) was added bis(pinacolato)diboron (9.5 g, 37.5 mmol), KOAc (3.7 g, 37.5 mmol), and the solution was bubbled with nitrogen for 15 min. Pd(dppf)Cl₂·CH₂Cl₂ (0.4 g, 0.5 mmol) was then added to the solution, and the reaction mixture was bubbled with nitrogen for 15 min. The resultant mixture was refluxed for 13 h. After cooling, H₂O (3 mL) was added and stirred for 15 min. The reaction mixture was filtered through a silica pad and washed with toluene (containing 0.5% triethylamine). The solvent was removed in vacuo and the residue was purified by flash chromatography using 60% toluene/hexane (containing 0.5% triethylamine) to afford N-([1,1'-biphenyl]-4-yl)-N-(4-(4,4,5,5-tetramethyl-1,3,2-dioxaborolan-2-yl)phenyl)-[1,1'-biphenyl]-2-amine (3.9 g, 49% yield) as a white solid.

Synthesis of Compound 11

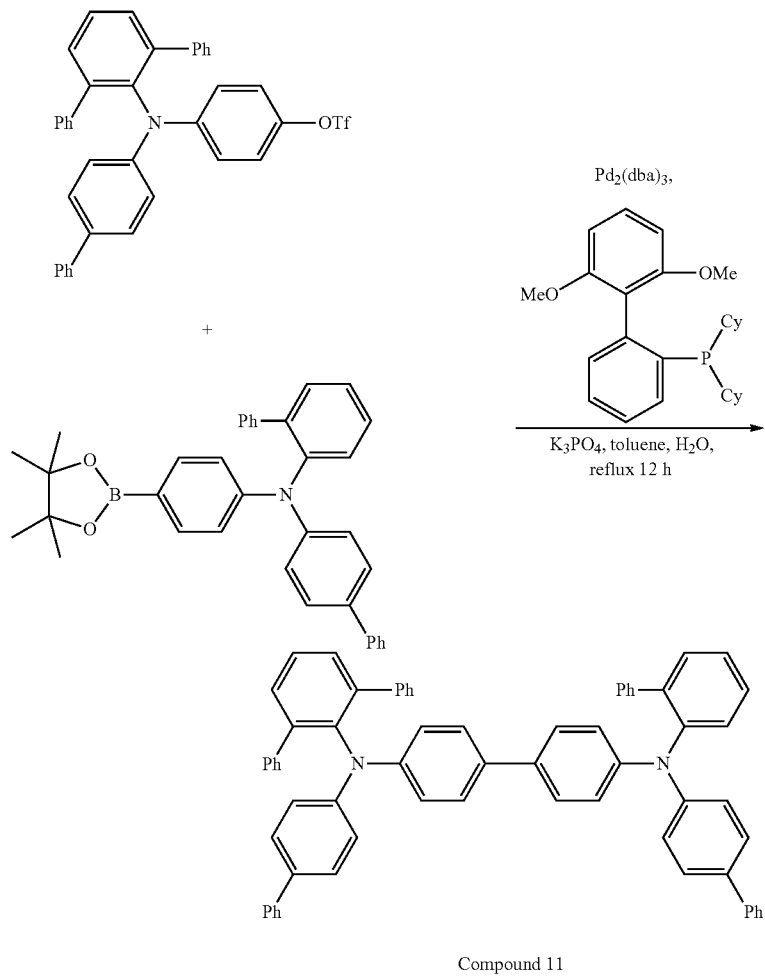

Compound 11

To a solution of 4-([1,1'-biphenyl]-4-yl([1,1':3',1''-terphenyl]-2'-yl)amino)phenyl trifluoromethanesulfonate (0.8 g, 1.3 mmol), N-([1,1'-biphenyl]-4-yl)-N-(4-(4,4,5,5-tetramethyl-1,3,2-dioxaborolan-2-yl)phenyl)-[1,1'-biphenyl]-2-amine (0.8 g, 1.5 mmol), 2-dicyclohexylphosphino-2',6'-dimethoxybiphenyl (0.06 g, 0.15 mmol), K₃PO₄ (1.6 g, 7.5 mmol) in toluene (30 mL) and water (3 mL) was bubbled with nitrogen for 30 min. Pd₂(dba)₃ (0.03 g, 0.03 mmol) was added. The mixture was bubbled with nitrogen for 15 min. The resultant mixture was refluxed for 12 h. The reaction mixture was filtered through a silica pad and washed with toluene (containing 0.5% triethylamine). The solvent was removed in vacuo and the residue was purified by flash chromatography using 20-40% toluene/hexane (containing 0.5% triethylamine) to afford Compound 11 (0.9 g, 82% yield) as a white solid.

Synthesis of N-([1,1'-biphenyl]-4-yl)-N-(4'-bromo-[1,1'-biphenyl]-4-yl)-[1,1'-biphenyl]-2-amine

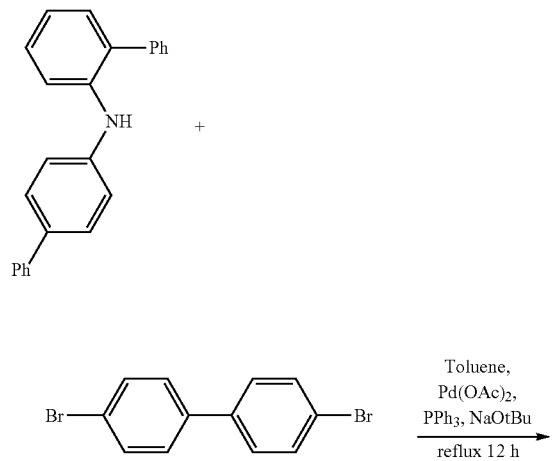

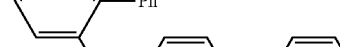

Toluene (250 mL) was bubbled with nitrogen for 15 min, followed by addition of triphenylphosphine (0.2 g, 0.8 mmol) and Pd(OAc)$_2$ (0.05 g, 0.2 mmol). The mixture was bubbled with nitrogen for 15 min, then N-([1,1'-biphenyl]-4-yl)-[1,1'-biphenyl]-2-amine (3.4 g, 10.5 mmol), 4,4'-dibromobiphenyl (6.6 g, 21.0 mmol), sodium tert-butoxide (2.0 g, 21.0 mmol) were added. The mixture was bubbled with nitrogen for 15 min and refluxed for 12 h. After cooling, the reaction mixture was filtered through a silica pad and washed with toluene. The solvent was removed in vacuo and the residue was purified by flash chromatography using 20% toluene/hexane to afford N-([1,1'-biphenyl]-4-yl)-N-(4'-bromo-[1,1'-biphenyl]-4-yl)-[1,1'-biphenyl]-2-amine (4.2 g, 73% yield) as a white solid.

Synthesis of Compound 9

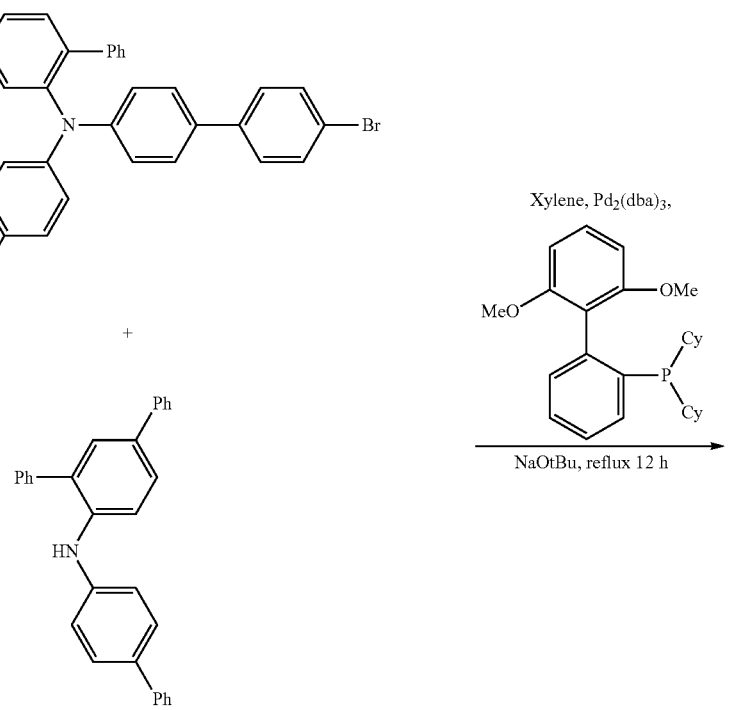

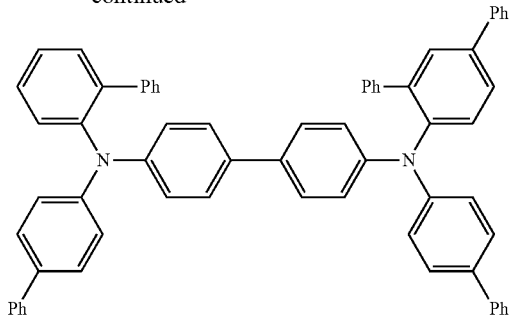

Compound 9

Xylene (125 mL) was bubbled with nitrogen for 15 min, followed by addition of 2-dicyclohexylphosphino-2',6'-dimethoxybiphenyl (0.2 g, 0.4 mmol) and Pd$_2$(dba)$_3$ (0.10 g, 0.11 mmol). The mixture was bubbled with nitrogen for 15 min, then N-([1,1'-biphenyl]-4-yl)-[1,1':3',1''-terphenyl]-4'-amine (1.4 g, 3.6 mmol), N-([1,1'-biphenyl]-4-yl)-N-(4'-bromo-[1,1'-biphenyl]-4-yl)-[1,1'-biphenyl]-2-amine (2.6 g, 4.7 mmol), sodium tert-butoxide (0.7 g, 7.2 mmol) were added. The mixture was bubbled with nitrogen for 15 min and refluxed for 12 h. After cooling, the reaction mixture was filtered through a silica pad and washed with toluene (containing 0.3% triethylamine). The solvent was removed in vacuo and the residue was purified by flash chromatography using 35% toluene/hexane (containing 0.3% triethylamine) to afford Compound 9 (3.1 g, 100% yield) as a white solid.

Synthesis of N-([1,1'-biphenyl]-4-yl)-N-(4-methoxyphenyl)-[1,1':3',1''-terphenyl]-4'-amine

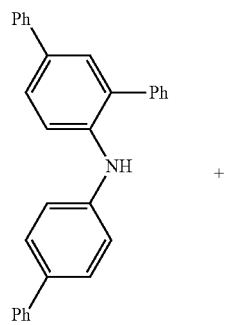

+

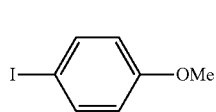

Toluene, Pd$_2$(dba)$_3$,
10% t-Bu$_3$P in
hexane NaOtBu,
rt, 16 h
→

-continued

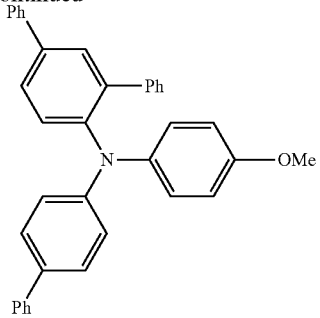

Toluene (200 mL) was bubbled with nitrogen for 15 min, followed by addition of 10% t-Bu$_3$P in hexane (2.9 mL, 1.0 mmol) and Pd$_2$(dba)$_3$ (1.1 g, 1.2 mmol). The mixture was bubbled with nitrogen for 15 min, then N-([1,1'-biphenyl]-4-yl)-[1,1':3',1''-terphenyl]-4'-amine (10.6 g, 26.5 mmol), 4-iodoanisole (11.2 g, 48.0 mmol), sodium tert-butoxide (3.5 g, 36.0 mmol) were added. The mixture was bubbled with nitrogen for 15 min and stirred for 16 h at room temperature. The reaction mixture was filtered through a silica pad and washed with toluene (containing 0.5% triethylamine). The solvent was removed in vacuo and the residue was purified by flash chromatography using 30-40% toluene/hexane (containing 0.5% triethylamine) to afford N-([1,1'-biphenyl]-4-yl)-N-(4-methoxyphenyl)-[1,1':3',1''-terphenyl]-4'-amine (12.5 g, 94% yield) as a white solid.

Synthesis of 4-([1,1'-biphenyl]-4-yl([1,1':3',1''-terphenyl]-4'-yl)amino)phenyl trifluoromethanesulfonate

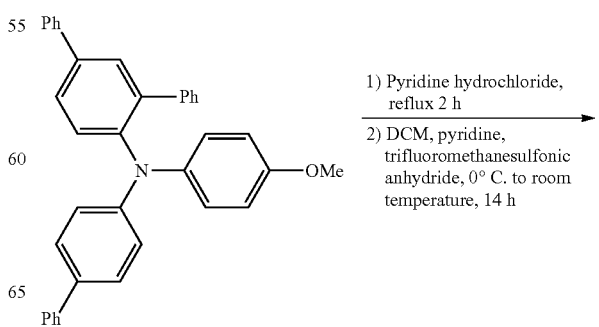

1) Pyridine hydrochloride, reflux 2 h
2) DCM, pyridine, trifluoromethanesulfonic anhydride, 0° C. to room temperature, 14 h
→

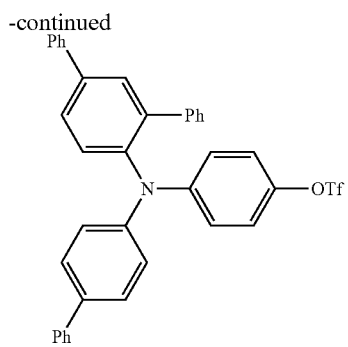

N-([1,1'-biphenyl]-4-yl)-N-(4-methoxyphenyl)-[1,1':3',1"-terphenyl]-4'-amine (12.4 g, 24.7 mmol) and pyridine hydrochloride (28.8 g, 250.0 mmol) were purged with nitrogen for overnight. The mixture was refluxed for 2 h. After cooling, the precipitate was filtered and washed by excess water. The solid dissolved in DCM was filtered through a silica pad and washed with DCM. The solvent was removed in vacuo. The residue was dissolved in DCM (100 mL) and cooled down to 0° C. After that, pyridine (8.1 mL, 100.0 mmol) and trifluoromethanesulfonic anhydride (8.4 mL, 50.0 mmol) were added at 0° C. The mixture was stirred for 17 h from 0° C. to room temperature. The reaction mixture was quenched by the addition of saturated $K_2CO_3$ solution and extracted with DCM. The extracts were dried over $MgSO_4$ and the solvent was removed in vacuo and the residue was purified by flash chromatography using 15% toluene/hexane (containing 0.5% triethylamine) to afford 4-([1,1'-biphenyl]-4-yl([1,1':3',1"-terphenyl]-4'-yl)amino)phenyl trifluoromethanesulfonate (14.5 g, 95% yield) as a white solid.

Synthesis of Compound 7

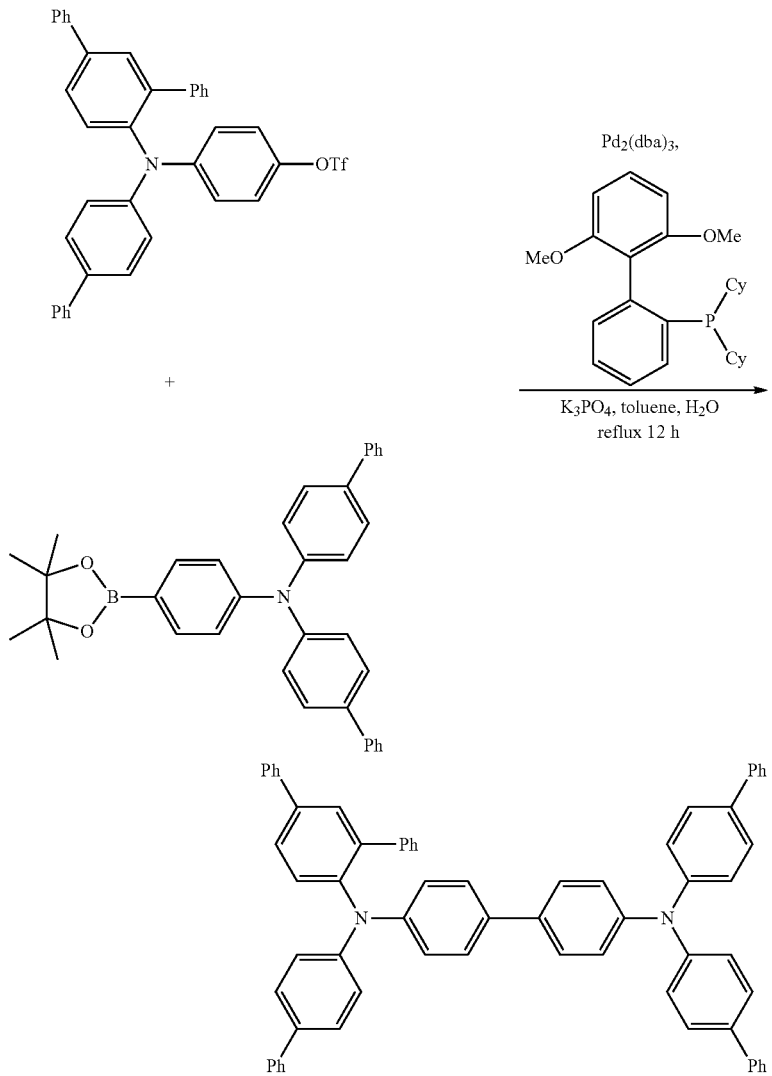

Compound 7

To a solution of 4-([1,1'-biphenyl]-4-yl([1,1':3',1''-terphenyl]-4'-yl)amino)phenyl trifluoromethanesulfonate (2.9 g, 4.7 mmol), N-([1,1'-biphenyl]-4-yl)-N-(4-(4,4,5,5-tetramethyl-1,3,2-dioxaborolan-2-yl)phenyl)-[1,1'-biphenyl]-4-amine (2.9 g, 5.5 mmol), 2-dicyclohexylphosphino-2',6'-dimethoxybiphenyl (0.20 g, 0.48 mmol), K$_3$PO$_4$ (5.1 g, 24.0 mmol) in toluene (40 mL) and water (4 mL) was bubbled with nitrogen for 30 min. Pd$_2$(dba)$_3$ (0.11 g, 0.12 mmol) was added. The mixture was bubbled with nitrogen for 15 min. The resultant mixture was refluxed for 12 h. The reaction mixture was filtered through a silica pad and washed with toluene (containing 1% triethylamine). The solvent was removed in vacuo and the residue was purified by flash chromatography using 40-50% toluene/hexane (containing 1% triethylamine) to afford Compound 7 (4.1 g, 99% yield) as a white solid.

Synthesis of N-([1,1'-biphenyl]-4-yl)-N-(4-(4,4,5,5-tetramethyl-1,3,2-dioxaborolan-2-yl)phenyl)-[1,1':3',1''-terphenyl]-4'-amine

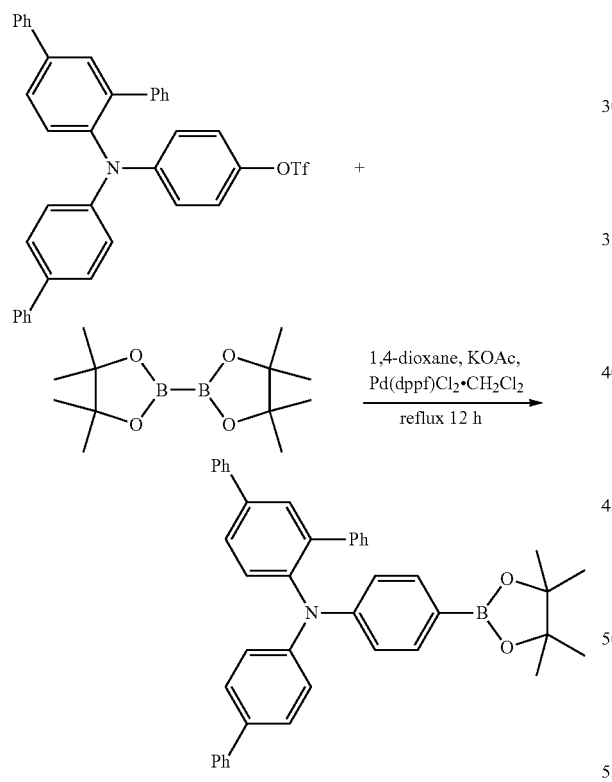

To a solution of 4-([1,1'-biphenyl]-4-yl([1,1':3',1''-terphenyl]-4'-yl)amino)phenyl trifluoromethanesulfonate (6.2 g, 10.0 mmol) in 1,4-dioxane (60 mL) was added bis(pinacolato)diboron (6.4 g, 25.0 mmol), KOAc (2.5 g, 25.0 mmol), and the solution was bubbled with nitrogen for 15 min. Pd(dppf)Cl$_2$.CH$_2$Cl$_2$ (0.25 g, 0.30 mmol) was then added to the solution, and the reaction mixture was bubbled with nitrogen for 15 min. The resultant mixture was refluxed for 12 h. After cooling, H$_2$O (2 mL) was added and stirred for 15 min. The reaction mixture was filtered through a silica pad and washed with toluene (containing 1% triethylamine). The solvent was removed in vacuo and the residue was purified by flash chromatography using 60% toluene/hexane (containing 1% triethylamine) to afford N-([1,1'-biphenyl]-4-yl)-N-(4-(4,4,5,5-tetramethyl-1,3,2-dioxaborolan-2-yl)phenyl)-[1,1':3',1''-terphenyl]-4'-amine (5.4 g, 90% yield) as a white solid.

Synthesis of Compound 14

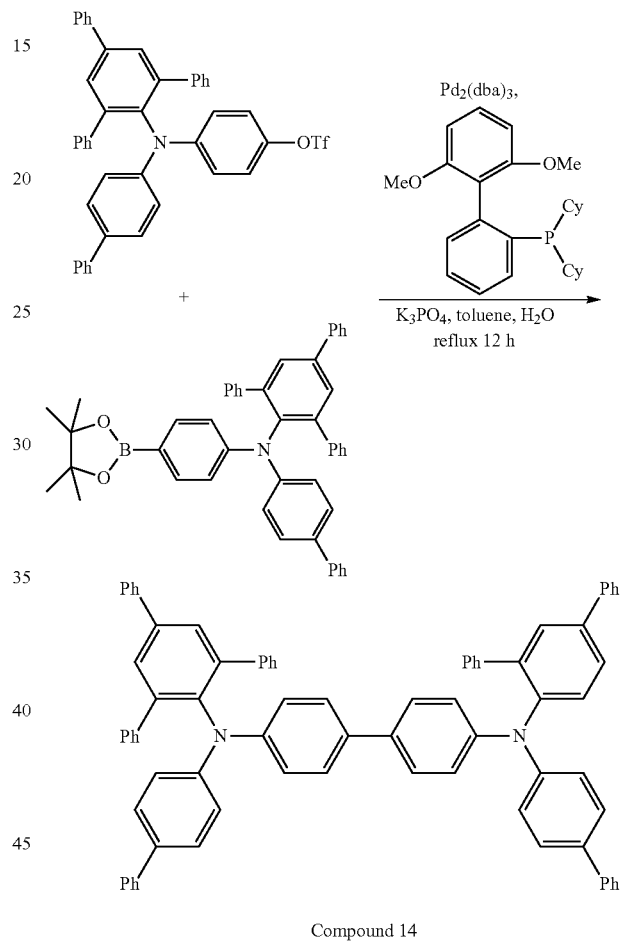

Compound 14

To a solution of 4-([1,1'-biphenyl]-4-yl(5'-phenyl-[1,1':3',1''-terphenyl]-4'-yl)amino)phenyl trifluoromethanesulfonate (2.4 g, 3.5 mmol), N-([1,1'-biphenyl]-4-yl)-N-(4-(4,4,5,5-tetramethyl-1,3,2-dioxaborolan-2-yl)phenyl)-[1,1':3',1''-terphenyl]-4'-amine (2.3 g, 3.9 mmol), 2-dicyclohexylphosphino-2',6'-dimethoxybiphenyl (0.17 g, 0.42 mmol), K$_3$PO$_4$ (4.5 g, 21.0 mmol) in toluene (50 mL) and water (5 mL) was bubbled with nitrogen for 30 min. Pd$_2$(dba)$_3$ (0.10 g, 0.11 mmol) was added. The mixture was bubbled with nitrogen for 15 min. The resultant mixture was refluxed for 12 h. The reaction mixture was filtered through a silica pad and washed with toluene (containing 1% triethylamine). The solvent was removed in vacuo and the residue was purified by flash chromatography using 25-40% toluene/hexane (containing 1% triethylamine) to afford Compound 14 (2.0 g, 57% yield) as a white solid.

121
Synthesis of Compound 6

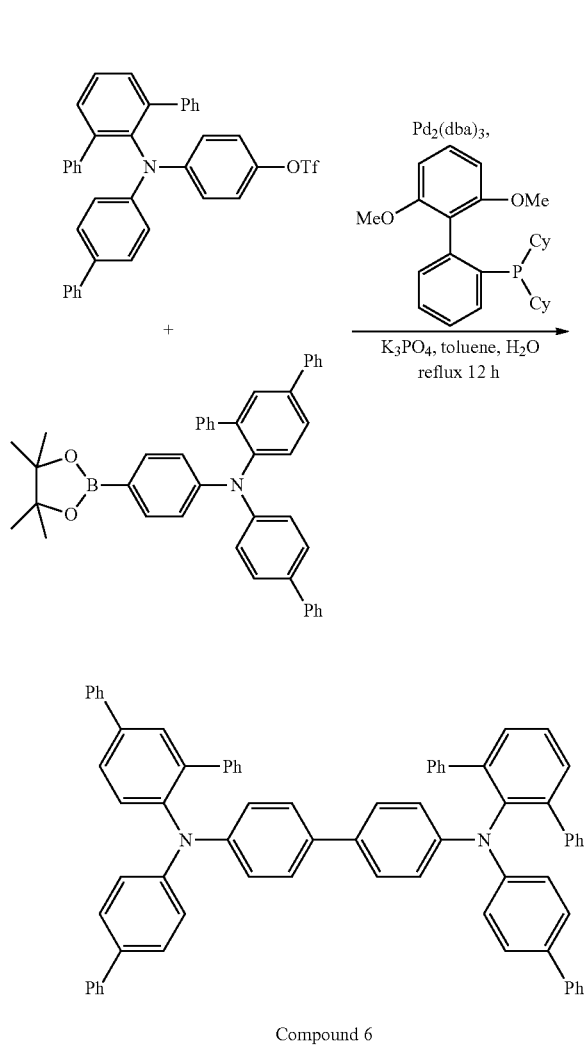

Compound 6

To a solution of 4-([1,1'-biphenyl]-4-yl([1,1':3',1''-terphenyl]-2'-yl)amino)phenyl trifluoromethanesulfonate (3.0 g, 4.8 mmol), N-([1,1'-biphenyl]-4-yl)-N-(4-(4,4,5,5-tetramethyl-1,3,2-dioxaborolan-2-yl)phenyl)-[1,1':3',1''-terphenyl]-4'-amine (3.2 g, 5.3 mmol), 2-dicyclohexylphosphino-2',6'-dimethoxybiphenyl (0.24 g, 0.58 mmol), $K_3PO_4$ (6.1 g, 28.8 mmol) in toluene (60 mL) and water (6 mL) was bubbled with nitrogen for 30 min. $Pd_2(dba)_3$ (0.13 g, 0.14 mmol) was added. The mixture was bubbled with nitrogen for 15 min. The resultant mixture was refluxed for 12 h. The reaction mixture was filtered through a silica pad and washed with toluene (containing 2% triethylamine). The solvent was removed in vacuo and the residue was purified by flash chromatography using 20% toluene/hexane (containing 2% triethylamine) to afford Compound 6 (3.6 g, 79% yield) as a white solid.

122
Synthesis of Compound 4

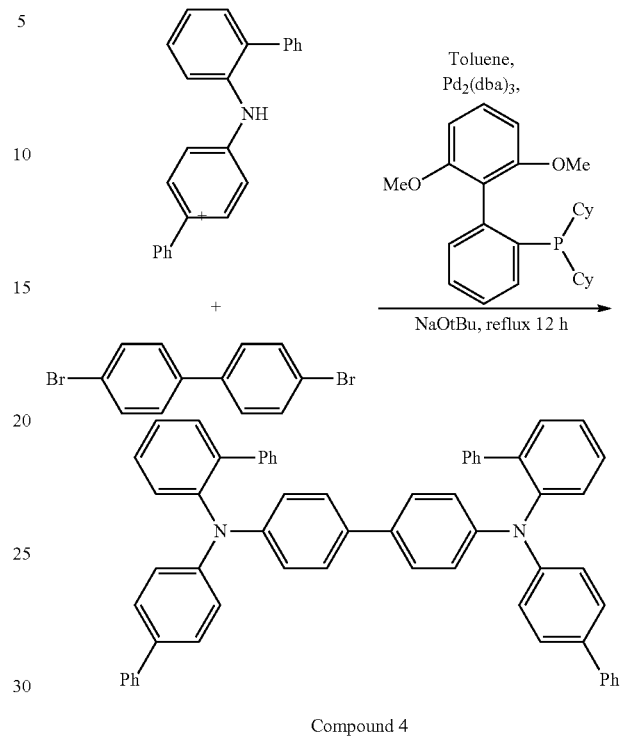

Compound 4

Toluene (125 mL) was bubbled with nitrogen for 15 min, followed by addition of 2-dicyclohexylphosphino-2',6'-dimethoxybiphenyl (0.30 g, 0.72 mmol) and $Pd_2(dba)_3$ (0.17 g, 0.18 mmol). The mixture was bubbled with nitrogen for 15 min, then N-([1,1'-biphenyl]-4-yl)-[1,1'-biphenyl]-2-amine (4.2 g, 13.2 mmol), 4,4'-dibromobiphenyl (1.9 g, 6.0 mmol), sodium tert-butoxide (2.3 g, 24.0 mmol) were added. The mixture was bubbled with nitrogen for 15 min and refluxed for 12 h. After cooling, the reaction mixture was filtered through a silica pad and washed with toluene (containing 1% triethylamine) The solvent was removed in vacuo and the residue was purified by flash chromatography using 30-40% toluene/hexane (containing 1% triethylamine) to afford Compound 4 (4.7 g, 98% yield) as a white solid.

Synthesis of N-[1,1'-biphenyl]-4-yl-N-(4'-bromo[1,1'-biphenyl]-4-yl)-[1,1'-biphenyl]-4-amine 2

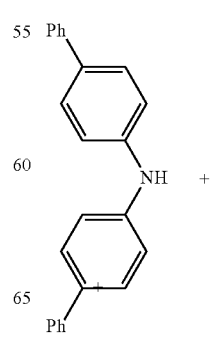

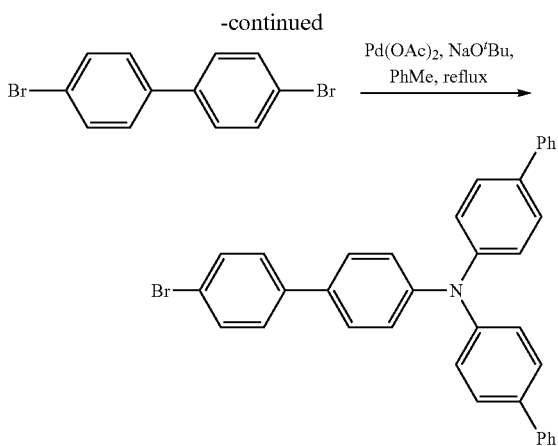

4,4'-Iminobis(biphenyl) (2.0 g, 6.23 mmol), and 4,4'-dibromobiphenyl (3.9 g, 12.6 mmol) were mixed in 150 mL of anhydrous toluene. To the solution was bubbled nitrogen while stirring for 15 min. Pd(OAc)$_2$ (0.02 g, 0.089 mmol), triphenylphosphine (0.09 g, 0.34 mmol) and $^t$BuONa (1.15 g, 11.9 mmol) were added in sequence. The mixture was heated to reflux overnight under nitrogen. After cooling, the reaction mixture was filtered through Celite pad and the solvent was then evaporated. The residue (3.1 g, 90%) was recrystallized by toluene and the crystal was further purified by boiling with 15 ml degassed toluene, 2.7 g (78%) of the desired compound was collected.

Synthesis of Compound 8

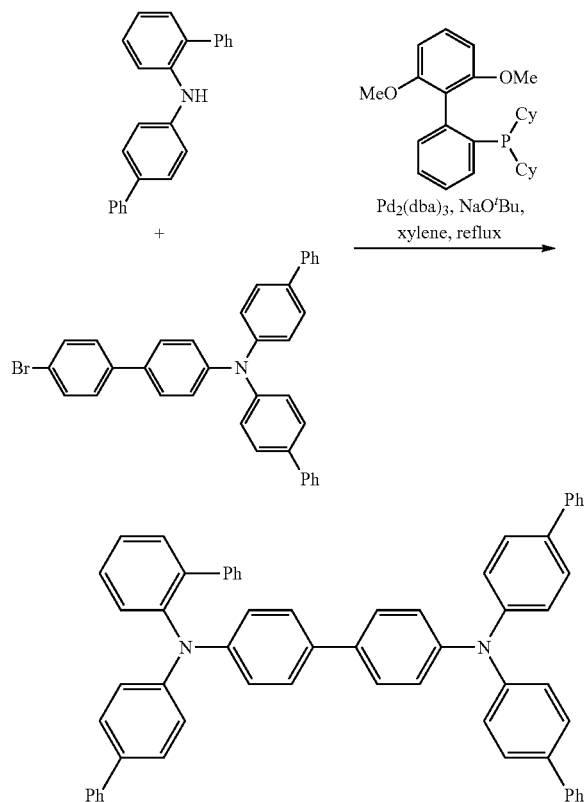

N-([1,1'-biphenyl]-4-yl)-[1,1'-biphenyl]-2-amine (1.45 g, 4.51 mmol), N-[1,1'-biphenyl]-4-yl-N-(4'-bromo[1,1'-biphenyl]-4-yl)-[1,1'-biphenyl]-4-amine (3.00 g, 5.42 mmol) were mixed in dry xylene (150 mL). The solution was bubbled nitrogen while stirring for 15 min. Pd$_2$(dba)$_3$ (0.13 g, 0.14 mmol), 2-dicyclohexylphosphino-2',6'-dimethoxybiphenyl (0.24 g, 0.59 mmol) and sodium tert-butoxide (0.86 g, 9.00 mmol) were added in sequence. The mixture was heated to reflux overnight under nitrogen. After cooling, the reaction mixture was filtered through triethylamine treated silica pad and the solvent was then evaporated. The residue was then purified by column chromatography using 20% toluene/hexane (containing 0.25% triethylamine) as eluent to obtain 4.71 g (99%) of Compound 8, which was recrystallized with 30% toluene/pentane to give 2.25 g (70%).

Synthesis of N-([1,1'-biphenyl]-4-yl)-2,4,6-triphenylamine

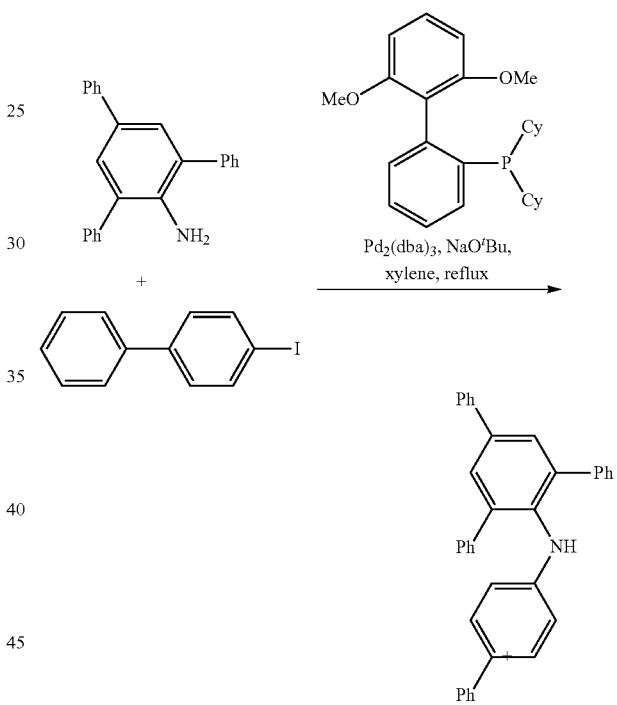

2,4,6-Triphenylamine (5.08 g, 15.81 mmol), 4-iodobiphenyl (4.70 g, 16.78 mmol) were mixed in dry xylene (100 mL). The solution was bubbled with nitrogen while stirring for 15 min. Pd$_2$(dba)$_3$ (0.44 g, 0.48 mmol), 2-dicyclohexylphosphino-2',6'-dimethoxybiphenyl (0.79 g, 1.92 mmol) and sodium tert-butoxide (3.05 g, 31.72 mmol) were added in sequence and bubbled nitrogen for 15 min. The mixture was heated to reflux overnight under nitrogen. After cooling, the reaction mixture was filtered through triethylamine treated with a silica pad and the solvent was then evaporated. The residue was purified by column chromatography using 33-60% toluene/hexane (containing 0.25% triethylamine) as eluent to obtain 6.28 g (84%) of N-([1,1'-biphenyl]-4-yl)-2,4,6-triphenylamine, which was recrystallized with 20% heptane/toluene to obtain 5.61 g (75%) of N-([1,1'-biphenyl]-4-yl)-2,4,6-triphenylamine.

125
Synthesis of N-([1,1'-biphenyl]-4-yl)-N-(4-methoxyphenyl)-5'-phenyl-[1,1':3',1''-terphenyl]-2'-amine

126
Synthesis of 4-([1,1'-biphenyl]-4-yl(5'-phenyl-[1,1': 3',1''-terphenyl]-4'-yl)amino)phenyl Trifluoromethanesulfonate

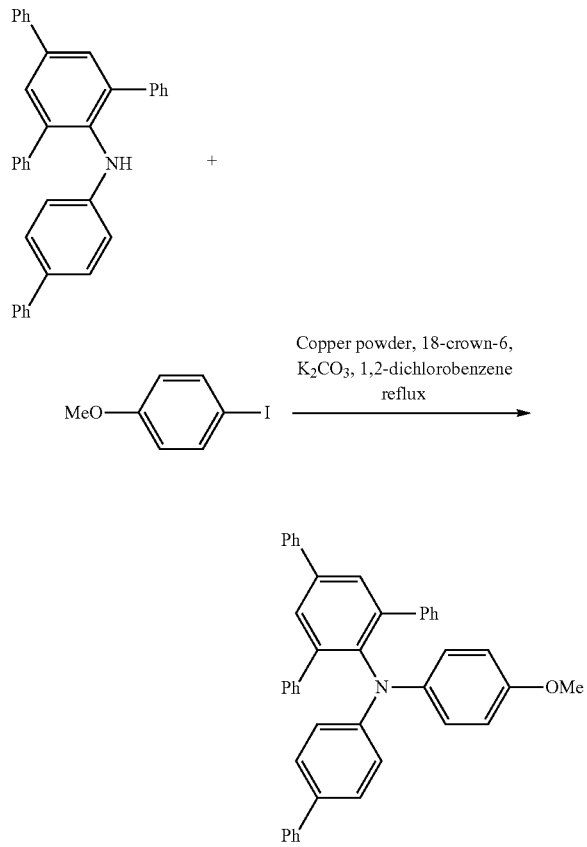

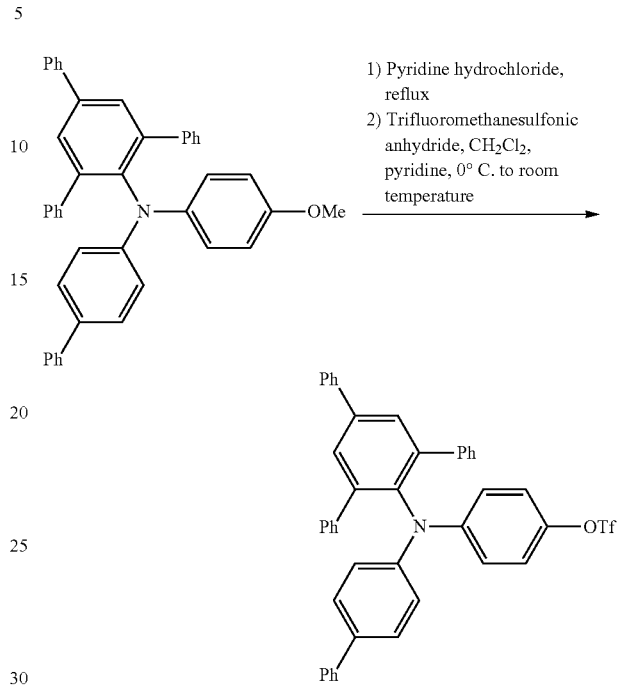

N-([1,1'-biphenyl]-4-yl)-2,4,6-triphenylamine (1.20 g, 2.53 mmol), 4-iodoanisole (2.36 g, 10.09 mmol), potassium carbonate (1.49 g, 10.80 mmol), copper powder (0.18 g, 2.85 mmol), 18-crown-6 ether (0.67 g, 2.53 mmol) and 1,2-dichlorobenzene (20 mL) were bubbled with nitrogen for 30 min. The mixture was refluxed for 15 h. After cooling, the reaction mixture was filtered through a silica pad and washed with toluene (containing 0.25% triethylamine). The solvent was removed in vacuo and the residue was purified by flash chromatography using 40% toluene/hexane (containing 0.25% triethylamine) to afford N-([1,1'-biphenyl]-4-yl)-N-(4-methoxyphenyl)-5'-phenyl-[1,1':3',1''-terphenyl]-2'-amine, which was recrystallized with 30% toluene/heptane to give a white solid (1.24 g, 85% yield).

A mixture of N-([1,1'-biphenyl]-4-yl)-N-(4-methoxyphenyl)-5'-phenyl-[1,1':3',1''-terphenyl]-2'-amine (1.24 g, 2.13 mmol) and pyridine hydrochloride (1.90 g, 16.4 mmol) were heated to reflux under nitrogen for 2 h. Upon cooling, water was added and the precipitate was filtered and dried. The solid was dissolved in toluene and filtered through triethylamine treated silica pad and the solvent was then evaporated to give off-white powder (1.20 g, 100%) of 4-([1,1'-biphenyl]-4-yl (4'-(di([1,1'-biphenyl]-4-yl)amino)-[1,1'-biphenyl]-4-yl) amino)phenol 13 which was used for the next step without further purification. To the above residue was added to a flask under nitrogen with anhydrous pyridine (1.1 mL, 13.6 mmol) and anhydrous dichloromethane (30 mL). The solution was cooled in an ice bath and trifluoromethanesulfonic anhydride (1.45 mL, 8.62 mmol) was added slowly via syringe. The solution was warmed to room temperature and stirred overnight. The solution was added to MeOH (5 mL) and concentrated. Residue was added to water, extracted with toluene, dried with MgSO$_4$ and the solvent was concentrated. The residue was purified by column chromatography with 20% toluene/hexane (containing 0.25% Et$_3$N) as eluent resulting in 1.29 g (87%) of 4-([1,1'-biphenyl]-4-yl(4'-(di([1,1'-biphenyl]-4-yl)amino)-[1,1'-biphenyl]-4-yl)amino)phenyl trifluoromethanesulfonate, which was recrystallized with heptane-toluene (7:3) to give 1.125 g (76%) of 4-([1,1'-biphenyl]-4-yl(4'-(di([1,1'-biphenyl]-4-yl)amino)-[1,1'-biphenyl]-4-yl) amino)phenyl trifluoromethanesulfonate.

Synthesis of N-([1,1'-biphenyl]-4-yl)-5'-phenyl-N-(4-(4,4,5,5-tetramethyl-1,3,2-dioxaborolan-2-yl)phenyl)-[1,1':3',1''-terphenyl]-2'-amine

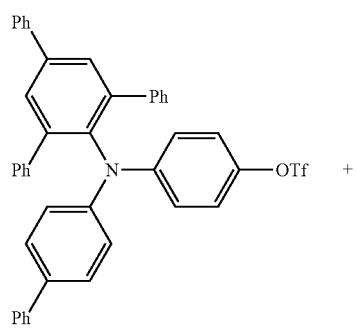

+

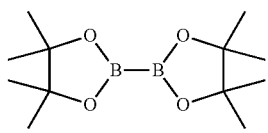 1,4-dioxane, KOAc, Pd(dppf)Cl₂·CH₂Cl₂ reflux →

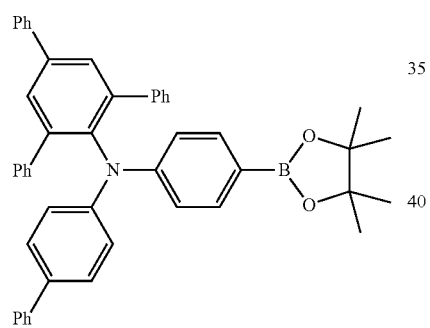

To a solution of 4-([1,1'-biphenyl]-4-yl(5'-phenyl-[1,1':3',1''-terphenyl]-4'-yl)amino)phenyl trifluoromethanesulfonate (4.18 g, 5.99 mmol) in 1,4-dioxane (80 mL) was added bis(pinacolato)diboron (2.28 g, 8.99 mmol), KOAc (2.38 g, 24.2 mmol), and the solution was bubbled with nitrogen for 15 min. Pd(dppf)Cl₂·CH₂Cl₂ (0.300 g, 0.37 mmol) was then added to the solution, and the reaction mixture was bubbled with nitrogen for 15 min. The resultant mixture was refluxed for 12 h. After cooling, H₂O (1 mL) was added and stirred for 15 min. The reaction mixture was filtered through an Et₃N treated silica pad and washed with toluene (containing 0.25% triethylamine). The solvent was removed in vacuo and the residue was purified by flash chromatography using 20-50% toluene/hexane (containing 0.25% triethylamine) as eluent to afford N-([1,1'-biphenyl]-4-yl)-5'-phenyl-N-(4-(4,4,5,5-tetramethyl-1,3,2-dioxaborolan-2-yl)phenyl)-[1,1':3',1''-terphenyl]-2'-amine (2.92 g, 72% yield) as a white solid. It was recrystallized with 25% toluene/heptane to give 2.15 g (53%) of N-([1,1'-biphenyl]-4-yl)-5'-phenyl-N-(4-(4,4,5,5-tetramethyl-1,3,2-dioxaborolan-2-yl)phenyl)-[1,1':3',1''-terphenyl]-2'-amine.

Synthesis of Compound 2

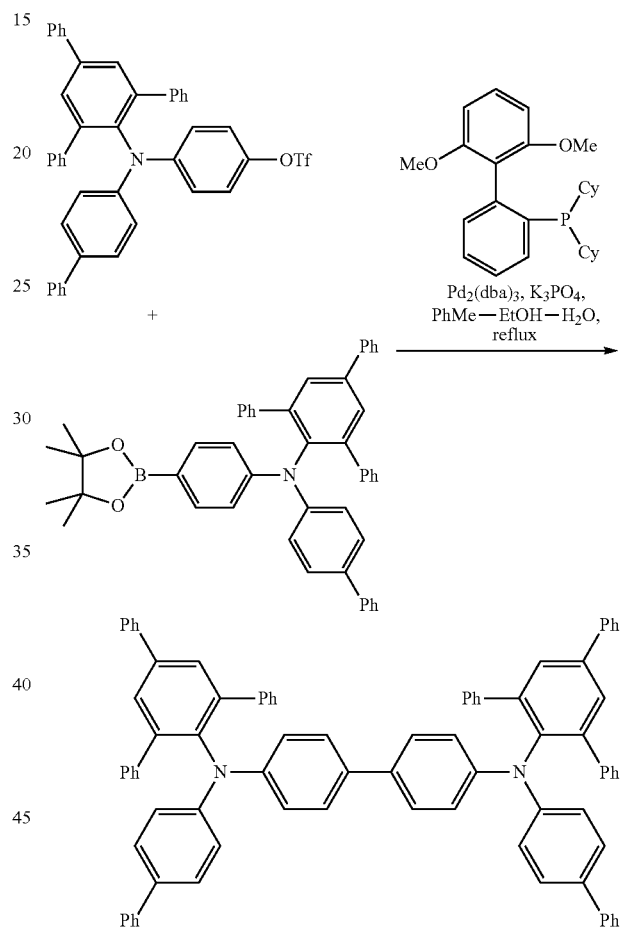

Compound 2

To a stirred solution of 4-([1,1'-biphenyl]-4-yl(5'-phenyl-[1,1':3',1''-terphenyl]-4'-yl)amino)phenyl trifluoromethanesulfonate (1.82 g, 2.61 mmol) in toluene (99 mL) and water (5.5 mL) and ethanol (5.5 mL), N-([1,1'-biphenyl]-4-yl)-5'-phenyl-N-(4-(4,4,5,5-tetramethyl-1,3,2-dioxaborolan-2-yl)phenyl)-[1,1':3',1''-terphenyl]-2'-amine (2.64 g, 3.91 mmol) and K₃PO₄ (1.75 g, 8.23 mmol) were added and the mixture was degassed with nitrogen for 15 min, then Pd₂(dba)₃ (0.095 g, 0.10 mmol) and 2-dicyclohexylphosphino-2',6'-dimethoxybiphenyl (0.14 g, 0.35 mmol) were added and degassed with nitrogen for another 15 min. The mixture was refluxed overnight. After cooling to room temperature, the reaction mixture was filtered through Et₃N treated silica gel and concentrated. The residue was purified by column chromatography using 30% toluene/hexane (containing 0.25% Et₃N) as eluent resulting in 1.96 g (68%) of Compound 2.

Synthesis of N-([1,1'-biphenyl]-4-yl)-N-(4-(4,4,5,5-tetramethyl-1,3,2-dioxaborolan-2-yl)phenyl)-[1,1'-biphenyl]-4-amine

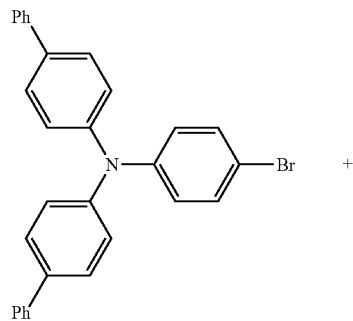

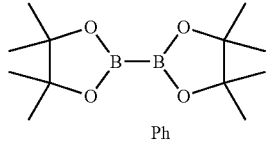

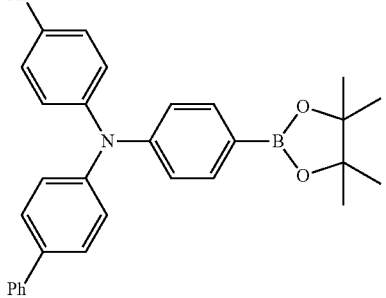

N-([1,1'-biphenyl]-4-yl)-N-(4-bromophenyl)-[1,1'-biphenyl]-4-amine (15.42 g, 32.4 mmol), bis(pinacolato)diboron (12.79 g, 50.3 mmol) and KOAc (9.80 g, 99.9 mmol) were mixed in 300 mL of anhydrous 1,4-dioxane. The solution was bubbled with nitrogen while stirring for 15 min, then Pd(dppf)Cl₂·CH₂Cl₂ (0.80 g, 0.98 mmol) was added. The mixture was heated to reflux overnight under nitrogen. Water (3 mL) was added and stirred for 15 min. The reaction mixture was filtered through silica pad, washed with CH₂Cl₂ and the solvent was evaporated. The residue was then purified by column chromatography using 20-50% dichloromethane/hexane as eluent to obtain 11.9 g (71%) of N-([1,1'-biphenyl]-4-yl)-N-(4-(4,4,5,5-tetramethyl-1,3,2-dioxaborolan-2-yl) phenyl)-[1,1'-biphenyl]-4-amine, which was recrystallized with heptane to obtain 9.3 g (55%) of N-([1,1'-biphenyl]-4-yl)-N-(4-(4,4,5,5-tetramethyl-1,3,2-dioxaborolan-2-yl)phenyl)-[1,1'-biphenyl]-4-amine.

Synthesis of Compound 10

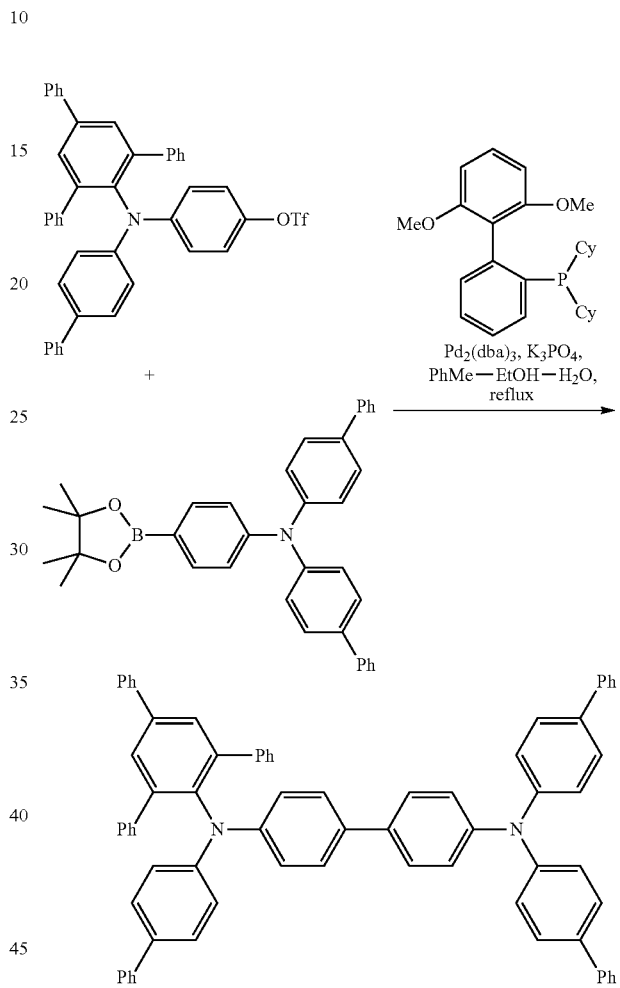

Compound 10

To a stirred solution of 4-([1,1'-biphenyl]-4-yl(5'-phenyl-[1,1':3',1''-terphenyl]-4'-yl)amino)phenyl trifluoromethanesulfonate (2.41 g, 3.2 mmol) in toluene (144 mL) and water (8 mL) and ethanol (8 mL), N-([1,1'-biphenyl]-4-yl)-N-(4-(4,4,5,5-tetramethyl-1,3,2-dioxaborolan-2-yl)phenyl)-[1,1'-biphenyl]-4-amine (2.11 g, 3.82 mmol) and K₃PO₄ (0.13 g, 0.61 mmol) were added and the mixture was degassed with nitrogen for 15 min, then Pd₂(dba)₃ (0.13 g, 0.14 mmol) and 2-dicyclohexylphosphino-2',6'-dimethoxybiphenyl (0.18 g, 0.43 mmol) were added and degassed with nitrogen for another 15 min. The mixture was refluxed overnight. After cooling to room temperature, the reaction mixture was filtered thru Et₃N treated silica gel and concentrated. The residue was purified by column chromatography using 10-50% toluene/hexane (containing 0.25% Et₃N) as eluent resulting in 2.90 g (96%) of Compound 10, which was recrystallized with 50% toluene/heptane to give 2.43 g (80%).

131
Synthesis of Compound 12

132
Synthesis of Compound 13

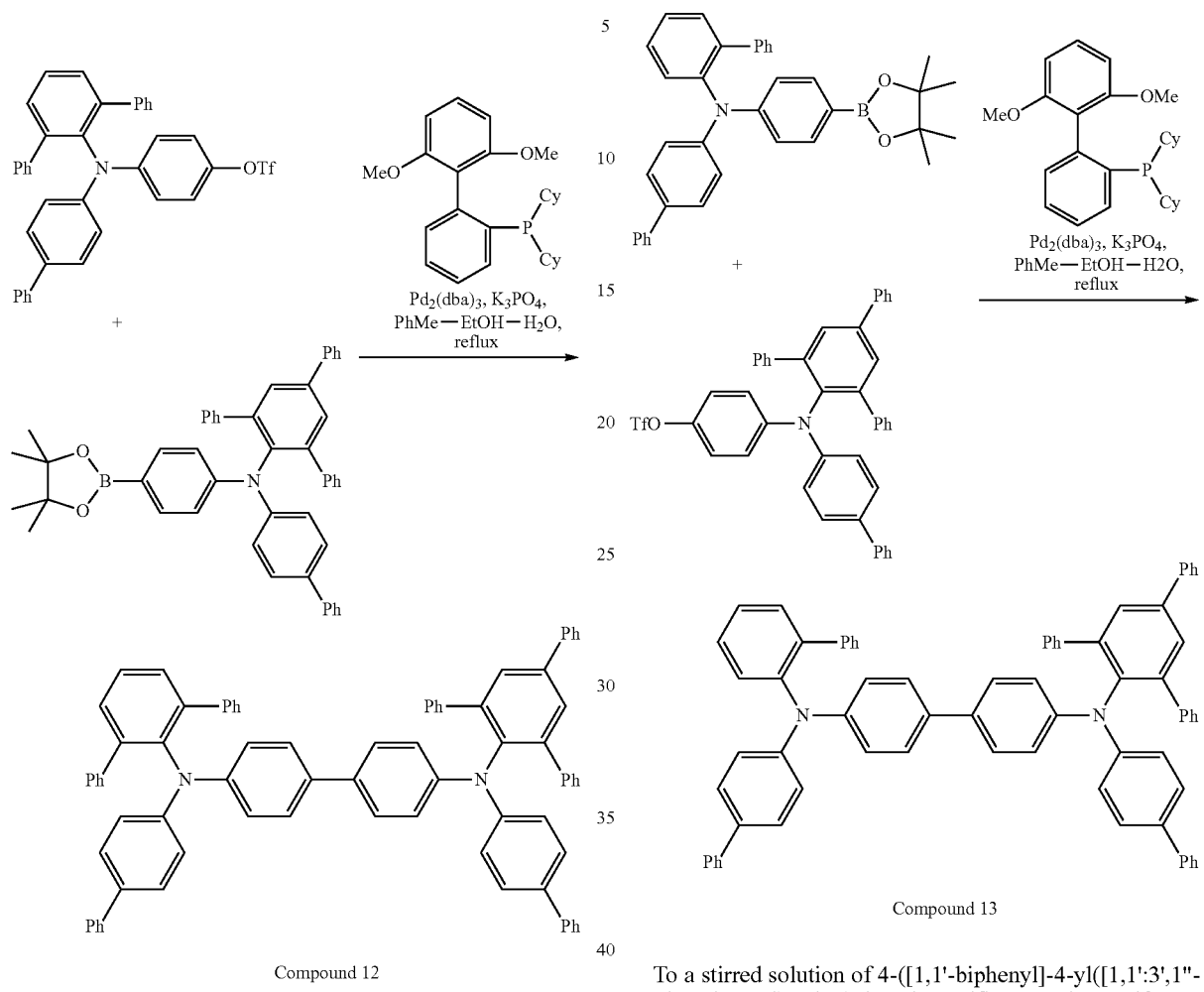

Compound 12

Compound 13

To a stirred solution of 4-([1,1'-biphenyl]-4-yl([1,1':3',1"-terphenyl]-2'-yl)amino)phenyl trifluoromethanesulfonate (2.15 g, 3.46 mmol) in toluene (144 mL) and water (8 mL) and ethanol (8 mL), N-([1,1'-biphenyl]-4-yl)-5'-phenyl-N-(4-(4,4,5,5-tetramethyl-1,3,2-dioxaborolan-2-yl)phenyl)-[1,1':3',1"-terphenyl]-2'-amine (2.40 g, 3.55 mmol) and $K_3PO_4$ (2.25 g, 10.62 mmol) were added and the mixture was degassed with nitrogen for 15 min, then $Pd_2(dba)_3$ (0.13 g, 0.14 mmol) and 2-dicyclohexylphosphino-2',6'-dimethoxybiphenyl (0.18 g, 0.44 mmol) were added and degassed with nitrogen for another 15 min. The mixture was refluxed overnight. After cooling to room temperature, the reaction mixture was filtered through $Et_3N$-treated silica and concentrated. The residue was purified by column chromatography using 20-40% toluene/hexane (containing 0.25% $Et_3N$) as eluent resulting in 1.57 g (44%) of Compound 13. It was recrystallized with 25% toluene/heptane to give 1.23 g (34%) of Compound 12.

To a stirred solution of 4-([1,1'-biphenyl]-4-yl([1,1':3',1"-terphenyl]-2'-yl)amino)phenyl trifluoromethanesulfonate (1.25 g, 1.79 mmol) in toluene (90 mL) and water (5 mL) and ethanol (5 mL), N-([1,1'-biphenyl]-4-yl)-N-(4-(4,4,5,5-tetramethyl-1,3,2-dioxaborolan-2-yl)phenyl)-[1,1'-biphenyl]-2-amine (0.99 g, 1.85 mmol) and K3PO4 (1.18 g, 5.57 mmol) were added and the mixture was degassed with nitrogen for 15 min, then Pd2(dba)3 (0.15 g, 0.16 mmol) and 2-dicyclohexylphosphino-2',6'-dimethoxybiphenyl (0.15 g, 0.37 mmol) were added and degassed with nitrogen for another 15 min. The mixture was refluxed overnight. After cooling to room temperature, the reaction mixture was filtered through Et3N-treated silica and concentrated. The residue was purified by column chromatography using 20-40% toluene/hexane (containing 0.25% Et3N) as eluent resulting in 0.84 g (50%) of Compound 13.

Example devices based on the present invention were also fabricated as described below.

All OLED device examples were preferably fabricated by high vacuum (<$10^{-7}$ Torr) thermal evaporation. The anode electrode is ~800 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of $H_2O$ and $O_2$) and a moisture getter was incorporated inside the package.

The organic stack of the Device Examples 1-1, 1-2, 1-3, 1-4, 2-1, 3-1 and 4-1, and Comparative Device Examples 1-1, 1-2, 2-1, 3-1 and 4-1 in Tables 3A and 3B include, sequentially from the ITO surface, 100 Å of LG101 (purchased from LG Chem, Korea) as the hole injection layer (HIL), 250 Å of the invention compounds or NPD as the hole transporting layer (HTL), 300 Å of Compound A or Compound B doped with 12%, 18% or 20% of phosphorescent emitter Compound C as the emissive layer (EML), 50 Å of Compound A or Compound B as the ETL2 and 350 Å of Alq₃ as the ETL1.

The organic stack of the Device Example 5-1 and Comparative Device Examples 5-1 and 5-2 in Tables 4A and 4B include, sequentially from the ITO surface, 100 Å of LG101 (purchased from LG Chem, Korea) as the hole injection layer (HIL), 550 Å of the invention compounds or NPD as the hole transporting layer (HTL), 300 Å of Compound D doped with 12% of phosphorescent emitter Compound E as the emissive layer (EML), 50 Å of Compound D as the ETL2 and 450 Å of Alq₃ as the ETL1.

Compound E

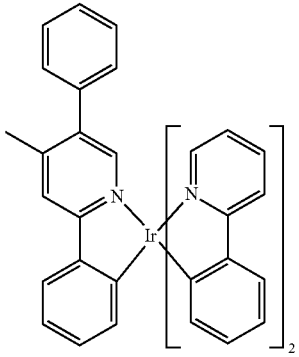

Comparative Cmpd 1

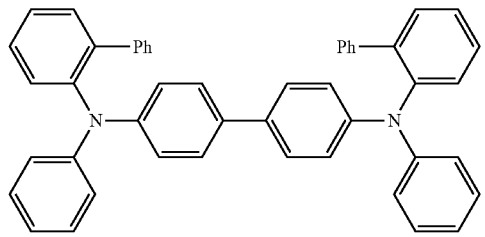

Compound A

Compound B

Compound C

Compound D

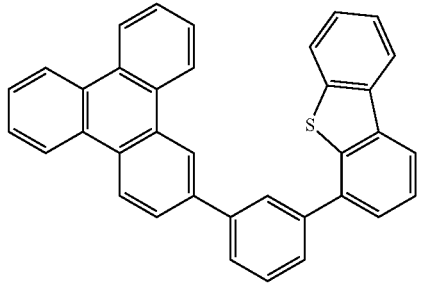

TABLE 3A

Device structure and data

| Device Example | HTL 250Å | EML 300Å | BL 50Å | 1931 CIE x | y |
|---|---|---|---|---|---|
| 1-1 | Cmpd 4 | Cmpd A: Cmpd C 15% | Cmpd A | 0.176 | 0.390 |
| 1-2 | Cmpd 5 | Cmpd A: Cmpd C 15% | Cmpd A | 0.177 | 0.405 |
| 1-3 | Cmpd 9 | Cmpd A: Cmpd C 15% | Cmpd A | 0.178 | 0.405 |
| 1-4 | Cmpd 1 | Cmpd A: Cmpd C 15% | Cmpd A | 0.176 | 0.401 |
| Comparative 1-1 | Comparative Cmpd 1 | Cmpd A: Cmpd C 15% | Cmpd A | 0.175 | 0.390 |
| Comparative 1-2 | NPD | Cmpd A: Cmpd C 15% | Cmpd A | 0.176 | 0.395 |
| 2-1 | Cmpd 2 | Cmpd A: Cmpd C 18% | Cmpd A | 0.182 | 0.409 |
| Comparative 2 | NPD | Cmpd A: Cmpd C 18% | Cmpd A | 0.182 | 0.409 |
| 3-1 | Cmpd 8 | Cmpd B: Cmpd C 18% | Cmpd A | 0.181 | 0.409 |
| Comparative 3 | NPD | Cmpd B: Cmpd C 18% | Cmpd A | 0.181 | 0.409 |
| 4-1 | Cmpd 3 | Cmpd B: Cmpd C 20% | Cmpd B | 0.182 | 0.413 |
| Comparative 4 | NPD | Cmpd B: Cmpd C 20% | Cmpd B | 0.181 | 0.410 |

TABLE 3B

Device structure and data

| Device Example | Voltage [V] | At 1000 cd/m² LE [cd/A] | EQE [%] | PE [lm/W] | J = 40 mA/cm² L₀ [cd/m²] | LT80% [h] |
|---|---|---|---|---|---|---|
| 1-1 | 6.2 | 48.1 | 21.4 | 24.6 | 7641 | 33 |
| 1-2 | 6 | 50.9 | 21.9 | 26.5 | 8047 | 55 |

TABLE 3B-continued

Device structure and data

| Device Example | At 1000 cd/m² | | | | J = 40 mA/cm² | |
|---|---|---|---|---|---|---|
| | Voltage [V] | LE [cd/A] | EQE [%] | PE [lm/W] | L₀ [cd/m²] | LT80% [h] |
| 1-3 | 6.1 | 50.2 | 21.6 | 25.9 | 7847 | 54 |
| 1-4 | 6.1 | 49.8 | 21.6 | 25.7 | 7790 | 32 |
| Comparative 1-1 | 5.9 | 50.5 | 22.4 | 26.7 | 7903 | 24 |
| Comparative 1-2 | 6 | 46.7 | 20.5 | 24.4 | 7295 | 36 |
| 2-1 | 6 | 41.8 | 17.9 | 22 | 7202 | 67 |
| Comparative 2 | 6.1 | 40.7 | 17.5 | 20.9 | 6920 | 52 |
| 3-1 | 7.2 | 48.5 | 20.8 | 21.3 | 7605 | 91 |
| Comparative 3 | 7.3 | 46.6 | 20 | 20.1 | 7230 | 90 |
| 4-1 | 6.6 | 45.6 | 19.4 | 21.7 | 7360 | 76 |
| Comparative 4 | 6.6 | 44.1 | 18.8 | 20.9 | 7047 | 78 |

TABLE 4A

Device structure and data

| Device Example | HTL 550Å | EML 300Å | BL 50Å | 1931 CIE | |
|---|---|---|---|---|---|
| | | | | x | y |
| 5-1 | Cmpd 4 | Cmpd D: Cmpd E 12% | Cmpd D | 0.319 | 0.630 |
| Comparative 5-1 | Comparative Cmpd 1 | Cmpd D: Cmpd E 12% | Cmpd D | 0.333 | 0.623 |
| Comparative 5-2 | NPD | Cmpd D: Cmpd E 12% | Cmpd D | 0.337 | 0.621 |

TABLE 4B

Device structure and data

| Device Example | At 1000 cd/m² | | | | J = 40 mA/cm² | |
|---|---|---|---|---|---|---|
| | Voltage [V] | LE [cd/A] | EQE [%] | PE [lm/W] | L₀ [cd/m²] | LT80% [h] |
| 5-1 | 4.9 | 65.8 | 18.1 | 42.3 | 20528 | 420 |
| Comparative 5-1 | 4.8 | 72.5 | 19.7 | 47.7 | 23230 | 304 |
| Comparative 5-2 | 4.9 | 66.5 | 18.1 | 42.9 | 20320 | 358 |

The data shows that in devices with the HTL materials containing twisted aryl group(s), the amino groups provide superior device efficiency and/or lifetime in comparison to NPD, a well-known standard material in OLEDs. It may be preferred to include biphenyl-4-yl groups on the amino group, which provides conjugation to the amino nitrogen and improvement in device lifetime. For example, Compound 4 has biphenyl-4-yl connected to the nitrogen, whereas the Comparative Compound has only phenyl connected to the nitrogen. $LT_{80}$ is the time required for the initial luminance ($L_0$) to drop to 80% of its initial value, at a constant current density of 40 mA/cm². The $LT_{80}$ of the device in Example 1-1 (including Compound 4) is 33 h, whereas that of Comparative Device Example 1-1 is 24 h. As another example, is the $LT_{80}$ of Device Example 5-1 (including Compound 4) is 420 h, whereas that of Comparative Device Example 5-1 is 304 h.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the following general structure:

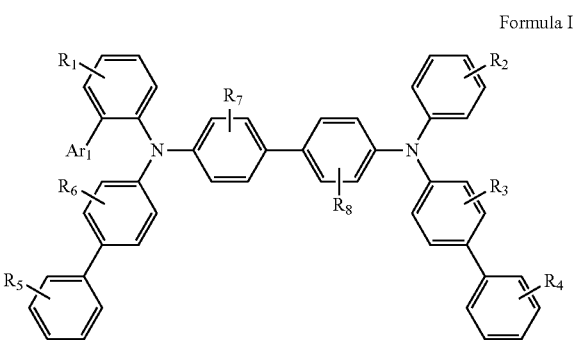

Formula I wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein each of $R_1$, $R_2$, $R_3$, $R_4$, $R_5$, $R_6$, $R_7$ and $R_8$ does not form cyclic rings, and wherein $Ar_1$ is selected from the group consisting of aryl and heteroaryl.

2. The compound of claim 1, wherein the compound has the following general structure:

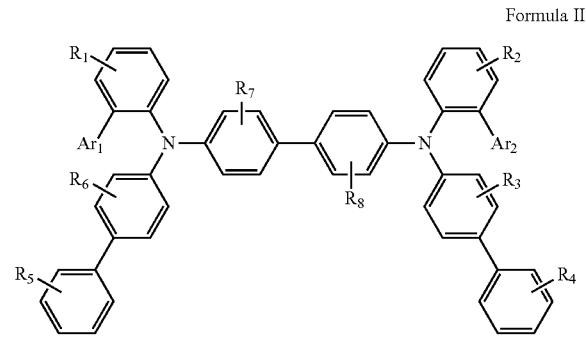

Formula II wherein $Ar_1$ and $Ar_2$ are independently selected from the group consisting of aryl and heteroaryl.

3. The compound of claim 2, wherein the compound has the following general structure:

Formula III
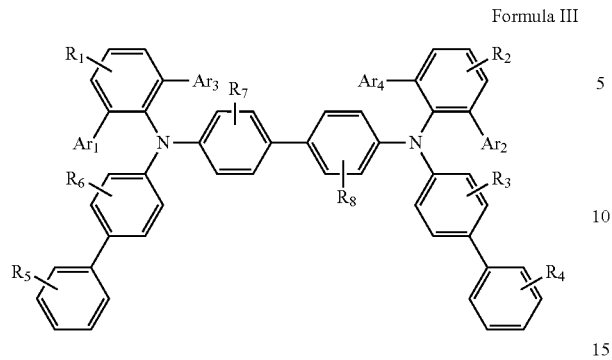
wherein Ar₁, Ar₂, Ar₃ and Ar₄ are independently selected from the group consisting of aryl and heteroaryl.
4. The compound of claim 1, wherein the compound is selected from the group consisting of:
Compound 1
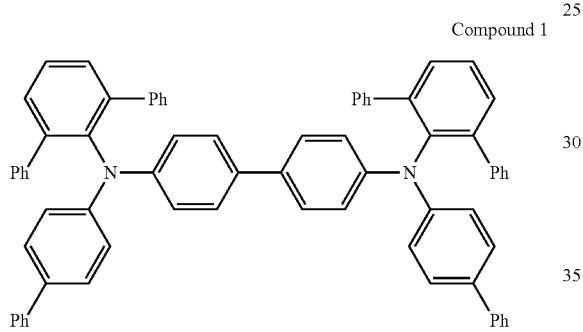
Compound 2
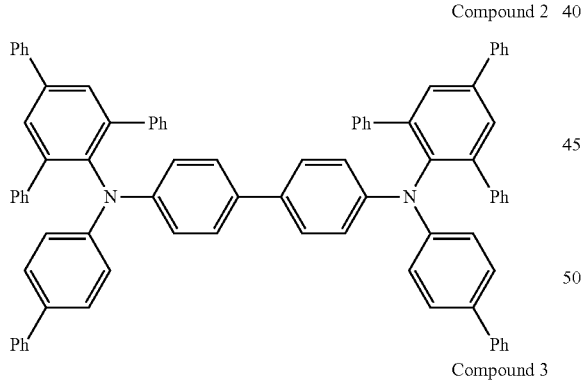
Compound 3
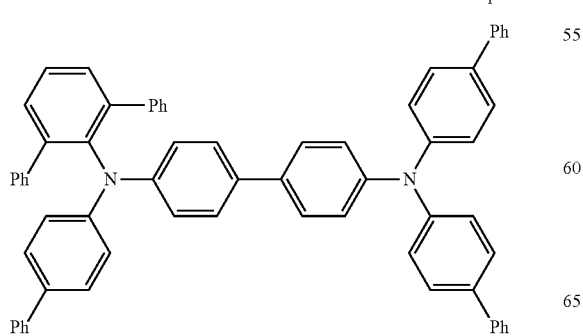
Compound 4
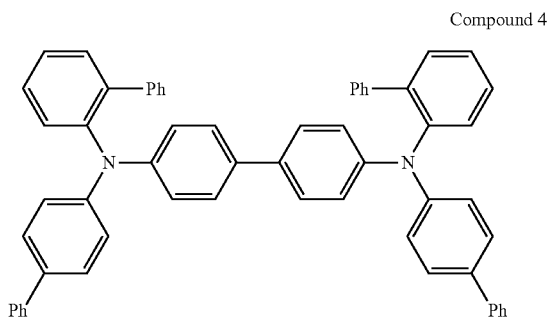
Compound 5
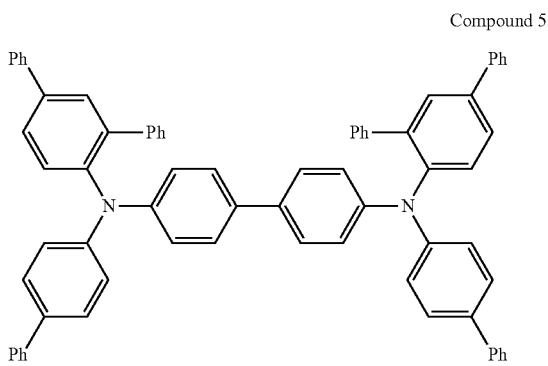
Compound 6
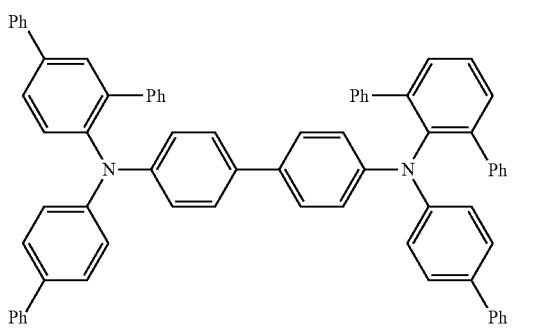
Compound 7
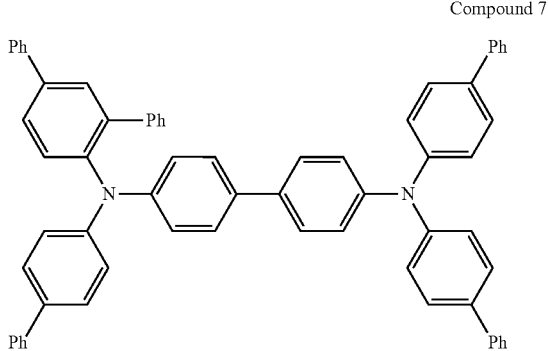

Compound 8
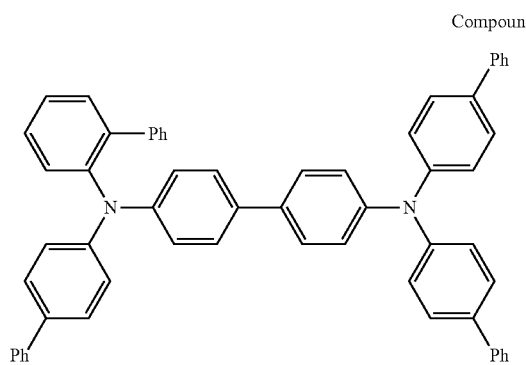
Compound 12
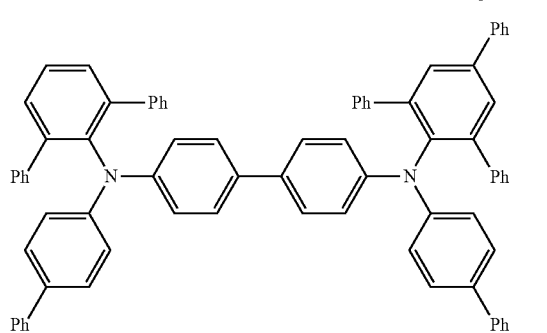
Compound 9
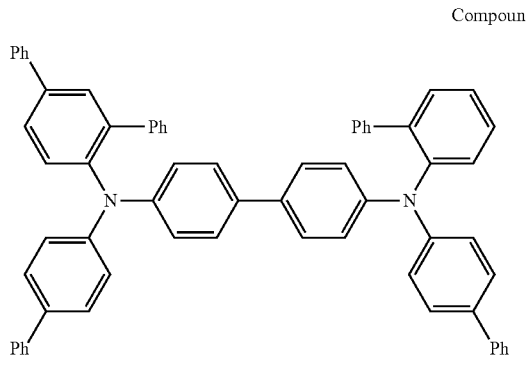
Compound 13
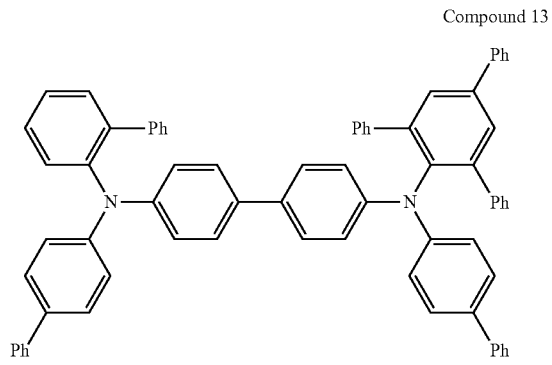
Compound 10
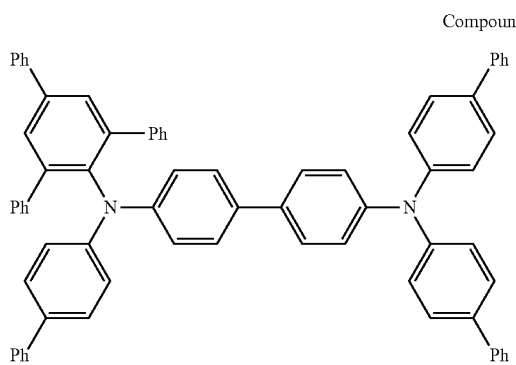
Compound 14
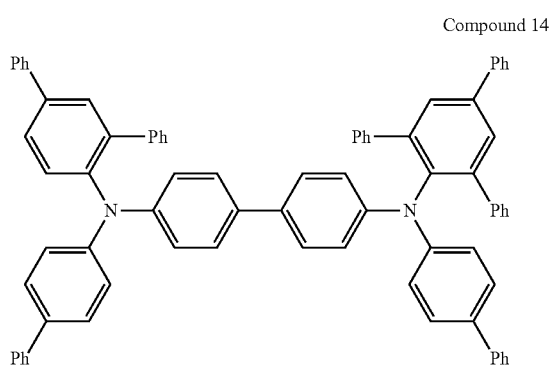
Compound 11
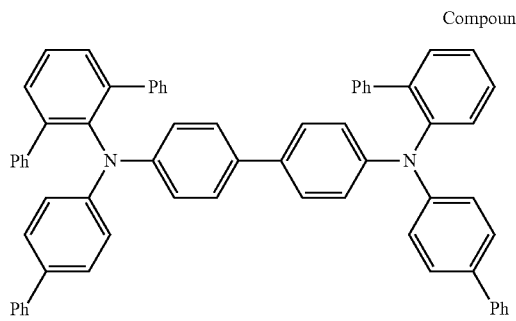
Compound 15
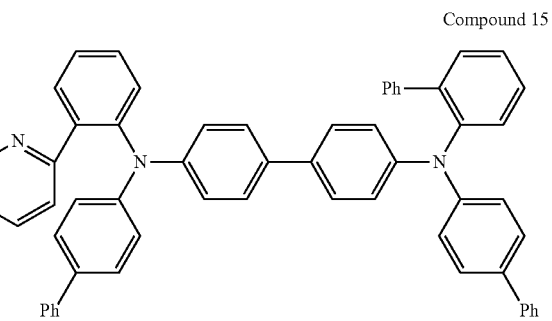

-continued

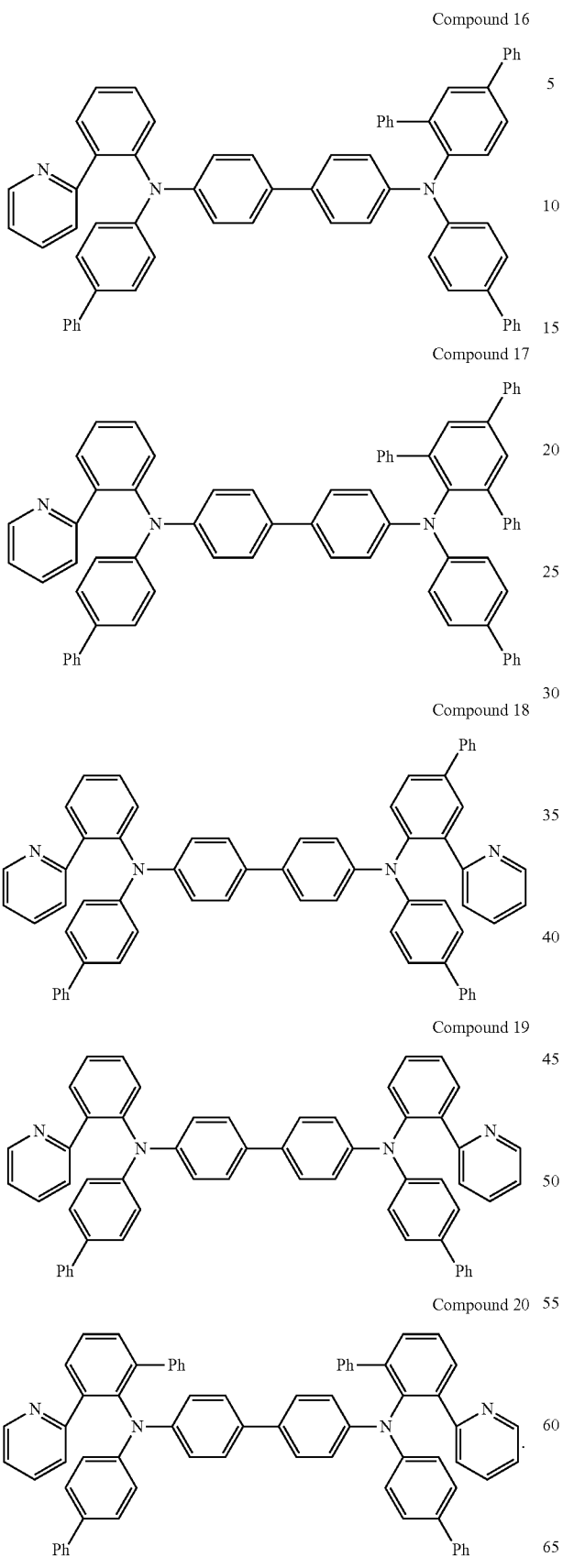

Compound 16

Compound 17

Compound 18

Compound 19

Compound 20

5. A first device comprising:
a first organic light emitting device, further comprising:
an anode; a cathode; and an organic layer disposed between the anode and the cathode; wherein the organic layer comprises a compound having the following general structure:

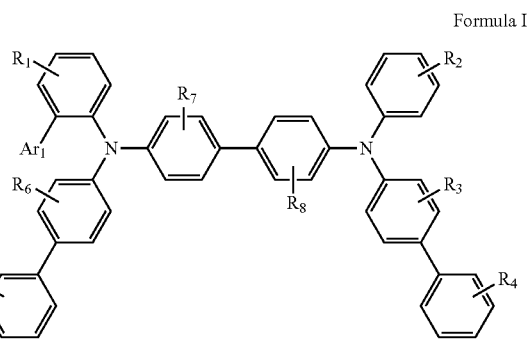

Formula I wherein $R_1$, $R_2$, $R_3$, $R_4$, $R_5$, $R_6$, $R_7$ and $R_8$ are each independently unsubstituted or selected from the group of mono, di, tri, tetra or penta substitutions selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R_1$, $R_2$, $R_3$, $R_4$, $R_5$, $R_6$, $R_7$ and $R_8$ do not form cyclic rings, and wherein $Ar_1$ is selected from the group consisting of aryl and heteroaryl.

6. The first device of claim 5, wherein the first organic light emitting device further comprises an emissive layer; and wherein the organic layer is disposed between the anode and the emissive layer.

7. The first device of claim 6, wherein the organic layer is a hole transporting layer.

8. The first device of claim 5, wherein the first device is a consumer product.

9. The first device of claim 5, wherein the first device is an organic light-emitting device.

10. The first device of claim 5, wherein the first device comprises a lighting panel.

11. The first device of claim 5, wherein the organic layer comprises a compound selected from the group consisting of:

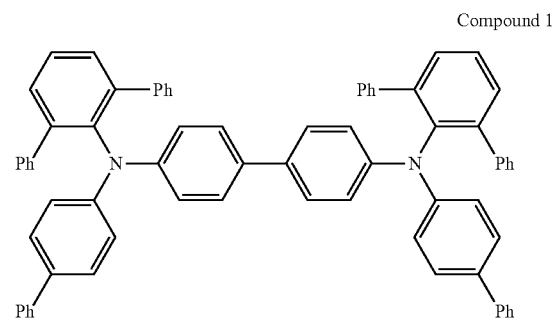

Compound 1

Compound 2
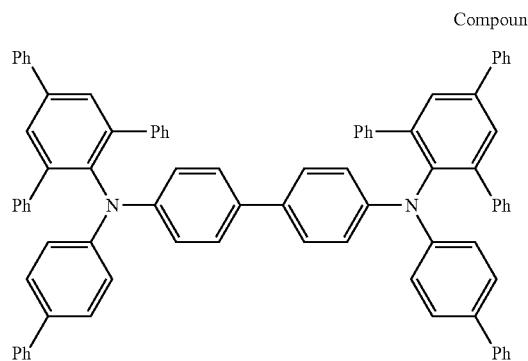
Compound 6
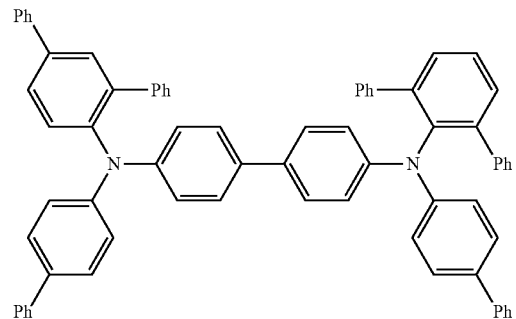
Compound 3
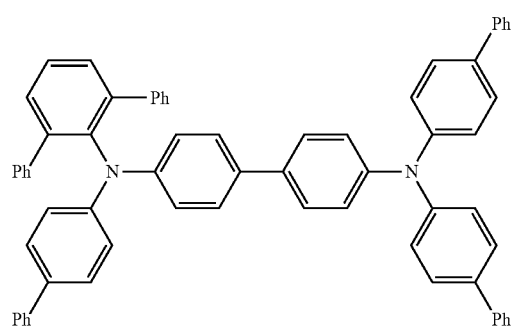
Compound 7
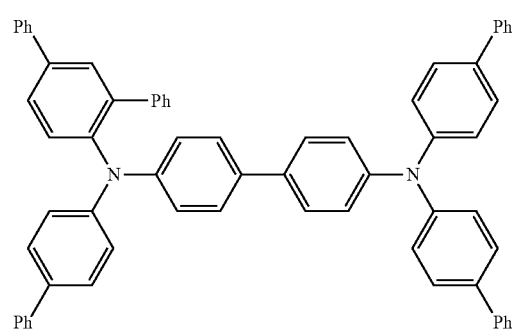
Compound 4
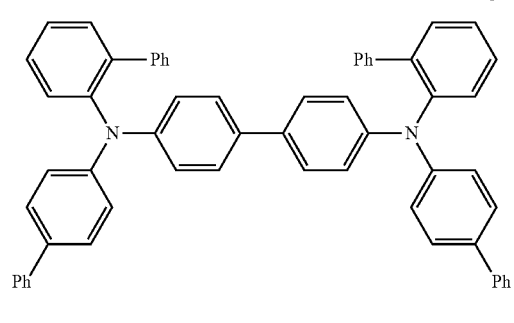
Compound 8
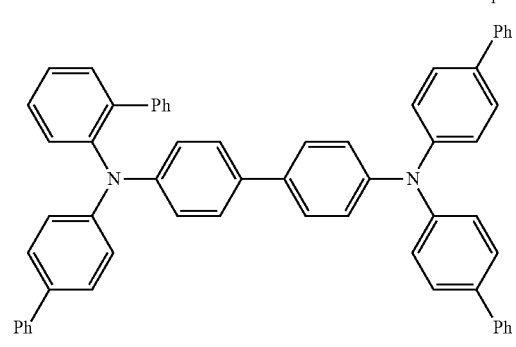
Compound 5
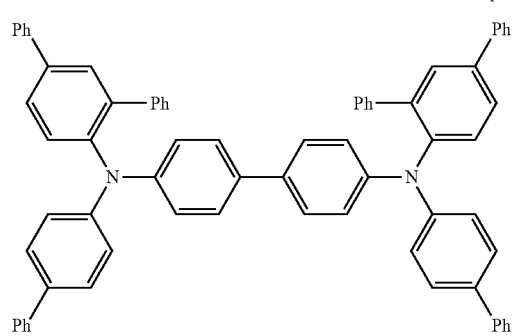
Compound 9
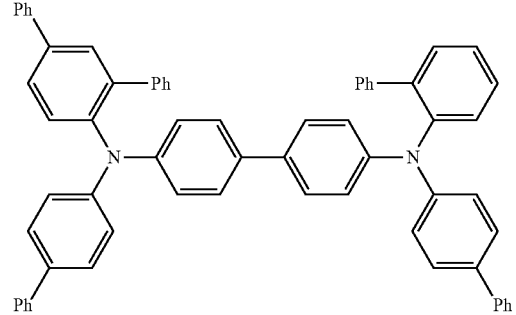

Compound 10
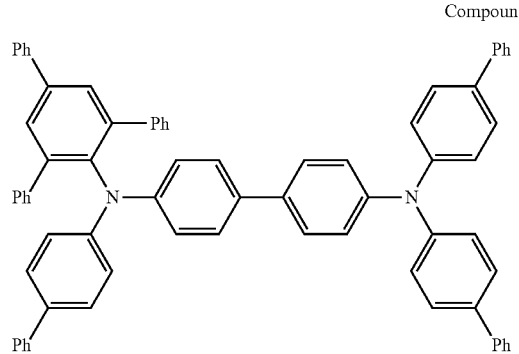
Compound 11
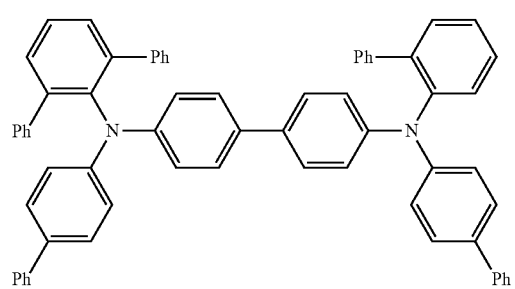
Compound 12
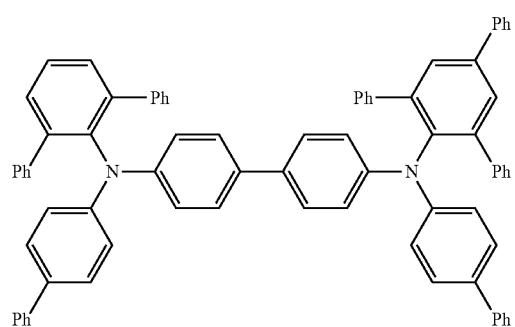
Compound 13
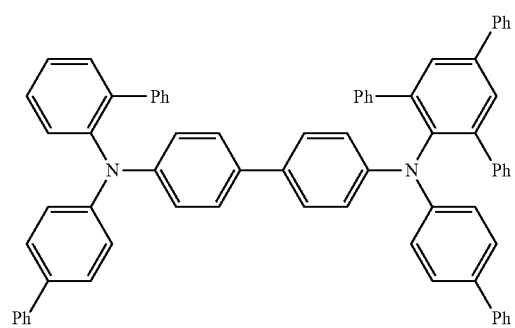
Compound 14
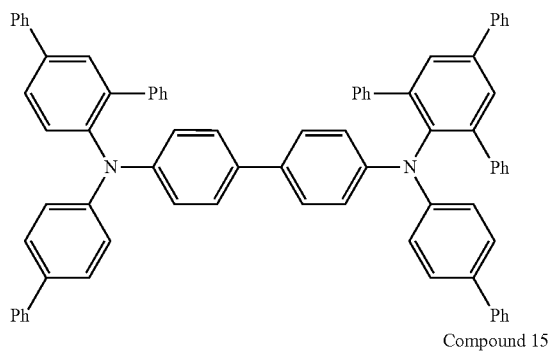
Compound 15
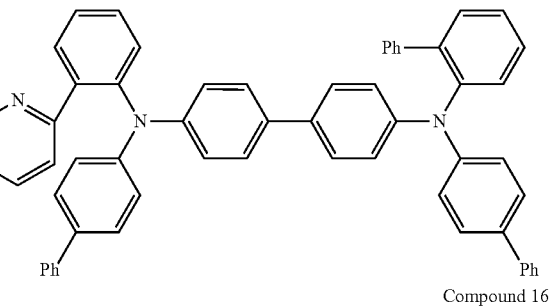
Compound 16
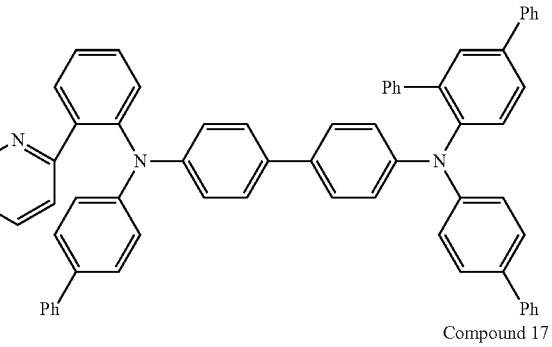
Compound 17
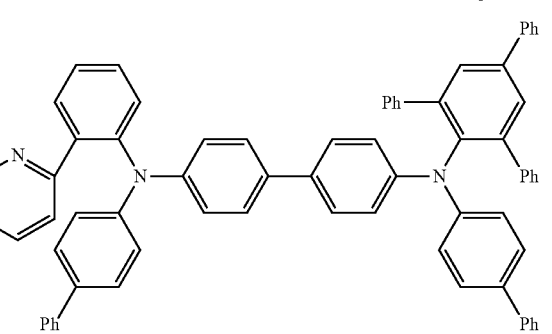
Compound 18
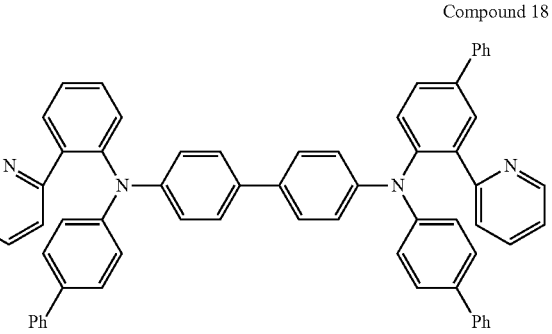

-continued
Compound 19
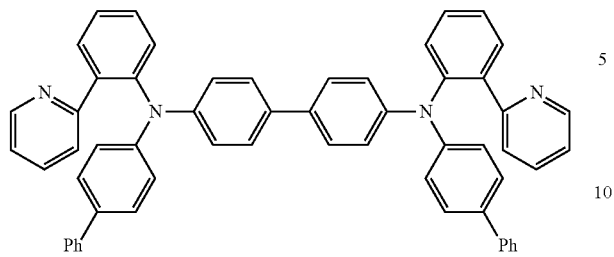
Compound 20
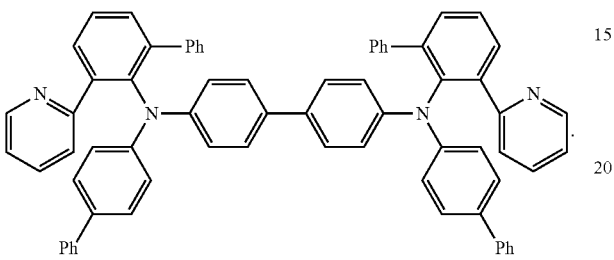
* * * * *